(12) United States Patent
Nakamura et al.

(10) Patent No.: US 9,012,420 B2
(45) Date of Patent: Apr. 21, 2015

(54) APTAMER FOR CHYMASE, AND USE THEREOF

(75) Inventors: Yoshikazu Nakamura, Tokyo (JP); Ling Jin, Tokyo (JP); Satoko Yamazaki, Tokyo (JP); Hisako Ikeda, Tokyo (JP); Masahiro Muraguchi, Osaka (JP)

(73) Assignees: Ribomic Inc., Tokyo (JP); Otsuka Pharmaceutical Co., Ltd., Tokyo (JP)

( * ) Notice: Subject to any disclaimer, the term of this patent is extended or adjusted under 35 U.S.C. 154(b) by 326 days.

(21) Appl. No.: 13/377,201

(22) PCT Filed: Jun. 11, 2010

(86) PCT No.: PCT/JP2010/059953
§ 371 (c)(1),
(2), (4) Date: Feb. 13, 2012

(87) PCT Pub. No.: WO2010/143714
PCT Pub. Date: Dec. 16, 2010

(65) Prior Publication Data
US 2012/0165401 A1    Jun. 28, 2012

(30) Foreign Application Priority Data

Jun. 11, 2009 (JP) ................. 2009-140585

(51) Int. Cl.
| | |
|---|---|
| *A61K 31/70* | (2006.01) |
| *C07H 21/02* | (2006.01) |
| *C07H 21/04* | (2006.01) |
| *C12N 15/115* | (2010.01) |
| *A61K 31/7105* | (2006.01) |
| *C12Q 1/68* | (2006.01) |

(52) U.S. Cl.
CPC ......... *C12N 15/115* (2013.01); *A61K 31/7105* (2013.01); *C12N 2310/16* (2013.01); *C12N 2310/322* (2013.01); *C12Y 304/21039* (2013.01)

(58) Field of Classification Search
None
See application file for complete search history.

(56) References Cited

U.S. PATENT DOCUMENTS

| | | | |
|---|---|---|---|
| 6,500,835 B2 | 12/2002 | Fukami et al. | |
| 2002/0183338 A1 | 12/2002 | Fukami et al. | |
| 2006/0003322 A1* | 1/2006 | Bentwich ............ | 435/6 |

FOREIGN PATENT DOCUMENTS

| | | |
|---|---|---|
| CN | 1366461 | 8/2002 |
| EP | 1 192 949 | 4/2002 |
| WO | 2005/113786 | 12/2005 |
| WO | 2007/002677 | 1/2007 |

OTHER PUBLICATIONS

International Search Report mailed Jul. 13, 2010 in corresponding International (PCT) Application No. PCT/JP2010/059953.
Translation of the Written Opinion of the International Searching Authority mailed Jul. 13, 2010 in corresponding International (PCT) Application No. PCT/JP2010/059953.
Xiao-Yan Zhao et al.; "Chymase Induces Pro Fibrotic Response Via Transforming Growth Factor-β1/Smad activation in Rat Cardiac Fibroblasts"; Molecular Cell Biochemistry; 2008; vol. 310; pp. 159-166.
Hideo Kanemitsu et al.; "Chronic Chymase Inhibition Preserves Cardiac Function After Left Ventricular Repair in Rats"; European Journal of Cardio-thoracic Surgery; 2008; vol. 33; pp. 25-31.
Suresh S. Palaniyandi et al.; "Chymase Inhibition Reduces the Progression to Heart Failure After Autoimmune Myocarditis in Rats"; Exp. Biol. Med.; 2007; vol. 232; pp. 1213-1221.
Naotaka Shiota et al.; "Effect of Mast Cell Chymase Inhibitor on the Development of Scleroderma in Tight-Skin Mice"; Br. J. Pharmacol; 2005; vol. 145, pp. 424-431.
Shin Miyakawa; "Development of RNA Aptamers for Therapeutics"; Drug Deliv. Syst.; 2008; vol. 23; No. 5; pp. 534-543.
Toshio Iwagawa et al.; "RNA Aptamer no Kaihatsu to Iyakuhin eno Oyo"; Medical Science Digest, Jan. 2009; vol. 35; No. 1, pp. 5-6.
Masatoshi Fumatara, "Kakusan Soyaku no Kaihatsu Jokyo", Jikken Igaku; Mar. 2009; vol. 27; No. 5; pp. 179-185.
Supplementary European Search Report dated Feb. 7, 2013 in EP Application No. 10786245.0.
S.M. Nimjee et al., "Aptamers: An Emerging Class of Therapeutics", Annul Review of Medicine: Selected Topics in the Clinical Sciences, vol. 56, pp. 555-583, 2005.
A. D. Keefe et al., "Aptamers as Candidate Therapeutics for Cardiovascular Indications", Current Opinion in Pharmacology, vol. 8, No. 2, pp. 147-152, Jan. 28, 2008.
Chinese Office Action issued in corresponding Application No. 201080025672.8 dated Nov. 5, 2012 with English translation.

\* cited by examiner

*Primary Examiner* — Sean McGarry
(74) *Attorney, Agent, or Firm* — Wenderoth, Lind & Ponack, L.L.P.

(57) ABSTRACT

Provided are an aptamer bound to chymase to inhibit activity of chymase; an aptamer containing a nucleotide sequence represented by $X_1GAUAGAN_1N_2UAAX_2$ wherein $X_1$ and $X_2$ are the same or different and each is A or G, and $N_1$ and $N_2$ are the same or different and each is A, G, C, U or T; a complex containing the aptamer and a functional substance (e.g., affinity substance, labeling substance, enzyme, drug delivery medium, drug and the like); a pharmaceutical or a reagent containing the aptamer or complex; a detection and a purification methods of chymase using the aptamer or complex and the like.

21 Claims, 8 Drawing Sheets

SEQ ID NO: 57

SEQ ID NO: 56

SEQ ID NO: 55

SEQ ID NO: 51

SEQ ID NO: 49

APTAMER FOR CHYMASE, AND USE THEREOF

This application is a U.S. national stage of International Application No. PCT/JP2010/059953 filed Jun. 11, 2010.

TECHNICAL FIELD

The present invention relates to an aptamer against chymase, a method of utilizing the same and the like.

BACKGROUND OF THE INVENTION

Human chymase (EC.3.4.21.39), a chymotrypsin-like serine protease, is stored in mast cell secretory granules. Upon external stimulation, mast cells undergo degranulation, resulting in the release of human chymase, along with a wide variety of inflammation mediators, outside the cells. The released human chymase specifically recognizes aromatic amino acids contained in substrate proteins and peptides, such as phenylalanine and tyrosine, and cleaves the peptide bonds adjoining to the amino acids. A representative substrate for human chymase is angiotensin I (AngI). Human chymase cleaves AngI to produce angiotensin II (AngII), a vasoconstricting factor.

Mammalian chymases are phylogenetically classified under two subfamilies: α and β. Primates, including humans, express only one kind of chymase, which belongs to the α family. Meanwhile, rodents express both the α and β families of chymase. In mice, there are a plurality of kinds of chymases, of which mouse mast cell protease-4 (mMCP-4), which belongs to the β family, is considered to be most closely related to human chymase, judging from its substrate specificity and mode of expression in tissue. In hamsters, hamster chymase-1, also a member of the β family, corresponds to human chymase. Meanwhile, mMCP-5 and hamster chymase-2, which belong to the α family as with human chymase, possess elastase-like activity and differ from human chymase in terms of substrate specificity.

Chymase is profoundly associated with the activation of transforming growth factor β (TGF-β). TGF-β exists in a latent form (latent-TGF-β) in extracellular matrices around epithelial cells and endothelial cells, and is retained in extracellular matrices via large latent TGF-β binding protein (LTBP). TGF-β is released from extracellular matrices as required and activated, and the activated TGF-β is a cytokine of paramount importance to living organisms reportedly involved in cell proliferation and differentiation and tissue repair and regeneration after tissue injury. Collapse of its signal leads to the onset and progression of a wide variety of diseases. It is thought that in this process, chymase is involved in the release of latent TGF-β from extracellular matrices and the conversion of latent TGF-β to active TGF-β.

Chymase is known to be associated with a broad range of diseases, including fibrosis, cardiovascular diseases, inflammation, allergic diseases and organ adhesion. Fibrosis is an illness characterized by abnormal metabolism of extracellular substrates in the lung, heart, liver, kidney, skin and the like, resulting in excess deposition of connective tissue proteins. In pulmonary fibrosis, for example, connective tissue proteins such as collagen deposit in excess in the lung, resulting in hard shrinkage of pulmonary alveoli and ensuing respiratory distress. Lung fibrosis has been shown to result from pneumoconiosis, which is caused by exposure to a large amount of dust, drug-induced pneumonia, which is caused by use of drugs such as anticancer agents, allergic pneumonia, pulmonary tuberculosis, autoimmune diseases such as collagen disease, and the like. However, there are not a few cases in which the cause is unknown.

The mechanism of onset of fibrosis at the molecular level has not been elucidated well. Generally, in normal states, the proliferation and functions of fibroblasts are well controlled. In case of serious or persistent inflammation or injury, however, the tissue repair mechanism works in excess, resulting in abnormal proliferation of fibroblasts and overproduction of connective tissue proteins. TGF-β is known as a factor that causes these phenomena. As evidence suggestive of its involvement, it has been reported that administration of an anti-TGF-β neutralizing antibody to an animal model of fibrosis causes decreased collagen expression and significantly suppressed fibrosis. In patients with idiopathic pulmonary fibrosis, increased levels of TGF-β and elevated counts of chymase-positive mast cells are observed.

Meanwhile, association of chymase in fibrosis has been demonstrated by experiments using animal models. In a hamster model of bleomycin-induced pulmonary fibrosis, facilitated chymase activity, increased expression of collagen III mRNA, tissue fibrosis and other phenomena are significantly reduced by chymase inhibitors. The same effects have been observed for a mouse model of bleomycin-induced pulmonary fibrosis; administration of chymase inhibitors suppressed chymase activity and reduced hydroxyproline content.

With these features, chymase inhibitors can be used as prophylactic or therapeutic drugs for diseases related to chymase, such as fibrosis. Chymase inhibitors that have been developed include small molecular compounds such as TPC-806, SUN-13834, SUN-C8257, SUN-C8077, and JNJ-10311795 (Patent document 1).

In recent years, applications of RNA aptamers to therapeutic drugs, diagnostic reagents, and test reagents have been drawing attention; some RNA aptamers have already been in clinical study stage or in practical use. In December 2004, the world's first RNA aptamer drug, Macugen, was approved as a therapeutic drug for age-related macular degeneration in the US. An RNA aptamer refers to an RNA that binds specifically to a target molecule such as a protein, and can be prepared using the SELEX (Systematic Evolution of Ligands by Exponential Enrichment) method (Patent documents 2-4). In the SELEX method, an RNA that binds specifically to a target molecule is selected from an RNA pool with about $10^{14}$ different nucleotide sequences. The RNA used has a random sequence of about 40 nucleotides, which is flanked by primer sequences. This RNA pool is allowed to mixed with a target molecule, and only the RNA that has bound to the target molecule is separated using a filter and the like. The RNA separated is amplified by RT-PCR, and this is used as a template for the next round. By repeating this operation about 10 times, an RNA aptamer that binds specifically to the target molecule can be acquired.

Aptamer drugs, like antibody drugs, can target extracellular proteins. With reference to many scientific papers and other reference materials in the public domain, aptamer drugs are judged to potentially surpass antibody drugs in some aspects. For example, aptamers often exhibit higher affinity and specificity for target molecules than do antibodies. Aptamers are unlikely to undergo immune elimination, and adverse reactions characteristic of antibodies, such as antibody-dependent cell-mediated cytotoxicity (ADCC) and complement-dependent cytotoxicity (CDC), are reportedly unlikely to occur with the use of aptamers. From the viewpoint of drug delivery, aptamers are likely to migrate to tissues because of their molecular size of about one-tenth that of antibodies, enabling easier drug delivery to target sites. Because aptamers are produced by chemical synthesis, they permit site-selective chemical modifications, and enable cost reduction by mass-production. Other advantages of aptamers include long-term storage stability, heat resistance and solvent resistance. Meanwhile, the blood half-lives of aptamers are generally shorter than those of antibodies; however, this property is sometimes advantageous in view of toxicity. These facts lead to the conclusion that even when the same molecule is targeted, aptamer drugs potentially surpass antibody drugs.

PRIOR DOCUMENT

Patent Document

[Patent Document 1] U.S. Pat. No. 6,500,835
[Patent Document 2] WO91/19813
[Patent Document 3] WO94/08050
[Patent Document 4] WO95/07364

SUMMARY OF THE INVENTION

Problems to be Solved by the Invention

The present invention is directed to providing an aptamer for chymase and a method for utilizing the same, and the like.

Means of Solving the Problems

The present inventors investigated diligently to solve the problem described above and succeeded in preparing an aptamer of good quality for chymase, which resulted in the completion of the present invention.

Accordingly, the present invention provides the following:
[1] An aptamer that binds to chymase to inhibit a chymase activity.
[2] The aptamer according to [1], comprising a nucleotide sequence represented by $X_1GAUAGAN_1N_2UAAX_2$ (SEQ ID NO: 21; each of $X_1$ and $X_2$, whether identical or not, is A or G, and each of $N_1$ and $N_2$, whether identical or not, is A, G, C, U or T).
[3] The aptamer according to [2], wherein $N_1N_2$ is GA, GU, GC, UU, GT or CU.
[4] The aptamer according to [2], wherein $X_1$ and $X_2$ are both A or both G.
[5] The aptamer according to [3] or [4], wherein at least one of the pyrimidine nucleotides has been modified or altered.
[6] The aptamer according to [1], comprising any one of the nucleotide sequences (a), (b) and (c) below:
(a) an aptamer comprising a nucleotide sequence selected from among SEQ ID NO: 4-34, 38-57, 59-65 and 69-72 (with the provision that the uracil may be thymine);
(b) an aptamer comprising a nucleotide sequence selected from among SEQ ID NO: 4-34, 38-57, 59-65 and 69-72 (with the provision that the uracil may be thymine), wherein 1 to 5 nucleotides are substituted, deleted, inserted or added; and
(c) a nucleotide sequence having an identity of 70% or more to a nucleotide sequence selected from among SEQ ID NO: 4-34, 38-57, 59-65 and 69-72 (with the provision that the uracil may be thymine).
[7] The aptamer according to [6], wherein at least one of the nucleotides contained in the aptamer has been modified or altered.
[8] The aptamer according to [1], comprising any one of the nucleotide sequences (a'), (b') and (c') below:
(a') a nucleotide sequence selected from among SEQ ID NOs: 73-131 (with the provision that the uracil may be thymine);
(b') a nucleotide sequence selected from among SEQ ID NOs: 73-131 (with the provision that the uracil may be thymine), wherein 1 to 5 nucleotides are substituted, deleted, inserted or added; and
(c') a nucleotide sequence having an identity of 70% or more to a nucleotide sequence selected from among SEQ ID NOs: 73-131 (with the provision that the uracil may be thymine).
[9] The aptamer according to [1], wherein each of the hydroxy groups at the 2'-positions of respective pyrimidine nucleotides contained in the aptamer, whether identical or not, may be substituted by an atom or a group selected from the group consisting of a hydrogen atom, a fluorine atom and a methoxy group.
[10] The aptamer according to [1], wherein each of the hydroxy groups at the 2'-positions of respective purine nucleotides contained in the aptamer, whether identical or not, may be substituted by an atom or a group selected from the group consisting of a hydrogen atom, a fluorine atom and a methoxy group.
[11]A complex comprising any one of the aptamers [1] to [10] and a functional substance.
[12] The complex according to [11], wherein the functional substance is an affinity substance, a substance for labeling, an enzyme, a drug delivery vehicle or a drug.
[13]A pharmaceutical comprising any one of the aptamers [1] to [10] or the complex [11] or [12].
[14] The pharmaceutical according to [13], which is used to prevent or treat a cardiovascular disease or fibrosis.
[15]A diagnostic reagent comprising any one of the aptamers [1] to [10] or the complex [11] or [12].
[16]A chymase detection probe comprising any one of the aptamers [1] to [10] or the complex [11] or [12].
[17]A solid phase carrier for chymase purification comprising any one of the aptamers [1] to [10] or the complex [11] or [12].
[18]A method of detecting chymase, comprising using any one of the aptamers [1] to [10] or the complex [11] or [12].
[19]A method of purifying chymase, comprising using any one of the aptamers [1] to [10] or the complex [11] or [12].

Effect of the Invention

The aptamer or the complex of the present invention can be useful as a pharmaceutical or reagent such as a diagnostic reagent for various diseases caused by chymase, such as fibrosis and cardiovascular diseases. The aptamer or the complex of the present invention can also be useful in purifying and concentrating chymase, and detecting and quantifying chymase.

Figure 4:
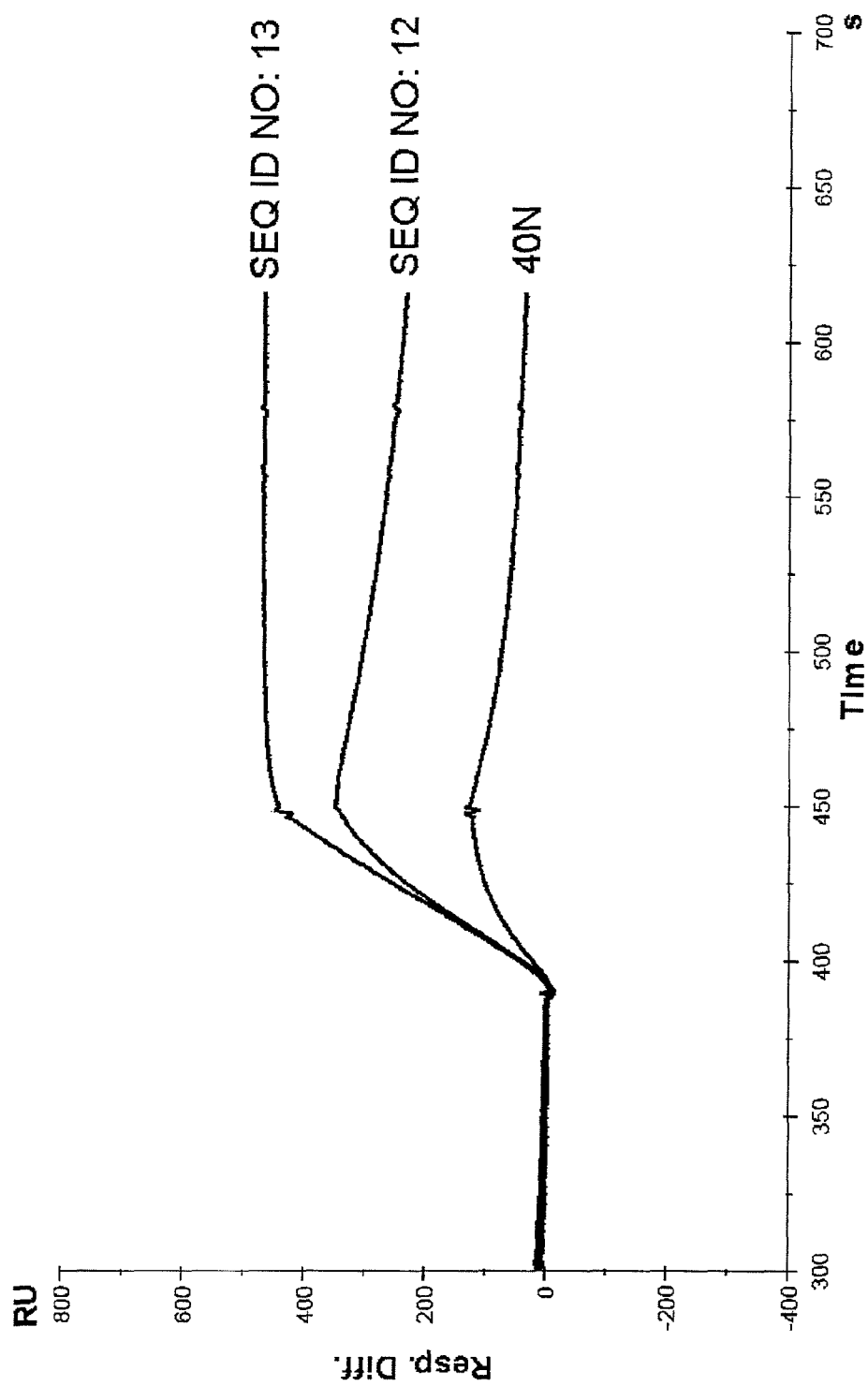

FIG. 4 shows how the aptamers shown by SEQ ID NO: 12 and 13 bind to chymase, wherein 40N indicates an RNA pool containing a random sequence of 40 nucleotides. As a capture molecule, each aptamer or the negative control 40N was immobilized; as an analyte, human chymase was injected. The measurements were taken using Biacore T100 (manufactured by GE Healthcare).

Figure 5:
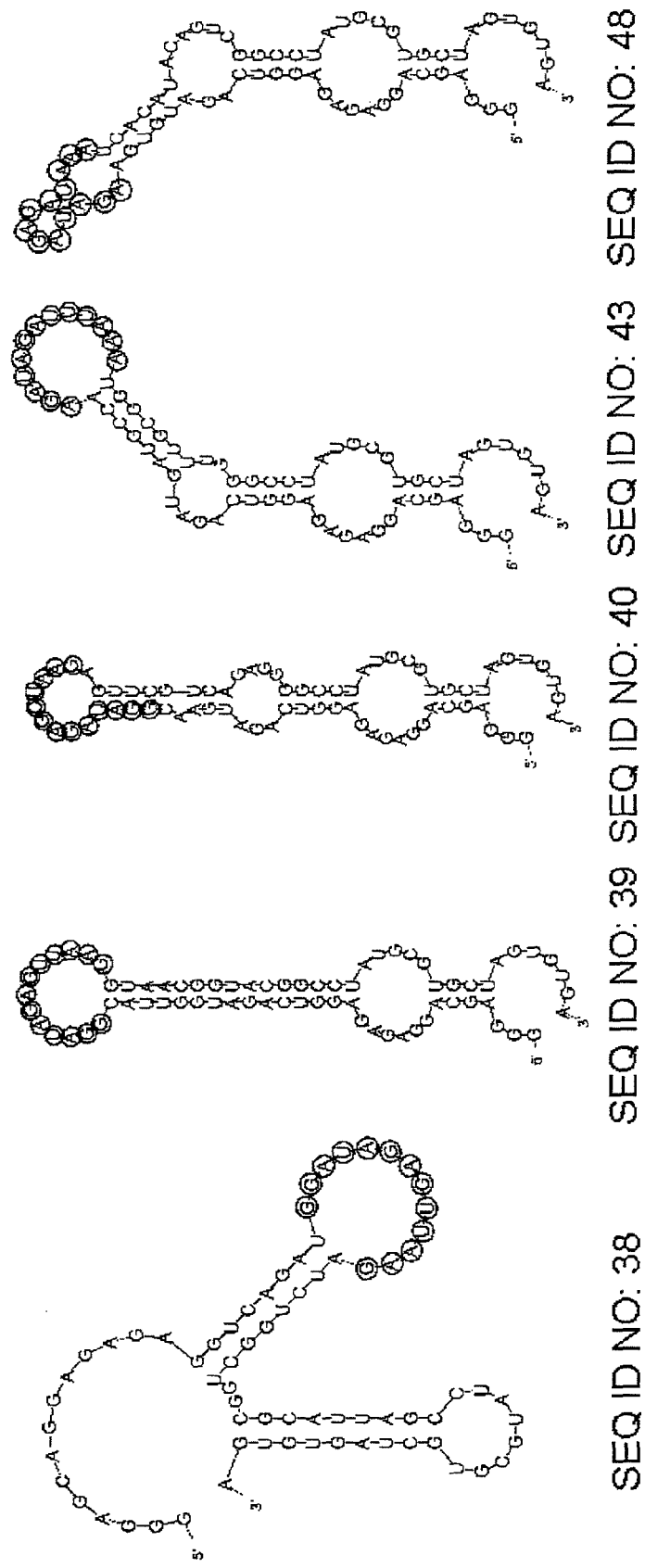

FIG. 5 shows the secondary structure of aptamer shown by SEQ ID NO: 38-40, 43, 48 predicted by the MFOLD program, wherein the part enclosed in a circle shows a common sequence shown by SEQ ID NO: 21.

Figure 6:
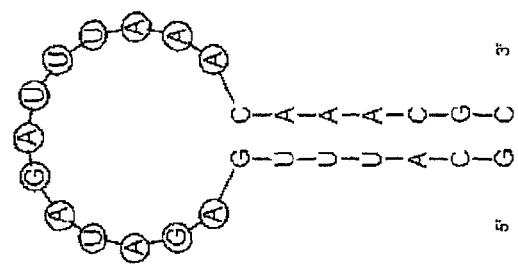
Figure 6:
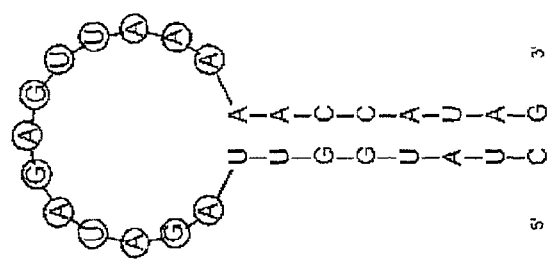
Figure 6:
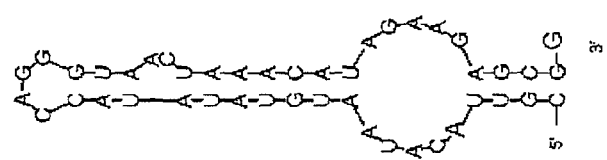
Figure 6:
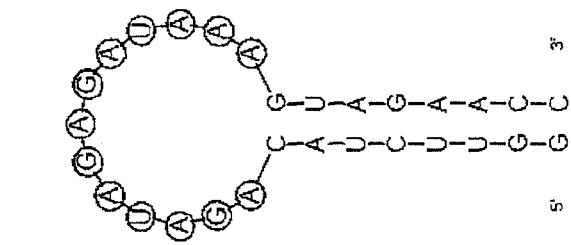

FIG. 6 shows the secondary structure of aptamer shown by SEQ ID NO: 49, 51, 55-57 predicted by the MFOLD program, wherein the part enclosed in a circle shows a common sequence shown by SEQ ID NO: 21.

Figure 7:
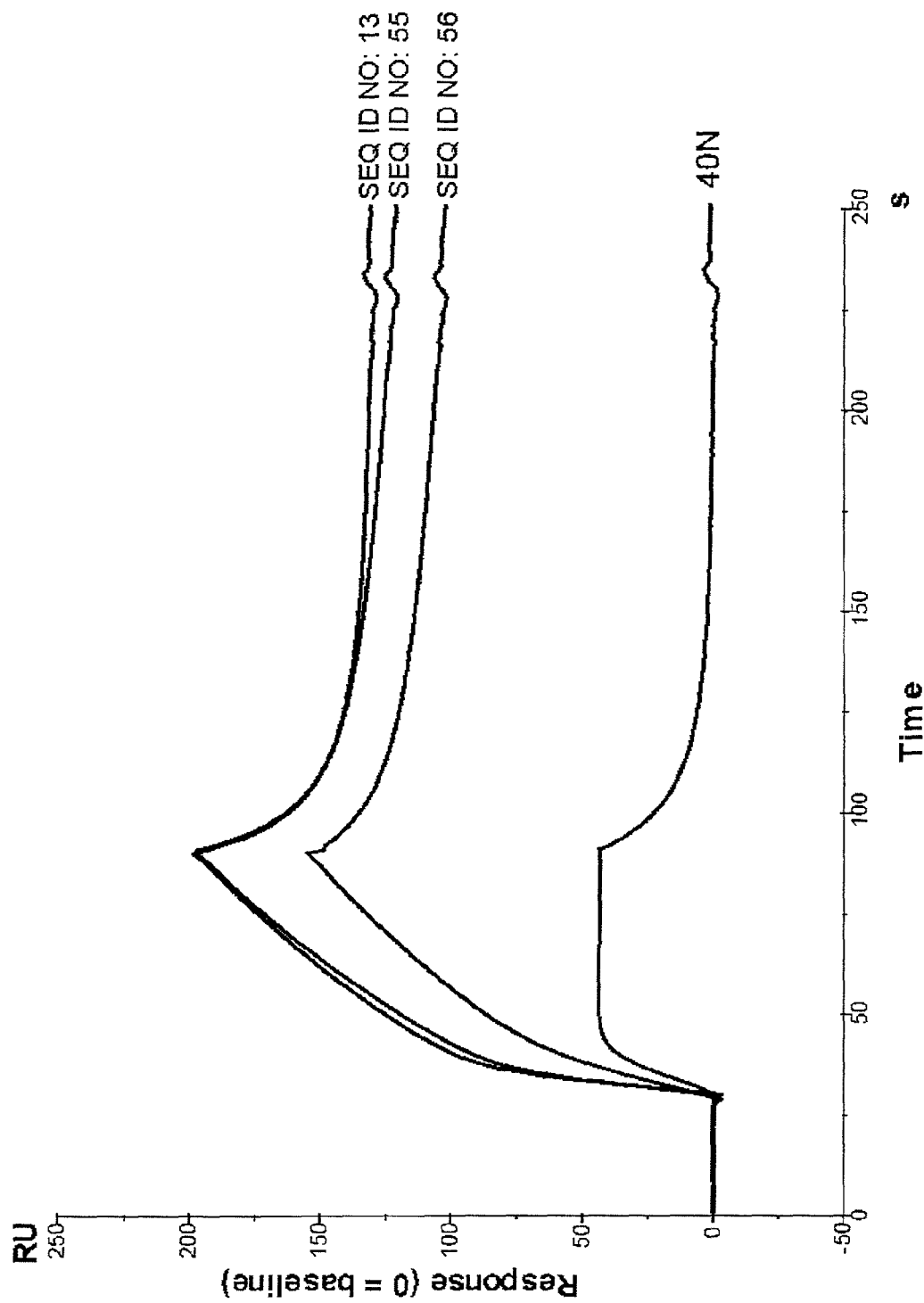

FIG. 7 shows how the aptamers shown by SEQ ID NO: 13, 55, and 56 bind to chymase, wherein 40N indicates an RNA pool containing a random sequence of 40 nucleotides. Chymase was immobilized onto a chip surface; as an analyte, each aptamer or the negative control 40N was injected. The measurements were taken using Biacore T100 (manufactured by GE Healthcare)

Figure 8:
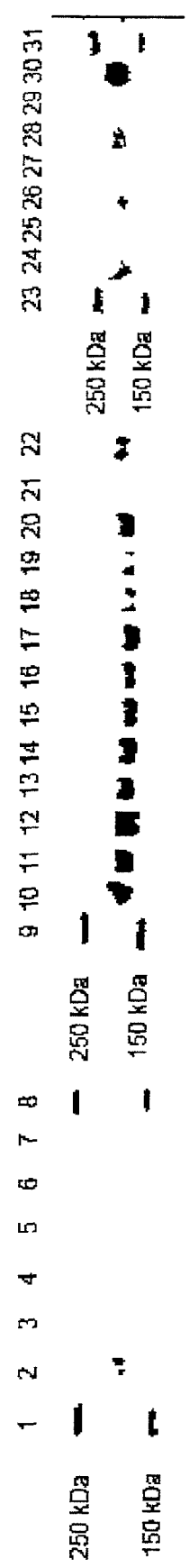

FIG. 8 shows the results of detection by Western blotting of how LTBP-1 was degraded by chymase and how the LTBP-1 degradation was inhibited by the aptamers listed in Table 9. Lane numbers 1, 8, 9, 23, and 31 show the markers; lane numbers 6, 21, and 29 show the results for negative controls (no inhibitor); lane numbers 7, 22, and 30 show the results for chymase-free controls.

BEST MODE FOR CARRYING OUT THE INVENTION

The present invention provides an aptamer possessing a binding activity for chymase. The aptamers of the present invention are capable of inhibiting activities of chymase.

An aptamer refers to a nucleic acid molecule having a binding affinity for a particular target molecule. The aptamer can also inhibit the activity of a particular target molecule by binding to the particular target molecule. The aptamer of the present invention possesses binding activity for chymase, and is capable of inhibiting a chymase activity. The aptamer of the present invention can be an RNA, a DNA, a modified nucleic acid or a mixture thereof. The aptamer of the present invention can also be in a linear or circular form.

Chymase, a publicly known serine protease, is stored in mast cell secretory granules. Chymase is profoundly involved in a wide variety of biological reactions mediated by mast cells, including, for example, bioactive peptide production and degradation, extracellular matrix remodeling, networks with cytokines, and immunity. The aptamer of the present invention can exhibit inhibitory activity against chymase derived from any mammals. Such mammals include primates (e.g., humans, monkeys), rodents (e.g., mice, rats, guinea pigs, hamsters), and companion animals, domesticated animals and work animals (e.g., dogs, cats, horses, bovines, goat, sheep, pigs), with preference given to humans. The amino acid sequence of human chymase is shown by Accession Number AAB26828, and may be a sequence having one to several mutated residues, a domain moiety thereof, or a peptide moiety thereof. The structure of human chymase may be not only a monomer, but also a dimer or polymer.

The aptamer of the present invention binds to chymase in physiological buffer solutions. Although there is no limitation on the choice of buffer solution, preference is given to buffer solutions having a pH of about 5.0-10.0. Such buffer solutions include, for example, the solution A and solution C described below (see Examples 1 and 2). The aptamer of the present invention binds to chymase at strength detectable by any one of the tests described below.

Binding strength is measured using Biacore T100 (manufactured by GE Healthcare). In a method of measurement, the aptamer is first immobilized onto a sensor chip, the amount immobilized being about 1000 RU. 20 µL of a chymase solution for analyte, prepared at 0.2 µM, is injected, and the binding of chymase to the aptamer is detected. An RNA comprising a random nucleotide sequence of 30 or 40 nucleotides is used as a negative control. If the chymase binds to the aptamer equivalently or significantly more potently compared with the control RNA, the aptamer is judged to have the capability of binding to chymase.

In another method, chymase is first immobilized onto a sensor chip, the amount immobilized being about 4000 RU. 20 µL of an aptamer solution for analyte, prepared at 0.01 µg/µL, is injected, and the binding of the aptamer to chymase is detected. An RNA containing a random nucleotide sequence of 30 or 40 nucleotides is used as a negative control. If the chymase binds to the aptamer equivalently or significantly more potently compared with the control RNA, the aptamer is judged to have the capability of binding to chymase.

An inhibitory activity against chymase means an inhibitory potential against any activities possessed by chymase. For example, enzyme activity to hydrolyze and cleave peptide chains, which is one of the functions of chymase, is inhibited. Acceptable substrates for enzyme activity are not limited to proteins and bioactive peptides present in living organisms (e.g., AngI, latent TGF-β and the like), but include peptides, containing partial amino acid sequences of the foregoing peptides, conjugated with chromogenic substance or fluorescent substance. Chromogenic substances and fluorescent substances are known to those skilled in the art. Phenomena that occur via protein or bioactive peptide degradation reactions include increased expression of collagen I/III, increased hydroxyproline content, increased expression of IgE and the like; suppressive effects thereon are also included in the inhibitory activities against chymase. In addition, inhibitory activities against the migration of neutrophils, monocytes, and eosinophils to chymase is also included in inhibitory activity against chymase. Furthermore, suppressive effects against chymase-induced histamine release promotion, mast cell count elevation, increased vascular permeability, tissue fibrosis, inflammation, angiogenesis, vascular intimal thickening and the like are also included in the inhibitory activities against chymase.

A substrate for chymase means a peptide, protein or the like that undergoes hydrolytic cleavage by chymase. Substrates for chymase known to exist in living organisms include peptides and proteins such as AngI, latent TGF-β, stem cell factor (SCF), procollagen, procollagenase, fibronectin, promatrix metalloprotease-1 (pro-MMP-1), pro-MMP-9, tissue inhibitor of matrix metalloproteinase-1 (TIMP-1), apolipoprotein A-I (apoA-I), apoE, phospholipid transfer protein, IL-1β precursor, big-endothelin-1 (big-ET-1), big-ET-2, connective tissue-activating peptide III, IL-18 precursor, substance P, vasoactive intestinal peptide (VIP), kallidin, bradykinin, and C3a. Herein, chymase substrates are not limited to them, but include artificially designed model peptides comprising amino acid residues specifically recognized by chymase, such as Phe and Tyr, as well as these peptides conjugated with chromogenic substance or fluorescent substance.

Whether an aptamer inhibits the enzyme activity of chymase can be determined by, for example, the three testing methods described below.

A first method employs a synthetic substrate. A useful chymase substrate is Suc-Ala-Ala-Pro-Phe-MCA (4-methyl-coumaryl-7-amide group) (manufactured by Peptide Institute, Inc.), which contains the 4-amino acid peptide "Ala-Ala-Pro-Phe", a standard substrate for chymotrypsin-like proteases.

The assay is performed using a 96-well plate (F16 Black Maxisorp Fluoronunc, manufactured by Nunc), with a reaction mixture volume of 100 µL, in a buffer solution (solution C; see Example 2 below). First, each nucleic acid is prepared in solution C to obtain 50 µL solutions. After 10 µL of the 1 mM substrate prepared in solution C is added, the plate is set to the microplate reader SpectraMax190 (manufactured by Molecular Devices Corporation), and incubated at 37° C. for 5 minutes. Separately, 0.05 µg of chymase (recombinant, manufactured by SIGMA) is diluted in solution C, and 40 µL of this dilution is incubated at 37° C. for 5 minutes. The chymase solution is added to the mixture of the nucleic acid and substrate to initiate an enzyme reaction. The plate containing the reaction mixture is set to the microplate reader SpectraMax190 (manufactured by Molecular Devices Corporation), and examined for time-dependent changes in the fluorescence intensity at 37° C. for 5 minutes (excitation wavelength 380 nm, detection wavelength 460 nm). A linear approximation of the increase in the fluorescence of the AMC (7-amino-4-methylcoumarine) released from the substrate by chymase activity is generated, and its slope is taken as the initial reaction velocity. For control, samples are treated and analyzed in the same manner in two cases: use of a nucleic acid pool containing a random sequence of 30 or 40 nucleotides (negative control), and use of chymostatin, a known chymotrypsin-like serine protease inhibitor (positive control). Taking the initial reaction velocity without the nucleic acid and inhibitor as a 100% enzyme activity, the inhibitory rate for each test substance is calculated, and the inhibitor concentration required to cause a 50% inhibition of the enzyme activity ($IC_{50}$) is determined. An aptamer exhibiting a lower $IC_{50}$ value than that of chymostatin, a known inhibitor, is judged to possess excellent inhibitory activity.

A second method of evaluation employs a native substrate. A useful native substrate for chymase is angiotensin I. Here, His-Leu, a peptide fragment released upon degradation of angiotensin I, is fluorescently derivatized, and the fluorescence intensity therefrom is quantified.

In the assay, an enzyme reaction is carried out in 50 µL of solution C. First, 0.3-0.75 ng of chymase (recombinant, manufactured by SIGMA; or native, manufactured by Calbiochem) is diluted in solution C to obtain 5 µL chymase solution. Each nucleic acid is prepared in solution C to obtain 25 µL solutions. 5 µL of each chymase dilution and 25 µL of each nucleic acid solution are mixed, and then the mixture is incubated at 37° C. for 5 minutes. Separately, 20 µL of 125 µM angiotensin I (manufactured by Peptide Institute, Inc.) is prepared in solution C and incubated at 37° C. for 5 minutes. The angiotensin I solution is added to the mixture of chymase and nucleic acid, and the enzyme reaction is initiated. After the reaction was allowed to proceed at 37° C. for 90 minutes, 25 µL of ice-cooled 30% trichloroacetic acid solution is added to terminate the reaction. The entire mixture is centrifuged at 4° C., 14000 rpm for 10 minutes, and 30 µL of the resulting supernatant is used for the subsequent reaction for fluorescent derivatization.

After 30 µL of the supernatant is added to a 96-well plate (Black, manufactured by Costar), 15 µL of 2% o-phthalaldehyde (manufactured by SIGMA) solution in methanol and 170 µL of 0.3M NaOH solution are mixed in each well, and the plate is allowed to stand at room temperature for 10 minutes. Subsequently, 25 µL of 3M HCl solution is added to terminate the reaction. The plate is set to the microplate reader SpectraMax190 (manufactured by Molecular Devices Corporation), and the fluorescence intensity is determined at an excitation wavelength of 355 nm and a fluorescence wavelength of 460 nm.

For control, samples are treated and analyzed in the same manner in two cases: use of SEQ ID NO: 58 (negative control) and use of chymostatin, a known chymotrypsin-like serine protease inhibitor (positive control). In both cases, fluorescence intensity obtained at 0 minute reaction time serves as a blank determination. Taking the fluorescence intensity detected with the addition of an equal volume of solution C, in place of each nucleic acid, in the chymase enzyme reaction as 100%, the inhibitory rate for each test substance is calculated, and the inhibitor concentration required to cause a 50% inhibition of the enzyme activity ($IC_{50}$) is determined. An aptamer exhibiting a lower $IC_{50}$ value than that of chymostatin, a known inhibitor, is judged to possess excellent inhibitory activity.

A third method of evaluation employs a native substrate contained in a cell culture supernatant. Here, degradation of chymase substrate LTBP-1 is detected by Western blotting. NHLF cells (manufactured by Cambrex Bio Science) under freezing are rapidly thawed in a 37° C. water bath, and then suspended in a medium (10% FBS/F-12). After centrifugation at 1200 rpm for 5 minutes, the resulting supernatant is removed, and the cells are re-suspended in the medium. Total volume of 10 mL medium is added to the centrifuged cells, and the cell suspension is transferred to a cell culture dish and cultured at 37° C. in the presence of 5% $CO_2$. The cells are observed morphology and proliferation status under a microscope. When the cells become confluent, the medium is replaced with a serum-free medium (0.2% BSA/F-12). Two days after replacement of the medium, the culture supernatant is collected, dispensed, and stored under freezing at −30° C.

After 40 µL of the NHLF culture supernatant, freshly thawed before use, is dispensed to a tube, 5 µL of the nucleic acid solution diluted with solution C is added thereof. For positive control, chymostatin is diluted with solution C, and this dilution is added in the same manner. For negative control, solution C alone is added. Next, 5 µL of a 100 ng/mL dilution of chymase in solution E (solution C+0.1% BSA, 0.05% sodium azide) is added. For control, a chymase-free tube is prepared. After stirring, the sample is incubated at 37° C. for 1 hour, and mixed with an equal volume of lysis buffer for electrophoresis to terminate the reaction. LTBP-1 in the sample is detected by the procedure of Western blotting described below.

The sample mixed in the lysis buffer is boiled for 3 minutes, and 10 µL of the sample is subjected to electrophoresis on 5-20% acrylamide gel. After completion of the electrophoresis, the sample is transferred onto a nitrocellulose filter, after which the filter is blocked with 5% skimmed milk, 50 mM Tris-HCl (pH 8.0), and 0.05% sodium azide. The filter is reacted with a 2 µg/mL dilution of anti-LTBP-1 monoclonal antibody in 2% BSA, PBS, and 0.05% sodium azide at room temperature overnight. The filter is washed 3 times and incubated with secondary antibody solution (HRP-labeled anti-mouse IgG antibody diluted 10000 fold with 0.1% BSA/PBS) at room temperature for 2 hours. The filter is washed 5 times, and detection is performed using a chemiluminescent substrate.

As determined according to LTBP-1 band density and position (molecular weight), the band from the chymase-free well serves for positive control (+), and the band from the negative control well serves for negative control (−). Each test substance is examined for inhibitory activity by visual inspection.

There is no limitation on the aptamer of the present invention, as far as it is capable of binding to any portions of chymase to inhibit the activity thereof.

The length of the aptamer of the present invention is not limited, and can usually be about 10 to about 200 nucleotides, and can be, for example, not more than about 100 nucleotides, preferably not more than about 50 nucleotides, more preferably not more than about 40 nucleotides, most preferably not more than about 30 nucleotides. When the total number of nucleotides is smaller, chemical synthesis and mass-production will be easier, and there is a major advantage in terms of cost. It is also thought that chemical modification is easy, stability in the body is high, and toxicity is low.

Each of the nucleotides contained in the aptamer of the present invention, whether identical or different, can be a nucleotide comprising a hydroxyl group at the 2' position of ribose (e.g., ribose of pyrimidine nucleotide, ribose of purine nucleotide) (i.e., an unsubstituted nucleotide) or a nucleotide substituted by any atom or group at the 2' position of ribose. As examples of such any atom or group, a nucleotide substituted by a hydrogen atom, a fluorine atom or an —O-alkyl group (e.g., —O-Me group), an —O-acyl group (e.g., —O—COMe group), or an amino group (e.g., —NH$_2$ group) can be mentioned.

The aptamer of the present invention has a sequence represented by $X_1$GAUAGAN$_1$N$_2$UAAX$_2$ (SEQ ID NO: 21; wherein each of $X_1$ and $X_2$, whether identical or not, is A or G, and each of $N_1$ and $N_2$, whether identical or not, is A, G, C, U or T; with the provision that the uracil may be thymine). An aptamer having this sequence strongly binds to chymase to inhibit a chymase activity.

In the formula above, $X_1$ and $X_2$ are preferably both A or both G; $N_1N_2$ is preferably GA, GU, GC, UU, GT or CU (with the provision that the uracil may be thymine).

The aptamer of the present invention can also be the nucleotide wherein at least one kind (e.g., 1, 2, 3 or 4 kinds) of nucleotide comprises a hydroxyl group, or the above-described any atom or group, for example, at least two kinds (e.g., 2, 3 or 4 kinds) of groups selected from the group consisting of a hydrogen atom, a fluorine atom, a hydroxyl group and a methoxy group, at the 2' position of ribose.

In the aptamer of the present invention, all pyrimidine nucleotides can be nucleotides substituted by a fluorine atom, or nucleotides substituted by any atom or group mentioned above, preferably an atom or group selected from the atom or group consisting of a hydrogen atom, a hydroxyl group and a methoxy group whether identical or not, at the 2' position of ribose.

In the aptamers of the present invention, all purine nucleotides can be nucleotides comprising a hydroxyl group, or nucleotide substituted by any atom or group mentioned above, preferably an atom or a group selected from the group consisting of a hydrogen atom, a methoxy group, and a fluorine atom, whether identical or not, at the 2'-position of ribose.

The aptamer of the present invention can also be one wherein all nucleotides identically comprise a hydroxyl group, or any atom or group mentioned above, for example, the identical group selected by the group consisting of a hydrogen atom, a fluorine atom, a hydroxyl group and a methoxy group, at the 2' position of ribose.

Herein, in this specification, the nucleotides constituting the aptamer are assumed to be RNAs (i.e., the sugar groups are assumed to be ribose) in describing how the sugar groups are modified in the nucleotides. However, this does not mean that DNA is exempted from the aptamer-constituting nucleotides, and a modification of RNA should read as a modification of DNA as appropriate. When the nucleotide constituting the aptamer is DNA, for example, substitution of the hydroxyl group at the 2' position of ribose by X should read as a substitution of one hydrogen atom at the 2' position of deoxyribose by X.

The aptamer of the present invention can also be:

(a) an aptamer comprising a nucleotide sequence selected from among SEQ ID NO:4-34, 38-57, 59-65 and 69-72 (with the provision that the uracil may be thymine);

(b) an aptamer comprising a nucleotide sequence selected from among SEQ ID NO:4-34, 38-57, 59-65 and 69-72 (with the provision that the uracil may be thymine), wherein 1 to 5 nucleotides are substituted, deleted, inserted or added; or (c) an aptamer comprising a nucleotide sequence having an identity of 70% or more (preferably 80% or more, more preferably 90% or more, most preferably 95% or more) to a nucleotide sequence selected from among SEQ ID NO: 4-34, 38-57, 59-65 and 69-72 (with the provision that the uracil may be thymine). The aptamer of the present invention also includes:

(d) a conjugate selected from the group consisting of a conjugate of a plurality of aptamers (a) above, a conjugate of a plurality of aptamers (b) above, a conjugate of a plurality of aptamers (c) above, and a conjugate of a plurality of aptamers (a), (b) and (c) above.

Not only the aptamer (a) above, but also the aptamers (b) to (d) are capable of binding to chymase and/or inhibiting a chymase activity (chymase enzyme activity and the like).

The aptamer of the present invention can also be:

(a') an aptamer comprising a nucleotide sequence selected from among SEQ ID NOs: 73-131 (with the provision that the uracil may be thymine);

(b') an aptamer comprising a nucleotide sequence selected from among SEQ ID NOs: 73-131 (with the provision that the uracil may be thymine), wherein 1 to 5 nucleotides are substituted, deleted, inserted or added; or (c') an aptamer comprising a nucleotide sequence having an identity of 70% or more to a nucleotide sequence selected from among SEQ ID NOs: 73-131 (with the provision that the uracil may be thymine). The aptamer of the present invention also includes:

(d') a conjugate selected from the group consisting of a conjugate of a plurality of aptamers (a') above, a conjugate of a plurality of aptamers (b') above, a conjugate of a plurality of aptamers (c') above, and a conjugate of a plurality of aptamers (a'), (b') and (c') above. Furthermore, the aptamer of the present invention also includes:

(e) a conjugate consisting of one or more aptamers selected from the group consisting of (a), (b) and (c) above, and one or more aptamers selected from the group consisting of (a'), (b') and (c').

The aptamers (a')-(d') and (e) above are also capable of binding to chymase and/or inhibiting a chymase activity (chymase enzyme activity and the like).

In (b) and (b') above, there is no limitation on the number of nucleotides substituted, deleted, inserted or added, as far as the aptamer is capable of binding to chymase and/or inhibiting a chymase activity (chymase enzyme activity and the like). The number of nucleotides can be, for example, not more than about 30, preferably not more than about 20, more preferably not more than about 10, still more preferably not more than 5, most preferably 4, 3, 2 or 1.

With respect to (c) and (c') above, "an identity" means a ratio (%) of identical nucleotide residues to all overlapping nucleotide residues in the optimal alignment where two nucleotide sequences are aligned using a mathematical algorithm known in the technical field (preferably, the algorithm considers introduction of gaps on one or both of the sequences for the best alignment).

Nucleotide sequence identity in the present description can be calculated by, for example, aligning the two nucleotide sequences using the homology calculation algorithm NCBI BLAST-2 (National Center for Biotechnology Information Basic Local Alignment Search Tool) under the following conditions (gap open=5 penalties; gap extension=2 penalties; x_dropoff=50; expectancy=10; filtering=ON).

In (d), (d') and (e) above, conjugation can be achieved by tandem binding. In the conjugation, a linker may be utilized. As the linker, nucleotide chains (e.g., 1 to about 20 nucleotides) and non-nucleotide chains (e.g., —($CH_2$)n- linker, —($CH_2CH_2O$)n- linker, hexaethylene glycol linker, TEG linker, peptide-containing linker, —S—S— bond-containing linker, —CONH— bond-containing linker, —$OPO_3$— bond-containing linker) can be mentioned. The plurality as mentioned in the above-described plurality of conjugates is not particularly limited, as long as it is two or more, and the plurality can be, for example, 2, 3 or 4. Each of the nucleotides in (a) to (d), (a') to (d') and (e) above, whether identical or different, can be a nucleotide comprising a hydroxyl group at the 2' position of ribose or a nucleotide substituted by any groups (e.g., hydrogen atom, fluorine atom or —O-Me group) at the 2' position of ribose (e.g., ribose of pyrimidine nucleotide).

The aptamer of the present invention may be one wherein a sugar residue (e.g., ribose) of each nucleotide has been modified to increase the chymase binding activity, stability, drug deliverability and the like. As examples of the site to be modified in a sugar residue, one having the oxygen atom at the 2'-position, 3'-position and/or 4'-position of the sugar residue replaced with another atom, and the like can be mentioned. As examples of the modification, fluorination, O-alkylation (e.g., O-methylation, O-ethylation), O-arylation, S-alkylation (e.g., S-methylation, S-ethylation), S-arylation, and amination (e.g., —$NH_2$) can be mentioned. Such alterations in the sugar residue can be performed by a method known per se (see, for example, Sproat et al., (1991) Nucle. Acid. Res. 19, 733-738; Cotton et al., (1991) Nucl. Acid. Res. 19, 2629-2635; Hobbs et al., (1973) Biochemistry 12, 5138-5145).

The aptamer of the present invention may also have a nucleic acid base (e.g., purine or pyrimidine) altered (e.g., chemical substitution) to increase the chymase binding activity and the like. As examples of such alterations, 5-position pyrimidine alteration, 6- and/or 8-position purine alteration, alteration with an extracyclic amine, substitution with 4-thiouridine, and substitution with 5-bromo or 5-iodo-uracil can be mentioned.

The phosphate group contained in the aptamer of the present invention may be altered to confer resistance to nuclease and hydrolysis. For example, the P(O)O group may be substituted with P(O)S (thioate), P(S)S (dithioate), P(O)$NR_2$ (amidate), P(O)$CH_3$, P(O)$BH_3$, P(O)R, R(O)OR', CO or $CH_2$ (formacetal) or 3'-amine (—NH—$CH_2$—$CH_2$—) [wherein each unit of R or R' is independently H or a substituted or unsubstituted alkyl (e.g., methyl, ethyl)].

The joining group is, for example, —O—, —N— or —S—, and nucleotides can bind to an adjoining nucleotide via these joining groups.

The alterations may also include alterations such as capping at 3' and 5'.

An alteration can further be performed by adding to an end a polyethyleneglycol, amino acid, peptide, inverted dT, nucleic acid, nucleosides, Myristoyl, Lithocolic-oleyl, Docosanyl, Lauroyl, Stearoyl, Palmitoyl, Oleoyl, Linoleoyl, other lipids, steroids, cholesterol, caffeine, vitamins, pigments, fluorescent substances, anticancer agent, toxin, enzymes, radioactive substance, biotin and the like. For such alterations, see, for example, U.S. Pat. Nos. 5,660,985 and 5,756,703.

The aptamer of the present invention can be synthesized as disclosed herein and by a method known per se in the art. A method of synthesis employs RNA polymerase. A DNA having a desired sequence and a promoter sequence of RNA polymerase is chemically synthesized, which, as a template, is transcribed by a publicly known method to obtain the desired RNA. The aptamer of the present invention can also be synthesized using DNA polymerase. A DNA having a desired sequence is chemically synthesized, which, as a template, is amplified by a method of public knowledge known as the polymerase chain reaction (PCR). This is rendered single-stranded by a publicly known method of polyacrylamide electrophoresis or enzyme treatment. When synthesizing a modified aptamer, elongation reaction efficiency can be increased by using a polymerase mutated at a particular site. The aptamer thus obtained can easily be purified by a publicly known method.

An aptamer can be synthesized in large amounts by chemical synthetic methods such as the amidite method and the phosphoramidite method. These synthetic methods are well known, as described in Nucleic Acid (Vol. 2) [1] Synthesis and Analysis of Nucleic Acid (edited by Yukio Sugiura, published by Hirokawa Publishing Company) and the like. Practically, a synthesizer such as OligoPilot100 or OligoProcess (manufactured by GE Healthcare Bioscience) is used. The aptamer thus synthesized can be purified by a method known per se such as chromatography.

Provided that an active group such as an amino group is introduced to an aptamer during the process of chemical synthesis by the phosphoramidite method or the like, a functional substance can be added after the synthesis. For example, by introducing an amino group to an end of the aptamer, it is possible to condense a polyethylene glycol chain incorporating a carboxyl group.

An aptamer binds to the target molecule in a wide variety of binding modes, such as ionic bonds based on the negative charge of the phosphate group, hydrophobic bonds and hydrogen bonds based on ribose, and hydrogen bonds and stacking interaction based on nucleic acid bases. In particular, ionic bonds based on the negative charge of the phosphate group, which are present in the same number as the number of constituent nucleotides, are strong, and bind to lysine and arginine being present on the surface of the positive charge of protein. For this reason, nucleic acid bases not involved in the direct binding to the target molecule can be substituted. In particular, because the region of stem structure has already formed base pairs and faces the inside of the double helical structure, nucleic acid bases are unlikely to bind directly to the target molecule. Therefore, even when a base pair is replaced with another base pair, the activity of the aptamer often does not decrease. In structures wherein no base pairs are formed, such as loop structures, provided that the nucleic acid base is not involved in the direct binding to the target molecule, base substitution is possible. Regarding modifications of the 2'-position of ribose, the functional group at the 2'-position of ribose infrequently interacts directly with the target molecule, but in many cases, it is of no relevance, and can be substituted by another modified molecule. Hence, an aptamer, unless the functional group involved in the direct binding to the target molecule is substituted or deleted, often retains the activity thereof. It is also important that the overall three-dimensional structure does not change widely.

An aptamer can be prepared by utilizing the SELEX method or an improved version thereof (for example, Ellington et al., (1990) Nature, 346, 818-822; Tuerk et al., (1990) Science, 249, 505-510). In the SELEX method, by rendering the selection criteria more rigorous by increasing the number of rounds or using a competing substance, an aptamer exhibiting a stronger binding potential for the target molecule is concentrated and selected. Hence, by adjusting the number of rounds of SELEX and/or changing the competitive condition, aptamers with different binding forces, aptamers with different binding modes, and aptamers with the same binding force or binding mode but different base sequences can be obtained in some cases. The SELEX method comprises a process of amplification by PCR; by causing a mutation by using manganese ions and the like in the process, it is possible to perform SELEX with higher diversity.

The aptamers obtained by SELEX are nucleic acids that exhibit high affinity for the target molecule, but this does not mean inhibiting a bioactivity of the target molecule. Chymase is a basic protein to which nucleic acids are thought to be likely to bind non-specifically, but aptamers other than those that bind strongly to a particular site of chymase do not influence the activity of the target molecule. In fact, the RNA comprising a random sequence used as a negative control did not inhibit the enzyme activity of chymase, although it bound to chymase weakly.

Based on an active aptamer thus selected, SELEX can be performed to acquire an aptamer possessing higher activity. Specifically, after preparing a template wherein an aptamer with a determined sequence is partially randomized or a template doped with about 10 to 30% of random sequences, SELEX is performed again.

An aptamer obtained by SELEX has a length of about 80 nucleotides, and this is difficult to prepare as a pharmaceutical as it is. Hence, it is necessary to repeat try-and-error efforts to shorten the aptamer to a length of about 50 nucleotides or less enabling easy chemical synthesis. Depending on the primer design for an aptamer obtained by SELEX, the ease of the subsequent minimization operation changes. Unless the primer is designed successfully, subsequent development will be impossible even if an aptamer with activity is selected by SELEX. In the present invention, an aptamer retaining activity even with 23 nucleotides was obtained.

Aptamers are easily modifiable because they permit chemical synthesis. For aptamers, by predicting the secondary structure using the MFOLD program, or by predicting the steric structure by X-ray analysis or NMR analysis, it is possible to predict to some extent which nucleotide can be substituted or deleted, and where to insert a new nucleotide. A predicted aptamer with the new sequence can easily be chemically synthesized, and it can be determined whether or not the aptamer retains the activity using an existing assay system.

If a region important to the binding of the aptamer obtained with the target molecule is identified by repeated try-and-error efforts as described above, the activity remains unchanged in many cases even when a new sequence is added to both ends of the sequence. The length of the new sequence is not particularly limited.

Those of ordinary skill in the art can make a wide range of design or alterations of modifications, like sequences.

As stated above, aptamers permit a wide range of design or alterations of modifications. The present invention also provides a production method of aptamer that enables a wide range of design or alteration of an aptamer comprising a specified sequence (e.g., a sequence corresponding to a portion selected from among stem regions, internal loop regions, bulge regions, hairpin loop regions and single-strand regions: hereinafter, abbreviated as fixed sequence as required).

For example, the production method of such aptamer includes production of an aptamer comprising a fixed sequence by using a single kind of nucleic acid molecule or a plurality of kinds of nucleic acid molecules (e.g., a library of nucleic acid molecules with different numbers for "a" or "b") consisting of a nucleotide sequence shown by the formula:

| Primer sequence (i) |- (N) a-fixed sequence- (N)b-| Primer sequence (ii) |

[wherein (N)a represents a nucleotide chain consisting of "a" units of N; (N)b represents a nucleotide chain consisting of "b" units of N; each of the units of N, whether identical or different, is a nucleotide selected from the group consisting of A, G, C, U and T (preferably, A, G, C and U). Each of "a" and "b", whether identical or different, can be any numbers, and can be, for example, 1 to about 100, preferably 1 to about 50, more preferably 1 to about 30, still more preferably 1 to about 20 or 1 to about 10], and primer pairs corresponding to the primer sequences (i) and (ii), respectively.

The present invention also provides a complex comprising the aptamer of the present invention and a functional substance bound thereto. The bond between the aptamer and the functional substance in the complex of the present invention can be a covalent bond or a non-covalent bond. The complex of the present invention can be one wherein the aptamer of the present invention and one or more (e.g., 2 or 3) of functional substances of the same kind or different kinds are bound together. The functional substance is not particularly limited, as far as it newly confers a certain function to an aptamer of the present invention, or is capable of changing (e.g., improving) a certain characteristic which an aptamer of the present invention can possess. As examples of the functional substance, proteins, peptides, amino acids, lipids, sugars, monosaccharides, polynucleotides, and nucleotides can be mentioned. As examples of the functional substance, affinity substances (e.g., biotin, streptavidin, polynucleotides possessing affinity for target complementary sequence, antibodies, glutathione Sepharose, histidine), substances for labeling (e.g., fluorescent substances, luminescent substances, radioisotopes), enzymes (e.g., horseradish peroxidase, alkaline phosphatase), drug delivery vehicles (e.g., liposome, microspheres, peptides, polyethyleneglycols), drugs (e.g., those used in missile therapy such as calicheamycin and duocarmycin; nitrogen mustard analogues such as cyclophosphamide, melphalan, ifosfamide or trofosfamide; ethylenimines such as thiotepa; nitrosoureas such as carmustine; alkylating agents such as temozolomide or dacarbazine; folate-like metabolic antagonists such as methotrexate or raltitrexed; purine analogues such as thioguanine, cladribine or fludarabine; pyrimidine analogues such as fluorouracil, tegafur or gemcitabine; vinca alkaloids such as vinblastine, vincristine or vinorelbine and analogues thereof; podophyllotoxin derivatives such as etoposide, taxans, docetaxel or paclitaxel; anthracyclines such as doxorubicin, epirubicin, idarubicin and mitoxantrone, and analogues thereof; other cytotoxic antibiotics such as bleomycin and mitomycin; platinum compounds such as cisplatin, carboplatin and oxaliplatin; pentostatin, miltefosine, estramustine, topotecan, irinotecan and bicalutamide), and toxins (e.g., ricin toxin, liatoxin and Vero toxin) can be mentioned. These functional molecules are finally removed in some cases. Furthermore, the molecules may be peptides that can be recognized and cleaved by enzymes such as thrombin, matrix metalloproteinase (MMP), and Factor X, and may be polynucleotides that can be cleaved by nucleases or restriction endonuclease.

The aptamer or the complex of the present invention can be used as, for example, a pharmaceutical or a diagnostic reagent, a test reagent or a reagents.

The aptamer and complex of the present invention can possess an activity to inhibit a function of chymase. As stated above, chymase is profoundly associated with fibrosis and cardiovascular diseases. Therefore, the aptamer and complex of the present invention are useful as pharmaceuticals for treating or preventing diseases accompanied by fibrosis or cardiovascular disorders.

The aptamer and complex of the present invention are capable of binding specifically to chymase. Therefore, the aptamer and complex of the present invention are useful as probes for chymase detection. The probes are useful in in vivo imaging of chymase, measurements of blood concentrations of chymase, tissue staining, ELISA and the like. The probes are also useful as diagnostic reagents, testing reagents, analytical reagents and the like for diseases involved by chymase (diseases accompanied by fibrosis or cardiovascular disorders, and the like).

Based on their specific binding to chymase, the aptamer and complex of the present invention can be used as ligands for purification of chymase.

The aptamer and complex of the present invention can be used as drug delivery vehicles.

Diseases involved by organ or tissue fibrosis include pulmonary fibrosis, prostatic hyperplasia, myocardial fibrosis, musculoskeletal fibrosis, myelofibrosis, hysteromyoma, scleroderma, adhesion after surgical operations, postoperative scars, burn scars, hypertrophic scars, keloid, atopic dermatitis, peritoneal sclerosis, asthma, liver cirrhosis, chronic pancreatitis, scirrhous gastric cancer, liver fibrosis, renal fibrosis, fibrous vascular diseases, retinitis due to fibrous microvasculitis as a diabetic complication, neurosis, nephropathies, glomerulonephritis, tubulointerstitial nephritis, hereditary renal diseases, arteriosclerotic peripheral arteritis and the like.

Cardiovascular diseases include angiopathies, aortic aneurysms, renal insufficiency, hypertension, arteriosclerosis, myocardial infarction, cardiac hypertrophy, heart failure, restenosis after angiopathies due to percutaneous transluminal coronary angioplasty and the like, diabetic and non-diabetic nephropathies, peripheral circulatory disorders and the like.

Chymase possesses enzyme activity and cleaves bioactive substances that can serve as substrates. Examples of substrates known to date include AngI, latent TGF-$\beta$, SCF, procollagen, procollagenase, pro-MMP-9, IL-1$\beta$ precursor and the like. Chymase exhibits biological actions, via reactions for production or degradation of these bioactive peptides, including extracellular matrix remodeling, networks with cytokines, immunity, and vasoconstriction. Meanwhile, chymase itself acts to activate mast cells and to promote histamine release, and is closely associated with inflammation. Therefore, the aptamer and complex of the present invention are not limited to the above-described substrates, and can be used as pharmaceuticals or diagnostic reagents, testing reagents, and analytical reagents for diseases related to biological functions mediated by substrates accepted by chymase and diseases involved by chymase itself.

The pharmaceutical of the present invention can be one formulated with a pharmaceutically acceptable carrier. As examples of the pharmaceutically acceptable carrier, excipients such as sucrose, starch, mannit, sorbit, lactose, glucose, cellulose, talc, calcium phosphate, and calcium carbonate; binders such as cellulose, methylcellulose, hydroxylpropylcellulose, polypropylpyrrolidone, gelatin, gum arabic, polyethylene glycol, sucrose, and starch; disintegrants such as starch, carboxymethylcellulose, hydroxylpropylstarch, sodium-glycol-starch, sodium hydrogen carbonate, calcium phosphate, and calcium citrate; lubricants such as magnesium stearate, Aerosil, talc, and sodium lauryl sulfate; flavoring agents such as citric acid, menthol, glycyrrhizin-ammonium salt, glycine, and orange powder; preservatives such as sodium benzoate, sodium hydrogen sulfite, methylparaben, and propylparaben; stabilizers such as citric acid, sodium citrate, and acetic acid; suspending agents such as methylcellulose, polyvinylpyrrolidone, and aluminum stearate; dispersing agents such as surfactants; diluents such as water, physiological saline, and orange juice; base waxes such as cacao butter, polyethylene glycol, and kerosene; and the like can be mentioned, but these are not limitative.

There is no limitation on the route of administration of the pharmaceutical of the present invention, which can be administered by, for example, oral administration and parenteral administration.

Preparations suitable for oral administration are a solution prepared by dissolving an effective amount of ligand in a diluent such as water, physiological saline, or orange juice; capsules, sachets or tablets comprising an effective amount of ligand in solid or granular form; a suspension prepared by suspending an effective amount of active ingredient in an appropriate dispersant; an emulsion prepared by dispersing and emulsifying a solution of an effective amount of active ingredient in an appropriate dispersant; C10, which promotes the absorption of water-soluble substances, and the like.

The pharmaceutical of the present invention can be coated by a method known per se for the purpose of taste masking, enteric dissolution, sustained release and the like as required. As examples of coating agents used for the coating, hydroxypropylmethylcellulose, ethylcellulose, hydroxymethylcellulose, hydroxypropylcellulose, polyoxyethylene glycol, Tween 80, Pluronic F68, cellulose acetate phthalate, hydroxypropylmethylcellulose phthalate, hydroxymethylcellulose acetate succinate, Eudragit (manufactured by Rohm, Germany, methacrylic acid/acrylic acid copolymer), pigments (e.g., red iron oxide, titanium dioxide and the like) and the like are used. The pharmaceutical may be a rapid-release preparation or sustained-release preparation.

As preparations suitable for parenteral administration (for example, intravenous administration, subcutaneous administration, intramuscular administration, topical administration, intraperitoneal administration, intranasal administration and the like), aqueous and non-aqueous isotonic sterile injectable liquids are available, which may comprise an antioxidant, a buffer solution, a bacteriostatic agent, an isotonizing agent and the like. Aqueous and non-aqueous sterile suspensions can also be mentioned, which may comprise a suspending agent, a solubilizer, a thickener, a stabilizer, an antiseptic and the like. The preparation can be included in a container such as an ampoule or a vial in a unit dosage volume or in several divided doses. An active ingredient and a pharmaceutically acceptable carrier can also be freeze-dried and stored in a state that may be dissolved or suspended in an appropriate sterile vehicle just before use.

Sustained-release preparations are also suitable preparations. Dosage forms of sustained-release preparations include sustained release from carriers or containers embedded in the body, such as artificial bones, biodegradable bases or non-biodegradable sponges, bags and the like. Devices for continuous or intermittent, systemic or topical delivery from outside the body, such as drug pumps and osmotic pressure pumps, are also included in the scope of sustained-release preparations. Biodegradable bases include liposome, cationic liposome, Poly(lactic-co-glycolic) acid (PLGA), atherocollagen, gelatin, hydroxyapatite, polysaccharide sizofiran.

In addition to liquid injections, suspensions and sustained-release preparations, inhalants suitable for transpulmonary administration, ointments suitable for percutaneous administration, and the like are acceptable.

In the case of an inhalant, an active ingredient in a freeze-dried state is micronized and administered by inhalation using an appropriate inhalation device. An inhalant can be formulated as appropriate with a conventionally used surfactant, oil, seasoning, cyclodextrin or derivative thereof and the like as required. An inhalant can be produced according to a conventional method. Specifically, an inhalant can be produced by powdering or liquefying the aptamer or complex of the present invention, blending it in an inhalation propellant and/or carrier, and filling it in an appropriate inhalation vessel. When the above-described aptamer or complex of the present invention is a powder, an ordinary mechanical powder inhalator can be used; in the case of a liquid, an inhalator such as a nebulizer can be used. Here, as the propellant, conventionally known one can be widely used; chlorofluorocarbon-series compounds such as chlorofluorocarbon-11, chlorofluorocarbon-12, chlorofluorocarbon-21, chlorofluorocarbon-22, chlorofluorocarbon-113, chlorofluorocarbon-114, chlorofluorocarbon-123, chlorofluorocarbon-142c, chlorofluorocarbon-134a, chlorofluorocarbon-227, chlorofluorocarbon-C318, and 1,1,1,2-tetrafluoroethane, hydrocarbons such as propane, isobutane, and n-butane, ethers such as diethyl ether, compressed gases such as gaseous nitrogen and gaseous carbon dioxide and the like can be mentioned.

Here, as examples of the surfactant, oleic acid, lecithin, diethyleneglycol dioleate, tetrahydroflufuryl oleate, ethyl oleate, isopropyl myristate, glyceryl trioleate, glyceryl monolaurate, glyceryl monoleate, glyceryl monostearate, glyceryl monolysinoate, cetyl alcohol, stearyl alcohol, polyethyleneglycol 400, cetylpyridinium chloride, sorbitan trioleate (trade name Span 85), sorbitan monoleate (trade name Span 80), sorbitan monolaurate (trade name Span 20), polyoxyethylene hardened castor oil (trade name HCO-60), polyoxyethylene (20) sorbitan monolaurate (trade name Tween 20), polyoxyethylene (20) sorbitan monoleate (trade name Tween 80), lecithin of natural resource origin (trade name EPICLON), oleylpolyoxyethylene (2) ether (trade name Brij 92), stearyl polyoxyethylene (2) ether (trade name Brij 72), lauryl polyoxyethylene (4) ether (trade name Brij 30), oleylpolyoxyethylene (2) ether (trade name Genapol 0-020), block copolymer of oxyethylene and oxypropylene (trade name Synperonic) and the like can be mentioned. As examples of the oil, corn oil, olive oil, cottonseed oil, sunflower oil and the like can be mentioned. In the case of an ointment, an appropriate pharmaceutically acceptable base (yellow petrolatum, white petrolatum, paraffin, plastibase, silicone, white ointment, beeswax, lard, vegetable oils, hydrophilic ointment, hydrophilic petrolatum, purified lanolin, hydrolyzed lanolin, water-absorbing ointment, hydrophilic plastibase, macrogol ointment and the like) is blended with an aptamer of the present invention, which is the active ingredient, and used as a preparation.

The dosage of the pharmaceutical of the present invention varies depending on the kind and activity of active ingredient, seriousness of disease, animal species being the subject of administration, drug tolerability of the subject of administration, body weight, age and the like, and the usual dosage, based on the amount of active ingredient per day for an adult, can be about 0.0001 to about 100 mg/kg, for example, about 0.0001 to about 10 mg/kg, preferably about 0.005 to about 1 mg/kg.

The present invention also provides a solid phase carrier having the aptamer and/or the complex of the present invention immobilized thereon. As examples of the solid phase carrier, a substrate, a resin, a plate (e.g., multiwell plate), a filter, a cartridge, a column, and a porous material can be mentioned. The substrate can be one used in DNA chips, protein chips and the like; for example, nickel-PTFE (polytetrafluoroethylene) substrates, glass substrates, apatite substrates, silicon substrates, alumina substrates and the like, and substrates prepared by coating these substrates with a polymer and the like can be mentioned. As examples of the resin, agarose particles, silica particles, a copolymer of acrylamide and N,N'-methylenebisacrylamide, polystyrene-crosslinked divinylbenzene particles, particles of dextran crosslinked with epichlorohydrin, cellulose fiber, crosslinked polymers of aryldextran and N,N'-methylenebisacrylamide, monodispersed synthetic polymers, monodispersed hydrophilic polymers, Sepharose, Toyopearl and the like can be mentioned, and also resins prepared by binding various functional groups to these resins were included. The solid phase carrier of the present invention can be useful in, for example, purifying, detecting and quantifying chymase.

The aptamer and/or the complex of the present invention can be immobilized onto a solid phase carrier by a method known per se. For example, a method that introduces an affinity substance (e.g., those described above) or a predetermined functional group into the aptamer and/or the complex of the present invention, and then immobilizing the aptamer or complex onto a solid phase carrier via the affinity substance or predetermined functional group can be mentioned. The present invention also provides such methods. The predetermined functional group can be a functional group that can be subjected to a coupling reaction; for example, an amino group, a thiol group, a hydroxyl group, and a carboxyl group can be mentioned. The present invention also provides an aptamer having such a functional group introduced thereto.

The present invention also provides a method of purifying and concentrating chymase. In particular, the present invention makes it possible to separate chymase from the proteins of other family proteins. The method of purification and concentration of the present invention can comprise adsorbing chymase to the solid phase carrier of the present invention, and eluting the adsorbed chymase with an eluent. Adsorption of chymase to the solid phase carrier of the present invention can be achieved by a method known per se. For example, a chymase-containing sample (e.g., bacterial or cell culture or culture supernatant, blood) is introduced into the solid phase carrier of the present invention or a composition containing the same. Chymase can be eluted using an eluent such as a neutral solution. There is no limitation on the neutral eluent, which can have a pH of, for example, about 6 to about 9, preferably about 6.5 to about 8.5, and more preferably about 7 to about 8. The neutral solution can also comprise, for example, urea, a chelating agent (e.g., EDTA), a sodium salt (e.g., NaCl), a potassium salt (e.g., KCl), a magnesium salt (e.g., $MgCl_2$), a surfactant (e.g., Tween 20, Triton, NP40), and glycerin. The method of purification and concentration of the present invention can further comprise washing the solid phase carrier using a washing solution after chymase adsorption. Examples of the washing solution include those containing urea, a chelating agent (e.g., EDTA), Tris, an acid, an alkali, Transfer RNA, DNA, surfactants such as Tween 20, salts such as NaCl and the like. The method of purification and concentration of the present invention can still further comprise heating the solid phase carrier. This step enables the regeneration and sterilization of the solid phase carrier.

The present invention also provides a method of detecting and quantifying chymase. In particular, the present invention makes it possible to detect and quantify chymase separately from the proteins of other family proteins. The method of detection and quantitation of the present invention can comprise measuring chymase by utilizing the aptamer of the present invention (e.g., by the use of the complex and solid phase carrier of the present invention). The method of detecting and quantifying chymase can be performed in the same manner as an immunological method, except that the aptamer of the present invention is used in place of an antibody.

Therefore, by using the aptamer of the present invention as a probe in place of an antibody, in the same manner as such methods as enzymeimmunoassay (EIA) (e.g., direct competitive ELISA, indirect competitive ELISA, sandwich ELISA), radioimmunoassay (RIA), fluorescent immunoassay (FIA), Western blot technique, immunohistochemical staining method, and cell sorting method, detection and quantitation can be performed. The aptamer of the present invention can also be used as a molecular probe for PET and the like. These methods can be useful in, for example, measuring chymase contents in living organisms or biological samples, and in diagnosing a disease associated with chymase.

The disclosures in all publications mentioned herein, including patents and patent application specifications, are incorporated by reference herein in the present invention to the extent that all of them have been given expressly.

The present invention is hereinafter described in more detail by means of the following Examples, which, however, never limit the scope of the invention.

EXAMPLES

Example 1

Preparation of RNA Aptamers that Bind Specifically to Chymase (1)

RNA aptamers that bind specifically to chymase were prepared using the SELEX method. SELEX was performed with improvements of the method of Ellington et al. (Ellington and Szostak, Nature 346, 818-822, 1990) and the method of Tuerk et al. (Tuerk and Gold, Science 249, 505-510, 1990). Chymase (Human Skin, manufactured by Calbiochem) immobilized on NHS-activated Sepharose 4 Fast Flow (manufactured by GE Healthcare) carrier was used as a target molecule. Chymase immobilization to the carrier was performed as directed in the specifications by GE Healthcare. The amount immobilized was confirmed by examining the chymase solution before immobilization and the supernatant just after immobilization by SDS-PAGE. As a result of the SDS-PAGE, no band of chymase was detected in the supernatant; it was confirmed that nearly all of the chymase used had been coupled. This means that about 167 pmol of chymase was immobilized to about 3 µL of the resin.

The RNA used in the first round (40N) was obtained by transcribing a chemically synthesized DNA using the DuraScribe™ T7 Transcription Kit (manufactured by Epicentre). The RNA obtained by this method has the 2'-position of ribose of the pyrimidine nucleotide fluoro-substituted. The following DNA of 70 nucleotides long, having a primer sequence at each end of a 40-nucleotide random sequence, was used as a DNA template. The DNA template and primers used were prepared by chemical synthesis.

```
DNA template:
                                                    (SEQ ID NO: 1)
5'-
GCGGCCGCTCTTCTATGNNNNNNNNNNNNNNNNNNNNNNNNNNNNNNNNNNNNNNNNGAATT
CCTACCGT-3'

Primer Fwd:
                                                    (SEQ ID NO: 2)
5'-TAATACGACTCACTATAGGGACGGTAGGAATTC-3'

Primer Rev:
                                                    (SEQ ID NO: 3)
5'-GCGGCCGCTCTTCTATG-3'
```

The sequential Ns in the DNA template (SEQ ID NO: 1) are 40 nucleotides in any combinations (40N: each N is A, G, C or T), producing a sequence region unique to each aptamer obtained. The primer Fwd comprises a promoter sequence of T7 RNA polymerase. The variation of the RNA pool used in the first round was theoretically $10^{14}$.

The RNA pool was added to the chymase-immobilized carrier, and allowed to stand at room temperature for 30 minutes. Then, to remove the RNA not bound to chymase, the resin was washed with solution A. Here, the solution A was a mixed solution of 145 mM sodium chloride, 5.4 mM potassium chloride, 1.8 mM calcium chloride, 0.8 mM magnesium chloride, and 20 mM Tris. The RNA bound to chymase was heated at 95° C. for 10 minutes with the addition of solution B as an eluent, and recovered from the supernatant. Here, the solution B was a mixture of 7M Urea, 3 mM EDTA, and 100 mM Tris-HCl (pH 6.6). The recovered RNA was amplified by RT-PCR and transcribed using the DuraScribe™ T7 Transcription Kit, and this was used as the pool for the next round. With this procedure taken as 1 round, the same operation was performed plural times. After completion of SELEX, the PCR product was cloned into pGEM-T Easy vector (manufactured by Promega), and the *Escherichia coli* strain DH5α (manufactured by Toyobo) was transformed therewith. After the plasmid was extracted from a single colony, the base sequences of clones were determined using a DNA sequencer (3130xl Genetic Analyzer, manufactured by ABI).

Figure 1:
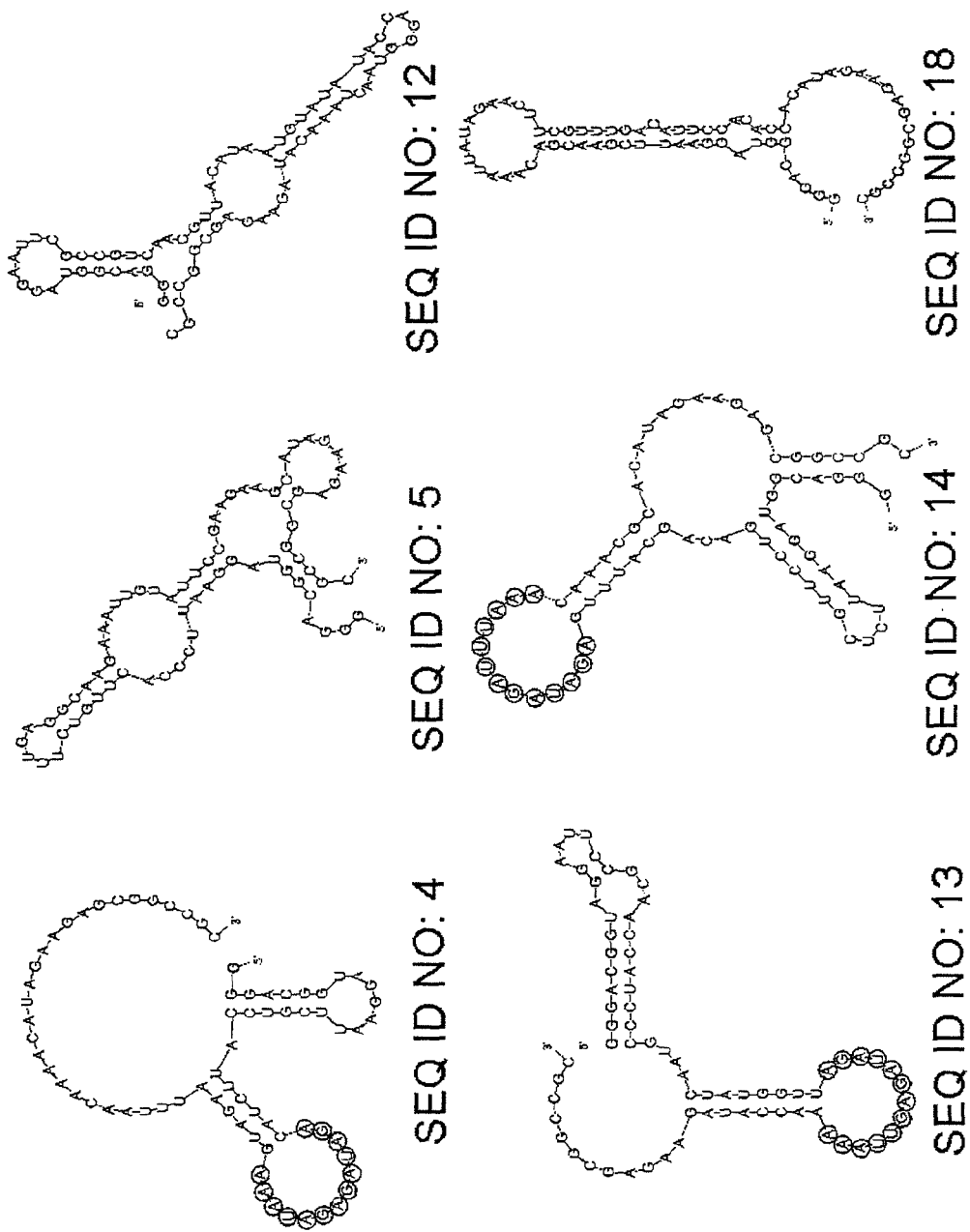
FIG. 1 shows the secondary structure of aptamer shown by SEQ ID NO: 4, 5, 12-14, 18 predicted by the MFOLD program, wherein the part enclosed in a circle shows a common sequence shown by SEQ ID NO: 21.

After 8 rounds of SELEX, the sequences of 44 clones were sequenced; sequence convergence was seen. The sequences of some of the clones are shown by SEQ ID NO: 4-20. Among the sequences, there existed 6 sequences shown by SEQ ID NO: 4, 2 sequences shown by SEQ ID NO: 5, and 1 sequence shown by SEQ ID NO: 6-20. SEQ ID NO: 6 and 8 differed only by one base. The sequences of SEQ ID NO: 4, 13, and 14 were found to contain the common sequence shown by SEQ ID NO: 21, which was present in 9 of the 44 clones. The secondary structures of these sequences were predicted using the MFOLD program (M. Zuker, Nucleic Acids Res. 31(13), 3406-3415, 2003); the portions formed by the common sequence portion had a similar loop structure. Putative secondary structures of the aptamers of the sequences shown by SEQ ID NO: 4, 5, 12-14, and 18 are given in FIG. 1, wherein each portion formed by the common sequence shown by SEQ ID NO: 21 is enclosed in a circle.

Given below are the respective nucleotide sequences. Unless otherwise stated, the following individual sequences are shown in the direction from 5' to 3', with the purine bases (A and G) being in the 2'-OH form, and the pyrimidine bases (U and C) in the 2'-fluoro-modified form. In the sequences, each of $N_1$ and $N_2$ indicates any nucleotides out of A, G, C, and U, and $X_1$ and $X_2$ are both A or both G.

```
SEQ ID NO: 4:
GGGACGGUAGGAAUUCGUCCAUUCUACAGAUAGAGAUAAAGUAGAAUUUAACAAAACAUAGA
AGAGCGGCCGC

SEQ ID NO: 5:
GGGACGGUAGGAAUUCCCACUUGUCUUUGAGGCAAGAAAUUGUAUUCCGAAGAAGCAUAGAA
GAGCGGCCGC

SEQ ID NO: 6:
GGGACGGUAGGAAUUCUACGGUCUGUGUGAAAUUGAAACACACAAAGAACAAUAGACAUAGA
AGAGCGGCCGC

SEQ ID NO: 7:
GGGACGGUAGGAAUUCACCUUUCCAAUUGUGAAAGAAACACAAAAAGAAAUGACAUCAUAGA
AGAGCGGCCGC

SEQ ID NO: 8:
GGGACGGUAGGAAUUCUACGGUCUGUGUGAAAUUGAAACACACAAAGAACAAUAAACAUAGA
AGAGCGGCCGC

SEQ ID NO: 9:
GGGACGGUAGGAAUUCCCGAAAAGCAACAAGCUUGCUAAAAUGAUUCCGAAAAAACACAUAG
AAGAGCGGCCGC

SEQ ID NO: 10:
GGGACGGUAGGAAUUCCGCCGCCUAAAAAACGACGAUAUUACAGAAACGUCAAAUACAUAGA
AGAGCGGCCGC

SEQ ID NO: 11:
GGGACGGUAGGAAUUCCCGACACGAAAUGUGUGAUUAAUUCCGAACAACAAAGUAACAUAGA
AGAGCGGCCGC

SEQ ID NO: 12:
GGGACGGUAGGAAUUCGCCGUCAACGUUACAUAAUGUAUAUACCAGGGUAACUAAACAUAGA
AGAGCGGCCGC

SEQ ID NO: 13:
GGGACGGUAGGAAUUCCGCAACCAUCCCGUAACUAUGGUUAGAUAGAGUUAAAAACCAUAGA
AGAGCGGCCGC

SEQ ID NO: 14:
GGGACGGUAGGAAUUCUCGUUCCUGACAGCAUUUGAGAUAGAUUUAAACAAACGCACAUAGA
AGAGCGGCCGC

SEQ ID NO: 15:
GGGACGGUAGGAAUUCCCAGAAAAUAAAUUCCGAAGAAAACAACAAUUUUUGCAAACAUAGA
AGAGCGGCCGC

SEQ ID NO: 16:
GGGACGGUAGGAAUUCCCAUGACUGAAAAACGUCAGUAAAAUCCGAAAAUCAUAUCAUAGAA
GAGCGGCCGC

SEQ ID NO: 17:
GGGACGGUAGGAAUUCCGUUCGCAGAAACGAACUUUUAAAAAAUGUACGUGGGAGCACAUAG
AAGAGCGGCCGC

SEQ ID NO: 18:
GGGACGGUAGGAAUUCGAACGACAAAUUAUAGAACUUCGUUUGACAUUCCACACCACAUAGA
AGAGCGGCCGC

SEQ ID NO: 19:
GGGACGGUAGGAAUUCCCACUGCAAUUCAGCAGAAAAAAUUCCGAAAAACACACACCAUAGA
AGAGCGGCCGC

SEQ ID NO: 20:
GGGACGGUAGGAAUUCAAAAUCAGCUGAUUUGUAAUUUUUUUACACAGGCAAAACACAUAGA
AGAGCGGCCGC

SEQ ID NO: 21:
X₁GAUAGAN₁N₂UAAX₂
```

Figure 2:
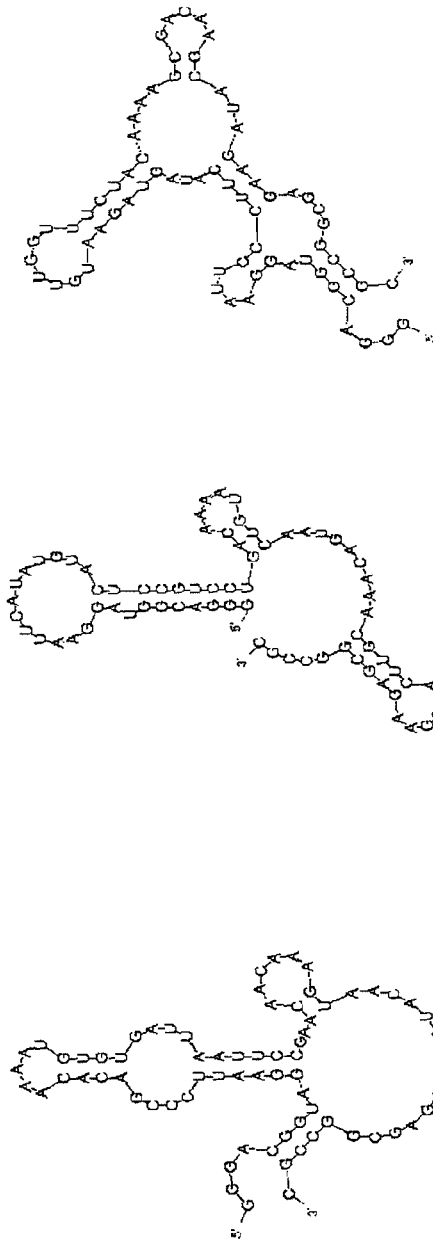
FIG. 2 shows the secondary structure of aptamer shown by SEQ ID NO: 22-27 predicted by the MFOLD program, wherein the part enclosed in a circle shows a common sequence shown by SEQ ID NO: 21.
Figure 2:
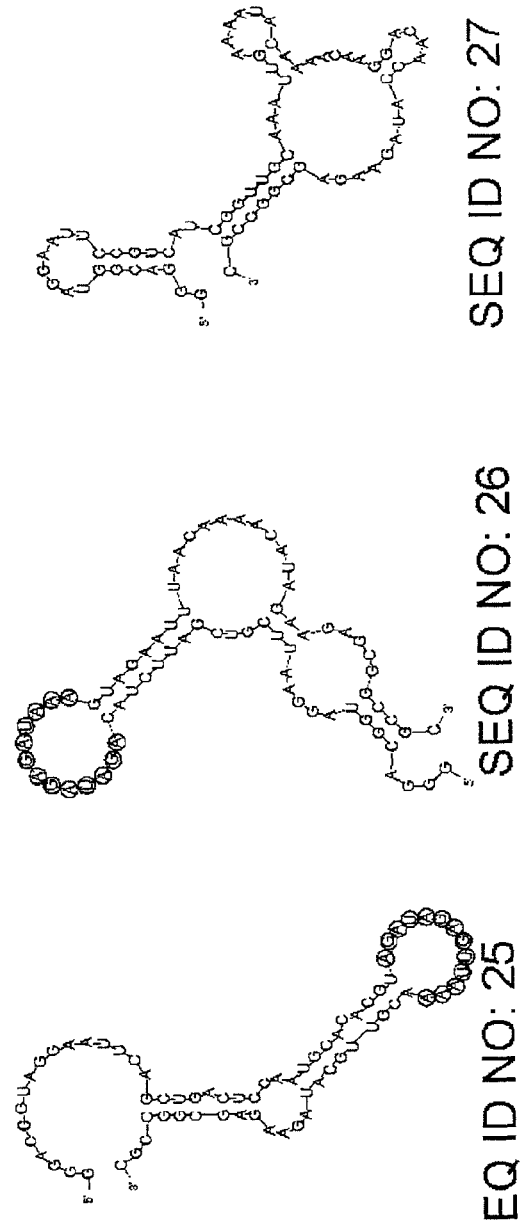

After the above-described 8 rounds, SELEX was continued under the similar conditions. After completion of the 11th round, the sequences of 93 clones were sequenced. Some of the sequences of the clones are shown by SEQ ID NO: 22-27. A number of sequences were identical to some of the sequences obtained after the 8 rounds; there existed 22 sequences shown by SEQ ID NO: 4 and 4 sequences shown by SEQ ID NO: 14. This means that the common sequence shown by SEQ ID NO: 21 was concentrated. There also existed 1 sequence shown by SEQ ID NO: 5, 3 sequences shown by SEQ ID NO: 22, and 2 sequences shown by SEQ ID NO: 23 and 24. One sequence was shown by SEQ ID NO: 25-27. SEQ ID NO: 22 and 11 differed only by one base. SEQ ID NO: 26 and 4 differed only by one base. The common sequence shown by SEQ ID NO: 21 was present in 35 of the 93 clones. Of the sequences that newly emerged by the 11th round, those shown by SEQ ID NO: 25 and 26 contained the common sequence shown by SEQ ID NO: 21. Putative secondary structures of the aptamers of the sequences shown by SEQ ID NO: 22-27 are given in FIG. 2, wherein each portion formed by the common sequence shown by SEQ ID NO: 21 is enclosed in a circle. All these portions had a characteristic loop structure, as in FIG. 1.

Given below are the respective nucleotide sequences. Unless otherwise stated, the following individual sequences are shown in the direction from 5' to 3', with the purine bases (A and G) being in the 2'-OH form, and the pyrimidine bases (U and C) in the 2'-fluoro-modified form.

before immobilization and the supernatant just after immobilization by SDS-PAGE. The results of the SDS-PAGE detected no chymase band in the supernatant, confirming that almost all of the chymase used was immobilized. It was evident that about 100 pmol of chymase was immobilized to about 3 µL of the resin.

Figure 3:
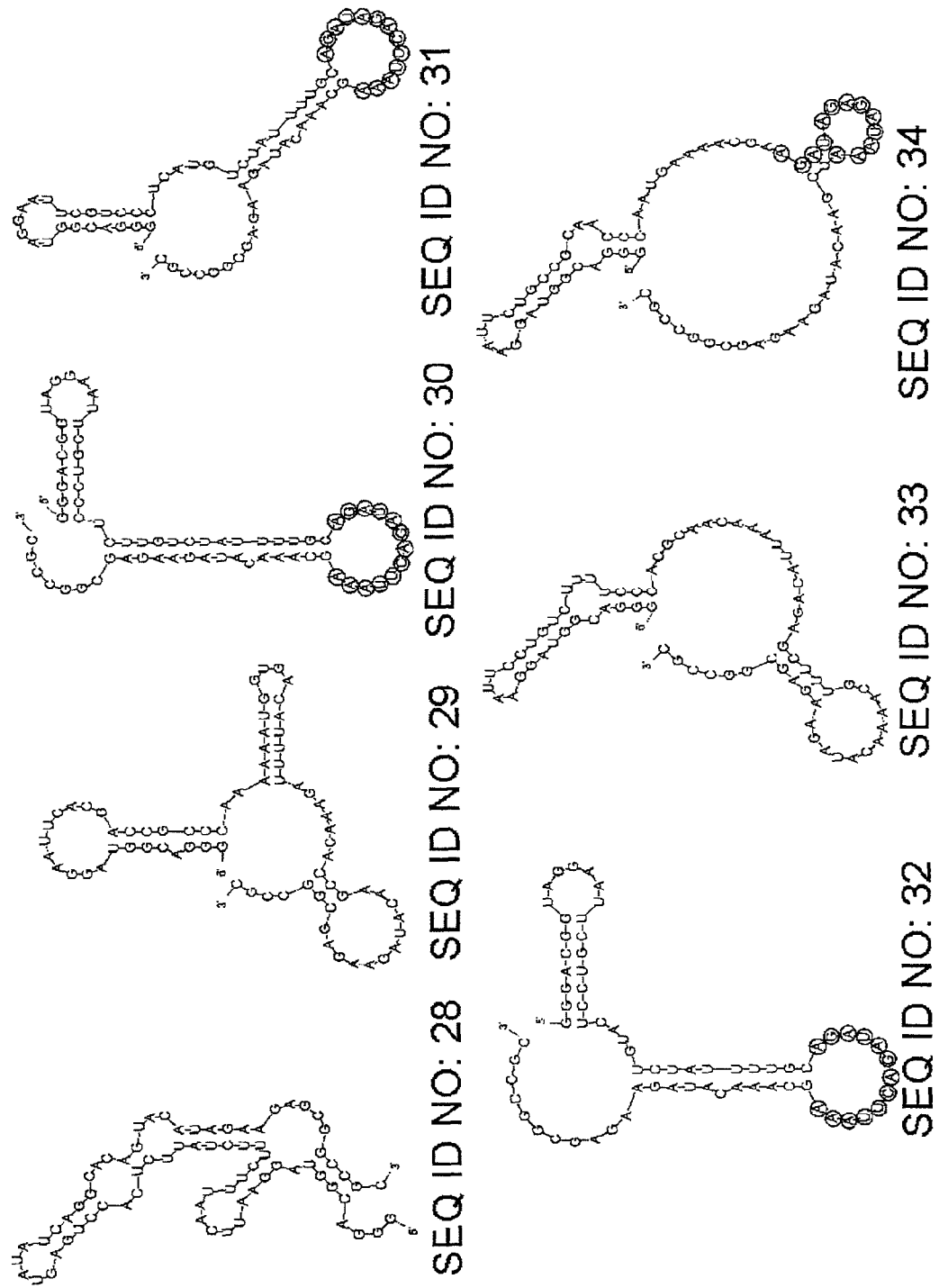
FIG. 3 shows the secondary structure of aptamer shown by SEQ ID NO: 28-34 predicted by the MFOLD program, wherein the part enclosed in a circle shows a common sequence shown by SEQ ID NO: 21.

The pool at the 11th round was cloned, and the sequences of 79 clones were determined. The sequences of some of these clones are shown by SEQ ID NO: 28-34. There were a number of sequences identical to the sequences obtained after the above-described 8 rounds; there existed 9 sequences shown by SEQ ID NO: 4 and 1 sequence shown by SEQ ID NO: 19. There were a number of sequences identical to the sequences obtained after the above-described 11 rounds; there existed 2 sequences shown by SEQ ID NO: 27. Additionally, there existed 4 sequences shown by SEQ ID NO: 28, 2 sequences shown by SEQ ID NO: 29, and 1 sequence shown by SEQ ID NO: 30-34. SEQ ID NO: 30 and 31 differed only by one base. SEQ ID NO: 32 is a sequence resulting from deletion of one base from SEQ ID NO: 31. The common sequence shown by SEQ ID NO: 21 was present in 14 of the 79 clones. Of the sequences that newly emerged by the 11th round, those of SEQ ID NO: 30-32 and 34 were found to comprise the common sequence shown by SEQ ID NO: 21. Putative secondary structures of the aptamers of the sequences shown by SEQ ID NO: 28-34 are given in FIG. 3, wherein each portion formed by the common sequence shown by SEQ ID NO: 21 is

```
SEQ ID NO: 22:
GGGACGGUAGGAAUUCCCGACACAAAAUGUGUGAUUAAUUCCGAACAACAAAGUAACAUAGA
AGAGCGGCCGC

SEQ ID NO: 23:
GGGACGGUAGGAAUUCAUAUGUACUCCGUCCUGACAAAAUGUCAAUGACAAACGUUCAUAGA
AGAGCGGCCGC

SEQ ID NO: 24:
GGGACGGUAGGAAUUCCCUUCAUAGUAGAAUGUUGGUUUCUACAAAAGCGACAAGCAUAGAA
GAGCGGCCGC

SEQ ID NO: 25:
GGGACGGUAGGAAUUCAGCUGACUCCAAUGCACACGUAGAUAGAGUUAAAACGUUGCAUAGA
AGAGCGGCCGC

SEQ ID NO: 26:
GGGACGGUAGGAAUUCGUCGAUUCUACAGAUAGAGAUAAAGUAGAAUUUAACAAAACAUAGA
AGAGCGGCCGC

SEQ ID NO: 27:
GGGACGGUAGGAAUUCCGUCAUCGGUUGCAAAUUGAAAAUACAAAACAAGGACAACCAUAGA
AGAGCGGCCGC
```

After the above-described 8 rounds of SELEX, SELEX was continued using chymase (Human Skin, manufactured by Calbiochem), immobilized on Heparin Sepharose 6 Fast Flow (manufactured by GE Healthcare) carrier, as a target molecule. The chymase in solution was added to the carrier and retained at room temperature for 30 minutes, whereby the chymase was immobilized to the carrier. The amount immobilized was checked by examining the chymase solution enclosed in a circle. All these portions, except for the clone shown by SEQ ID NO: 34, had a characteristic loop structure, as in FIG. 1.

Given below are the nucleotide sequences shown by SEQ ID NO: 28-34, respectively. Unless otherwise stated, the following individual sequences are shown in the direction from 5' to 3', with the purine bases (A and G) being in the 2'-OH form, and the pyrimidine bases (U and C) in the 2'-fluoro-modified form.

```
SEQ ID NO: 28:
GGGACGGUAGGAAUUCAAUUUCUUUCUAUUCUCACCUGAGUAUAUCAGGCACAGUACAUAGA
AGAGCGGCCGC

SEQ ID NO: 29:
GGGACGGUAGGAAUUCACGACCGCCCAAAAAAUGGUGACAUUUUAGAAACACCGAACAUAGA
AGAGCGGCCGC
```

```
SEQ ID NO: 30:
GGGACGGUAGGAAUUCGUCCCUCUUGUCUAUUUUGCAGAUAGACUUAAAGCAAACAUAGAAG
AGCGGCCGC

SEQ ID NO: 31:
GGGACGGUAGGAAUUCGUCCCUCAUGUCUAUUUUGCAGAUAGACUUAAAGCAAACAUAGAAG
AGCGGCCGC

SEQ ID NO: 32:
GGGACGGUAGGAAUUCGUCCUCAUGUCUAUUUUGCAGAUAGACUUAAAGCAAACAUAGAAGA
GCGGCCGC

SEQ ID NO: 33:
CGGACGGUAGGAAUUCCUGUCUUUUCCCACGCAACAAAUUACAGAGCUUUGCAAAACAUAGA
AGAGCGGCCGC

SEQ ID NO: 34:
GGGACGGUAGGAAUUCUGCCGCAACCCAAUGAAAACGAAGAUAGAGAUAAAUCGAACAUAGA
AGAGCGGCCGC
```

The binding activities against chymase of the nucleic acids shown by SEQ ID NO: 4-20 and 22-34 were determined by the surface plasmon resonance method using Biacore T100 (manufactured by GE Healthcare). The sensor chip used was the SA chip, which had streptavidin immobilized thereon. Bound thereto was about 1500 RU of a 16-nucleotide Poly dT with biotin bound to the 5' end thereof. The ligand nucleic acid had a 16-nucleotide Poly A added to the 3' end thereof, and was immobilized to the SA chip by annealing between T and A. 20 μL of each nucleic acid was injected at a flow rate of 20 μL/min, and about 1000 RU nucleic acid was immobilized. 20 μL of chymase for analyte, prepared at 0.2 μM, was injected. Solution A was used as a running buffer.

All sequences examined were found to bind to chymase (Table 1). However, the nucleic acid pool (40N) used at the 1st round, which contained a random sequence of 40 nucleotides serving as a negative control, was also found to exhibit weak binding activity against chymase. Hence, in Table 1, aptamers with higher binding activity than 40N are represented by ++, and those with equivalent binding activity compared with 40N are represented by +. A sensorgram showing how the aptamers shown by SEQ ID NO: 12 and 13 bound to chymase is given in FIG. 4.

Irrespective of whether the common sequence shown by SEQ ID NO: 21 was present or absent, some sequences exhibited higher binding activity than 40N, and others exhibited equivalent binding activity compared with 40N. SEQ ID NO: 4, 13, 14, 25, 26, and 30, which comprise this common sequence, exhibited higher binding activity than 40N, whereas SEQ ID NO: 31, 32, and 34, which comprise the same common sequence, exhibited equivalent binding activity compared with 40N. It was found that the $N_1N_2$ contained in the sequence of SEQ ID NO: 21 may be GA, GU, UU, or CU, and that the $X_1$ and $X_2$ contained in the sequence of SEQ ID NO: 21 may be both A.

TABLE 1

Binding activity for chymase.

| SEQ ID NO: | Length | Binding activity as determined using Biacore |
|---|---|---|
| 4 | 73 | ++ |
| 5 | 72 | ++ |
| 6 | 73 | ++ |
| 7 | 73 | ++ |
| 8 | 73 | ++ |
| 9 | 74 | ++ |
| 10 | 73 | ++ |
| 11 | 73 | ++ |
| 12 | 73 | ++ |
| 13 | 73 | ++ |
| 14 | 73 | ++ |
| 15 | 73 | ++ |
| 16 | 72 | ++ |
| 17 | 74 | ++ |
| 18 | 73 | ++ |
| 19 | 73 | ++ |
| 20 | 73 | + |
| 22 | 73 | + |
| 23 | 73 | ++ |
| 24 | 72 | ++ |
| 25 | 73 | ++ |
| 26 | 73 | ++ |
| 27 | 73 | ++ |
| 28 | 73 | + |
| 29 | 73 | ++ |
| 30 | 71 | ++ |
| 31 | 71 | + |
| 32 | 70 | + |
| 33 | 73 | + |
| 34 | 73 | + |

"++" represents a sequence that binds to chymase significantly more strongly than the negative control 40N. "+" represents a sequence that binds to chymase equivalently compared with the negative control 40N. Here, 40N represents the nucleic acid pool used in the 1st round, which comprises a random sequence of 40 nucleotides.

Example 2

Preparation of RNA Aptamers that Bind Specifically to Chymase (2)

SELEX was performed in the same manner as Example 1, but using a template whose random sequence was of 30 nucleotides, and a primer sequence different from that used in Example 1. The target molecule used in the SELEX was chymase (recombinant, manufactured by SIGMA), immobilized on NHS-activated Sepharose 4 Fast Flow (manufactured by GE Healthcare) carrier. The sequences of the template and primers used are shown below. The DNA template and primers were chemically synthesized.

DNA template:
(SEQ ID NO: 35)
5'-TCACACTAGCACGCATAGGNNNNNNNNNNNNNNNNNNNNNNNNNNNNNNCATCTGACCTCTCTCCTGCTCCC-3'

Primer Fwd:
(SEQ ID NO: 36)
5'-TAATACGACTCACTATAGGGAGCAGGAGAGAGGTCAGATG-3'

Primer Rev:
(SEQ ID NO: 37)
5'-TCACACTAGCACGCATAGG-3'

The sequential Ns in the DNA template (SEQ ID NO: 35) are 30 nucleotides in any combinations (30N: each N is A, G, C or T), producing a sequence region unique to each aptamer obtained. The Primer Fwd comprises a promoter sequence of T7 RNA polymerase. The variation of the RNA pool used in the first round was theoretically $10^{14}$.

The RNA pool was added to the carrier with chymase immobilized thereon, and retained at room temperature for 30 minutes, after which the resin was washed with solution C to eliminate the RNA not bound to the chymase. Here, the solution C was a mixed solution of 145 mM sodium chloride, 5.4 mM potassium chloride, 1.8 mM calcium chloride, 0.8 mM magnesium chloride, 20 mM Tris (pH 7.6), and 0.05% Tween 20. The RNA bound to the chymase was recovered by adding solution D as an eluent, and stirring the mixture at room temperature for 10 minutes. Here, the solution D was prepared by adding 6M guanidine hydrochloride to the solution C to obtain a pH of 7.6. Elution was performed in 3 cycles. The RNA recovered was amplified by RT-PCR, and transferred using the DuraScribe™ T7 Transcription Kit for use as a pool in the next round. Each round of these steps was repeated a plurality of times. After completion of SELEX, the PCR product was cloned into the pGEM-Easy vector (manufactured by Promega), and *Escherichia coli* strain DH5α (manufactured by Toyobo) was transformed therewith. After the plasmid was extracted from a single colony, the clones were sequenced using a DNA sequencer (3130×1 Genetic Analyzer, manufactured by ABI).

After completion of 8 rounds of SELEX, the sequences were determined; sequence convergence was not seen. Hence, 2 mg/mL heparin as a competing agent was added, and SELEX was continued to the 11th round. The sequences of 40 clones were determined, and convergence was seen; the sequences of all the 40 clones were found to contain the common sequence shown by SEQ ID NO: 21. The sequences of some of these clones are shown by SEQ ID NO: 38-48. There existed 6 sequences shown by SEQ ID NO: 38, 2 sequences shown by SEQ ID NO: 39, and 1 sequence shown by SEQ ID NO: 40-48.

Putative secondary structures of the aptamers of the sequences shown by SEQ ID NO: 38-40, 43, and 48 are given in FIG. 5, wherein each portion formed by the common sequence shown by SEQ ID NO: 21 is enclosed in a circle. In many of these portions, the common sequence shown by SEQ ID NO: 21 formed a characteristic loop structure similar to that shown in FIG. 1.

Given below are the nucleotide sequences shown by SEQ ID NO: 38-48, respectively. Unless otherwise stated, the following individual sequences are shown in the direction from 5' to 3', with the purine bases (A and G) being in the 2'-OH form, and the pyrimidine bases (U and C) in the 2'-fluoro-modified form.

SEQ ID NO: 38:
GGGAGGAGGAGAGAGGUCAGAUGGAUAGAGUUAAGAUCUGGCUGGCGCAUUAGCCUAUGCGUGCUAGUGUGA

SEQ ID NO: 39:
GGGAGCAGGAGAGAGGUCAGAUGGUUACGGAUAGAGUUAAGGUAACGGUACGGCCUAUGCGUGCUAGUGUGA

SEQ ID NO: 40:
GGGAGCAGGAGAGAGGUCAGAUGAACGGAUAGAGCUAAGAGUUCGUCAGAGGGGCCUAUGCGUGCUAGUGUGA

SEQ ID NO: 41:
GGGAGCAGGAGAGAGGUCAGAUGGUGAGAUAGAGUUAAACACCACAAUAGUAGCCUAUGCGUGCUAGUGUGA

SEQ ID NO: 42:
GGGAGCAGGAGAGAGGUCAGAUGCGUGAUCGUGCAAGGCGGAUAGAGUUAAGGCCUAUGCGUGCUAGUGUGA

SEQ ID NO: 43:
GGGAGCAGGAGAGAGGUCAGAUGAUGCCAAGAUAGAUUUAAAUGGCGUUUGGGCCUAUGCGUGCUAGUGUGA

SEQ ID NO: 44:
GGGAGCAGGAGAGAGGUCAGAUGUUAGACCAAAGCAUAGGAGAUAGAGUUAAACCUAUGCGUGCUAGUGUGA

SEQ ID NO: 45:
GGGAGCAGGAGAGAGGUCAGAUGGACCACCGAUGGGCAAGAUAGAGUUAAAUGCCUAUGCGUGCUAGUGUGA

-continued

SEQ ID NO: 46:
GGGAGCAGGAGAGAGGUCAGAUGGGACAGAUAGAGUUAAAGUCCGUUACGUGGCCUAUGCGU
GCUAGUGUGA

SEQ ID NO: 47:
GGGAGCAGGAGAGAGGUCAGAUGGUGAUAGAUAGAGUUAAAAUCGCUGAAUGGCCUAUGCGU
GCUAGUGUGA

SEQ ID NO: 48:
GGGAGGAGGAGAGAGGUCAGAUGUGAAGAUAGAGAUAAAUCACAUACAGUCGGCCUAUGCGU
GCUAGUGUGA

The binding activities against chymase of the nucleic acids shown by SEQ ID NO: 38-48 were evaluated by the surface plasmon resonance method. In the evaluations for SEQ ID NO: 38-48, measurements were taken in the same manner as Example 1. Solution C was used as a running buffer. The results of the measurements are shown in Table 2.

The nucleic acids shown by SEQ ID NO: 38-48 were identified as aptamers that bind to chymase significantly more potently than 30N. It was found that the $X_1$ and $X_2$ contained in the common sequence SEQ ID NO: 21 may be both A or both G, and that the $N_1N_2$ contained in the common sequence may be GU, GC, GA, or UU.

TABLE 2

Binding activity for chymase.

| SEQ ID NO: | Length | Binding activity as determined using Biacore |
|---|---|---|
| 38 | 72 | ++ |
| 39 | 72 | ++ |
| 40 | 73 | ++ |
| 41 | 72 | ++ |
| 42 | 72 | ++ |
| 43 | 72 | ++ |
| 44 | 72 | ++ |
| 45 | 72 | ++ |
| 46 | 72 | ++ |
| 47 | 72 | ++ |
| 48 | 72 | ++ |

"++" indicates a sequence that binds to chymase significantly more strongly than the negative control 30N. Here, 30N represents the nucleic acid pool used in the 1st round, which comprises a random sequence of 30 nucleotides.

Example 3

Determination of Chymase Inhibitory Activity Using Synthetic Substrate

Whether the nucleic acids shown by SEQ ID NO: 4-20, 22-34, and 38-48 inhibit the enzyme activity of chymase was determined as described below. The chymase substrate used was Suc-Ala-Ala-Pro-Phe-MCA (manufactured by Peptide Institute, Inc.), which contains the 4-amino-acid peptide Ala-Ala-Pro-Phe, a standard substrate for chymotrypsin-like proteases. Here, Suc is a protecting succinyl group, and MCA is a 4-methylcoumaryl-7-amide group; upon cleavage of the C-terminal side of phenylalanine, AMC (7-amino-4-methyl-coumarine) is released. By detecting the fluorescence of this AMC, the enzyme activity of chymase can be determined. The assay was performed using a 96-well plate (F16 Black Maxisorp Fluoronunc, manufactured by Nunc), with a reaction mixture volume of 100 μL, in solution C as a buffer solution. First, each nucleic acid was serially diluted to 0.0027-2 μM concentrations in solution C to obtain 50 μL solutions. After 10 μL of the 1 mM substrate prepared in solution C was added thereto, the plate was set to the microplate reader SpectraMax190 (manufactured by Molecular Devices Corporation), and incubated at 37° C. for 5 minutes. Separately, 0.05 μg (or 0.005 μg) of chymase (recombinant, manufactured by SIGMA) was diluted in solution C to obtain a 40 μL chymase solution, and incubated at 37° C. for 5 minutes. The chymase solution was added to the mixture of the nucleic acid and substrate to initiate an enzyme reaction. The final chymase concentration in the reaction mixture was 16.7 nM (or 1.67 nM), the final substrate concentration being 100 μM. The plate containing the reaction mixture was set to the microplate reader SpectraMax190 (manufactured by Molecular Devices Corporation), and examined for time-dependent changes in the fluorescence intensity at 37° C. for 5 minutes (or 30 minutes) (excitation wavelength 380 nm, detection wavelength 460 nm). A linear approximation of the increase in the fluorescence of the AMC released from the substrate by chymase activity was generated, and its slope was taken as the initial velocity ($V_{max}$). For control, samples were treated and analyzed in the same manner in two cases: use of a 30N or 40N (a nucleotide of 30 or 40 consecutive bases represented by N; N is A, G, C or T) nucleic acid pool (negative control), and use of chymostatin, a known chymotrypsin-like serine protease inhibitor (positive control). Taking the initial reaction velocity without the nucleic acid and inhibitor ($V_0$) as a 100% enzyme activity, the inhibitory rate of each test substance was calculated using the following equation:

Inhibitory rate (%)=$(1-V_{max}/V_0) \times 100$

The inhibitor concentration required to cause a 50% inhibition of the enzyme activity ($IC_{50}$) was determined. The results are shown in Table 3.

TABLE 3

Inhibitory activity against chymase ($IC_{50}$).

| SEQ ID NO: | $IC_{50}$ [μM] |
|---|---|
| 4 | 0.049 ± 0.003 |
| 5 | 0.080 ± 0.039 |
| 6 | 0.456 ± 0.261 |
| 7 | >0.5 |
| 8 | 0.453 ± 0.463 |
| 9 | 0.273 ± 0.069 |
| 10 | >0.5 |
| 11 | 0.145 ± 0.036 |
| 12 | 0.128 ± 0.023 |
| 13 | 0.058 ± 0.024 |
| 14 | 0.061 ± 0.053 |
| 15 | 0.285 ± 0.021 |
| 16 | >0.5 |
| 17 | 0.092 ± 0.042 |
| 18 | 0.058 ± 0.021 |
| 19 | 0.163 ± 0.001 |
| 20 | 0.282 ± 0.013 |
| 22 | 0.105 ± 0.009 |
| 23 | 0.238 ± 0.060 |
| 24 | 0.092 ± 0.003 |

TABLE 3-continued

Inhibitory activity against chymase ($IC_{50}$).

| SEQ ID NO: | $IC_{50}$ [µM] |
|---|---|
| 25 | 0.079 ± 0.028 |
| 26 | 0.106 ± 0.004 |
| 27 | >0.5 |
| 28 | 0.045 ± 0.004 |
| 29 | >0.5 |
| 30 | 0.147 ± 0.044 |
| 31 | 0.155 ± 0.039 |
| 32 | 0.235 ± 0.055 |
| 33 | 0.145 ± 0.088 |
| 34 | 0.137 ± 0.009 |
| 38 | 0.050 ± 0.012 |
| 40 | 0.140 ± 0.085 |
| 41 | 0.060 ± 0.017 |
| 42 | 0.124 ± 0.026 |
| 43 | 0.081 ± 0.050 |
| 44 | 0.049 ± 0.013 |
| 45 | 0.074 ± 0.011 |
| 46 | 0.038 ± 0.004 |
| 47 | 0.058 ± 0.012 |
| 48 | 0.095 ± 0.018 |

">0.5" indicates that no inhibitory activity was observed in the concentration range up to 0.5 µM. Each $IC_{50}$ value is a mean value for 2 to 3 measurements.

The negative control 30N or 40N did not exhibit inhibitory activity ($IC_{50}$>0.5 µM). The positive control chymostatin exhibited $IC_{50}$ values of 0.1 µM-0.2 µM.

In summary, many of the aptamers listed in Table 3 exhibited inhibitory activity against chymase. The aptamers exhibiting $IC_{50}$ values of 0.1 µM or less, in particular, can be judged to have an excellent inhibitory effect. The aptamers comprising the common sequence shown by SEQ ID NO: 21 all exhibited inhibitory activity. These findings demonstrate that the $X_1$ and $X_2$ contained in the common sequence may be both A or both G, and that the $N_1 N_2$ may be any of GA, GU, GC, UU, and CU.

Example 4

Truncation of Aptamer

The aptamers shown by SEQ ID NO: 4, 12, 13, and 14 were shortened. The aptamers shown by SEQ ID NO: 4, 13, and 14 comprise the common sequence shown by SEQ ID NO: 21. SEQ ID NO: 12 is an aptamer that does not comprise this common sequence. The sequences of shortened aptamers are shown in SEQ ID NO: 49-57. Putative secondary structures of the aptamers shown by SEQ ID NO: 49, 51, and 55-57 are given in FIG. 6, wherein each portion formed by the common sequence shown by SEQ ID NO: 21 is enclosed in a circle.

Given below are the nucleotide sequences shown by SEQ ID NO: 49-57, respectively. Unless otherwise stated, the following individual sequences are shown in the direction from 5' to 3', with the purine bases (A and G) being in the 2'-OH form, and the pyrimidine bases (U and C) in the 2'-fluoro-modified form.

SEQ ID NO: 49:
(a sequence prepared by shortening the clone shown by SEQ ID NO: 4 to a 29-nucleotide length including the common sequence) GGUUCUACAGAUAGAGAUAAAGUA-GAACC SEQ ID NO: 50:
(a sequence prepared by shortening the clone shown by SEQ ID NO: 4 to a 35-nucleotide length including the common sequence) GGCAUUCUACAGAUAGAGAUAAAGUA-GAAUUUAAC SEQ ID NO: 51:
(a sequence prepared by shortening the clone shown by SEQ ID NO: 12 to a 45-nucleotide length) CGUUACAUAAU-GUAUAUACCAGGGUAACUAAACAUAGAAGAGCGG SEQ ID NO: 52:
(a sequence prepared by shortening the clone shown by SEQ ID NO: 12 to a 26-nucleotide length) CCGUAUAUAC-CAGGGUAACUAAACGG SEQ ID NO: 53:
(a sequence prepared by shortening the clone shown by SEQ ID NO: 13 to a 42-nucleotide length including the common sequence) GGGUAACUAUGGUUAGAUAGAG-UUAAAAACCAUAGAAGACCC SEQ ID NO: 54:
(a sequence prepared by shortening the clone shown by SEQ ID NO: 13 to a 36-nucleotide length including the common sequence) UAACUAUGGUUAGAUAGAGUUAAAAAC-CAUAGAAGA SEQ ID NO: 55:
(a sequence prepared by shortening the clone shown by SEQ ID NO: 13 to a 29-nucleotide length including the common sequence) CUAUGGUUAGAUAGAGUUAAAAAC-CAUAG SEQ ID NO: 56:
(a sequence prepared by shortening the clone shown by SEQ ID NO: 13 to a 23-nucleotide length including the common sequence) GGGUUAGAUAGAGUUAAAAACCC SEQ ID NO: 57:
(a sequence prepared by shortening the clone shown by SEQ ID NO: 14 to a 27-nucleotide length including the common sequence) GCAUUUGAGAUAGAUUUAAACAAACGC The nucleic acids of SEQ ID NO: 49-57 were all chemically synthesized.

Whether these nucleic acids bind to chymase was determined by the surface plasmon resonance method. Measurements were taken using Biacore T100 (manufactured by GE Healthcare) as described below. About 4000 RU of chymase (recombinant, manufactured by SIGMA) was immobilized on the sensor chip surface of a CM5 chip, using an amine coupling kit. 20 µL of each nucleic acid, prepared at 0.3 µM, as an analyte was injected at a flow rate of 20 µL/min. Solution C was used as a running buffer. The results of the measurements are shown in Table 4. The method of evaluation used was the same as Example 1.

As a result, the nucleic acids other than SEQ ID NO: 52 were identified as aptamers that bind to chymase significantly more potently than the control 40N (Table 4). A sensorgram showing how the aptamers shown by SEQ ID NO: 13, 55, and 56 bound to chymase is given in FIG. 7.

Chymase inhibitory activity was determined in the same manner as Example 3. The respective $IC_{50}$ values are shown in Table 4.

The nucleic acids other than SEQ ID NO: 52 exhibited potent inhibitory activity (Table 4). The results for SEQ ID NO: 51 and 52 showed that the aptamer shown by SEQ ID NO: 12, which does not comprise the common sequence, retained its activity after being shortened to a 45-nucleotide length, and lost the activity when shortened to a 26-nucleotide length.

Meanwhile, the results for SEQ ID NO: 56 showed that the aptamer shown by SEQ ID NO: 13, which comprises the common sequence, could be shortened to a 23-nucleotide length. This demonstrates that the common sequence shown by SEQ ID NO: 21 is critical to the binding and inhibitory activity against chymase.

Because SEQ ID NO: 49 and 57 also exhibited inhibitory activity, it was shown that the $N_1 N_2$ contained in the common sequence is not limited to GU, and that there is no limitation on the sequence contained in the stem structure of SEQ ID NO: 56 in FIG. 6, as far as the stem structure is retained.

These aptamers are considered to be useful as chymase inhibitors.

TABLE 4

Binding activity and inhibitory activity for chymase (IC$_{50}$).

| SEQ ID NO: | Sequence ID number of parent clone | Length | Binding activity as determined using Biacore | IC$_{50}$ [μM] |
|---|---|---|---|---|
| 49 | 4 | 29 | ++ | 0.117 ± 0.066 |
| 50 | 4 | 35 | ++ | 0.138 ± 0.093 |
| 51 | 12 | 45 | ++ | 0.024 ± 0.009 |
| 52 | 12 | 26 | + | >1 |
| 53 | 13 | 42 | ++ | 0.066 ± 0.024 |
| 54 | 13 | 36 | ++ | 0.051 ± 0.033 |
| 55 | 13 | 29 | ++ | 0.055 ± 0.023 |
| 56 | 13 | 23 | ++ | 0.046 ± 0.031 |
| 57 | 14 | 27 | ++ | 0.099 ± 0.013 |

"++" represents a sequence that binds to chymase significantly more strongly than the negative control 40N. "+" represents a sequence that binds to chymase equivalently compared with the negative control 40N. Here, 40N represents the nucleic acid pool used in the 1st round in Example 1, which comprises a random sequence of 40 nucleotides. ">1" indicates that no inhibitory activity was observed in the concentration range up to 1 μM. Each IC$_{50}$ value is a mean value for 2 to 3 measurements.

The negative control 40N did not exhibit inhibitory activity at concentrations of up to 1 μM (IC$_{50}$>1 μM). The positive control chymostatin exhibited IC$_{50}$ values of 0.1 μM-0.2 μM.

In summary, the nucleic acids listed in Table 4, other than SEQ ID NO: 52, exhibited inhibitory activity against chymase. The nucleic acids that exhibited IC$_{50}$ values of 0.1 μM or less, in particular, can be described as having a remarkable inhibitory effect.

Example 5

Effect of Substitution, Deletion of Base(s) of Shortened Aptamer

Mutation or deletion was introduced into the aptamer shown by SEQ ID NO: 56, and an influence on the binding activity and inhibitory activity was examined. The sequences are shown in SEQ ID NO: 58-68.

The nucleotide sequences of respective aptamers shown by the following SEQ ID NO: 58-68 are shown below. Unless otherwise specified, the respective sequences recited below are in the direction of from 5' to 3', modification at the 2'-position of ribose (e.g., U(F) shows modification of the 2'-position of ribose of uracil with F) is shown in the parenthesis, and F is a fluorine atom.

SEQ ID NO: 58:
(sequence containing randomly-placed 13 nucleic acid bases contained in the common sequence of the clone shown by SEQ ID NO: 56) GGGU(F)U(F)GAAGAU(F)AU(F)U(F)AAAGAAC(F)C(F)C(F)

SEQ ID NO: 59:
(sequence wherein N$_2$ contained in the common sequence of the clone shown by SEQ ID NO: 56 is substituted) GGGU(F)U(F)AGAU(F)AGAGAU(F)AAAAAC(F)C(F)C(F)

SEQ ID NO: 60:
(sequence wherein N$_2$ contained in the common sequence of the clone shown by SEQ ID NO: 56 is substituted) GGGU(F)U(F)AGAU(F)AGAGC(F)U(F)AAAAAC(F)C(F)C(F)

SEQ ID NO: 61:
(sequence wherein N$_1$ contained in the common sequence of the clone shown by SEQ ID NO: 56 is substituted) GGGU(F)U(F)AGAU(F)AGAU(F)U(F)U(F)AAAAAC(F)C(F)C(F)

SEQ ID NO: 62:
(sequence wherein X$_1$ and X$_2$ contained in the common sequence of the clone shown by SEQ ID NO: 56 are substituted) GGGU(F)U(F)GGAU(F)AGAGU(F)U(F)AAGAAC(F)C(F)C(F)

SEQ ID NO: 63:
(sequence wherein base sequence contained in the clone shown by SEQ ID NO: 56 except the common sequence is substituted) GC(F)U(F)AC(F)AGAU(F)AGAGU(F)U(F)AAAGU(F)AGC(F)

SEQ ID NO: 64:
(sequence wherein base sequence contained in the clone shown by SEQ ID NO: 56 except the common sequence is substituted) GU(F)C(F)AC(F)AGAU(F)AGAGU(F)U(F)AAAGU(F)GAC(F)

SEQ ID NO: 65:
(sequence wherein base sequence contained in the clone shown by SEQ ID NO: 56 except the common sequence is partly substituted and partly deleted) GGC(F)AGAU(F)AGAGU(F)U(F)AAAGC(F)C(F)

SEQ ID NO: 66:
(sequence wherein purine base contained in the common sequence of the clone shown by SEQ ID NO: 56 is substituted by pyrimidine base) GGGU(F)U(F)AGAU(F)CGAGU(F)U(F)AAAAAC(F)C(F)C(F)

SEQ ID NO: 67:
(sequence wherein purine base contained in the common sequence of the clone shown by SEQ ID NO: 56 is substituted by pyrimidine base) GGGU(F)U(F)AGAU(F)ACAGU(F)U(F)AAAAAC(F)C(F)C(F)

SEQ ID NO: 68:
(sequence wherein purine base contained in the common sequence of the clone shown by SEQ ID NO: 56 is substituted by pyrimidine base) GGGU(F)U(F)AGAU(F)AGUGU(F)U(F)AAAAAC(F)C(F)C(F)

All nucleic acids of SEQ ID NO: 58-68 were prepared by chemical synthesis. Whether these nucleic acids are bound to chymase was assessed by surface plasmon resonance method in the same manner as in Example 4. The inhibitory activity on chymase was measured in the same manner as in Example 3. The results are shown in Table 5.

As a result, it was found that the nucleic acids of SEQ ID NO: 59-65 from among those shown in Table 5 retained strong binding force and strong inhibitory activity.

Since the binding activity and inhibitory activity of SEQ ID NO: 58 decreased to almost the same level as 40N/30N used in Examples 1 and 2, it was shown that the common sequence shown by SEQ ID NO: 21 is important for the binding and inhibitory activities on chymase. From these results, SEQ ID NO: 58 was used as a negative control of the shortened aptamer in the following Examples (Examples 5-9).

From the results of SEQ ID NO: 59-61, it was shown that N$_1$ and N$_2$ contained in the common sequence may be any nucleotides, which are preferably GU, GA, GC and UU. From the results of SEQ ID NO: 62, it was shown that X$_1$ and X$_2$ may be any nucleotides, and are preferably A and G, more preferably both A or both G.

From the results of SEQ ID NO: 63-65, it was shown that the base pair sequence (e.g., SEQ ID NO: 56 in FIG. 6) of the stem structure contained therein except the common sequence may be any nucleotides as long as the stem structure is maintained, and the length is preferably 3 base pairs or longer.

From the results of SEQ ID NO: 66-68, the importance of the common sequence was shown again, since introduction of mutation into the common sequence decreases the activity.

TABLE 5 chymase-binding activity and chymase-inhibitory activity (IC$_{50}$).

| SEQ ID NO: | binding activity using Biacore | IC$_{50}$ [μM] |
| --- | --- | --- |
| 58 | + | >1 |
| 59 | ++ | 0.038 ± 0.009 |
| 60 | ++ | 0.026 ± 0.006 |
| 61 | ++ | 0.023 ± 0.006 |
| 62 | ++ | 0.029 ± 0.004 |
| 63 | ++ | 0.023 ± 0.003 |
| 64 | ++ | 0.020 ± 0.005 |
| 65 | ++ | 0.056 ± 0.046 |
| 66 | + | >1 |
| 67 | + | >1 |
| 68 | + | >1 |

In the binding activity, "++" shows significant binding to chymase than SEQ ID NO: 58 which is a negative control, and "+" shows similar binding level as SEQ ID NO: 58 which is a negative control. In the inhibitory activity, ">1" shows no inhibitory activity in the concentration range up to 1 μM. IC$_{50}$ value is a mean value of two measurements.

SEQ ID NO: 58 did not show an inhibitory activity in the concentration range up to 1 μM (IC$_{50}$>1 μM). In addition, the IC$_{50}$ value of chymostatin, which is a positive control, was 0.1 μM-0.2 μM. From the above results, it is clear that, among the aptamers shown in Table 5, the aptamers shown by SEQ ID NO: 59-65 have a strong chymase-inhibitory activity (IC$_{50}$<0.1 μM).

Example 6

Alteration of Shortened Aptamer-1

To enhance nuclease resistance of the aptamer shown by SEQ ID NO: 56, an altered aptamer with terminal modification, an altered aptamer wherein the 2'-position of ribose of purine base in the sequence is modified with O-methyl group or F, and an altered aptamer wherein phosphorothioate is introduced were prepared. The sequences are shown by SEQ ID NOs: 73-77, 56(8), 80, 56(10), 81-82, 56(13)-56(14), and 85-87. In addition, an altered aptamer wherein modification of pyrimidine nucleotide contained in the common sequence of the aptamer shown by SEQ ID NO: 56 (2'-F; modification of the 2-position of ribose with F) is changed to native type (2'-OH) was prepared, and the necessity of modification was evaluated. The sequences thereof are shown by SEQ ID NOs: 83-84.

The respective nucleotide sequences are shown below. Unless otherwise specified, the respective sequences recited below are in the direction of from 5' to 3', modification at the 2'-position of ribose is shown in the parenthesis, F is a fluorine atom and M is an O-methyl group. In respective sequence terminals, idT shows modification with inverted-dT, and PEG shows modification with 40 kDa branched polyethylene glycol. In the sequences, s shows phosphorothioation of a phosphate group between the nucleotides.

SEQ ID NO: 73:
(sequence wherein both terminals of the clone shown by SEQ ID NO: 56 are modified with idT) idT-GGGU(F)U(F)AGAU(F)AGAGU(F)U(F)AAAAAC(F)C(F)C(F)-idT SEQ ID NO: 74:
(sequence wherein modification is introduced into 3 positions of sequence other than the common sequence of the clone shown by SEQ ID NO: 56) G(M)G(M)G(M)U(F)U(F)AGAU(F)AGAGU(F)U(F)AAAAAC(F)C(F)C(F)

SEQ ID NO: 75:
(sequence wherein modification is introduced into 2 positions of sequence other than the common sequence of the clone shown by SEQ ID NO: 56) GGGU(F)U(F)AGAU(F)AGAGU(F)U(F)AAAA(M)A(M)C(F)C(F)C(F)

SEQ ID NO: 76:
(sequence wherein modification is introduced into 1 position of the common sequence of the clone shown by SEQ ID NO: 56) GGGU(F)U(F)AGAU(F)A(M)GAGU(F)U(F)AAAAAC(F)C(F)C(F)

SEQ ID NO: 77:
(sequence wherein modification is introduced into 2 positions of the common sequence of the clone shown by SEQ ID NO: 56) GGGU (F)U(F)AGAU(F)AGAGU(F)U(F)A(M)A(M)AAAC(F)C(F)C(F)

SEQ ID NO: 78:
(sequence wherein modification is introduced into 1 position of the common sequence of the clone shown by SEQ ID NO: 56) GGGU(F)U(F)AG(M)AU(F)AGAGU(F)U(F)AAAAAC(F)C(F)C(F)

SEQ ID NO: 79:
(sequence wherein modification is introduced into 1 position of the common sequence of the clone shown by SEQ ID NO: 56) GGGU(F)U(F)AGA(M)U(F)AGAGU(F)U(F)AAAAAC(F)C(F)C(F)

SEQ ID NO: 56(8):
(sequence wherein modification is introduced into 1 position of the common sequence of the clone shown by SEQ ID NO: 56) GGGU(F)U(F)AGAU(F)AG(M)AGU(F)U(F)AAAAAC(F)C(F)C(F)

SEQ ID NO: 80:
(sequence wherein modification is introduced into 1 position of the common sequence of the clone shown by SEQ ID NO: 56) GGGU(F)U(F)AGAU(F)AGA(M)GU(F)U(F)AAAAAC(F)C(F)C(F)

SEQ ID NO: 56(10):
(sequence wherein modification is introduced into 1 position of the common sequence of the clone shown by SEQ ID NO: 56) GGGU(F)U(F)A(M)GAU(F)AGAGU(F)U(F)AAAAAC(F)C(F)C(F)

SEQ ID NO: 81:
(sequence wherein modification is introduced into 1 position of the common sequence of the clone shown by SEQ ID NO: 56) GGGU(F)U(F)AGAU(F)AGAGU(F)U(F)AAA(M)AAC(F)C(F)C(F)

SEQ ID NO: 82:
(sequence wherein modification is introduced into 1 position of the common sequence of the clone shown by SEQ ID NO: 56) GGGU(F)U(F)AGAU(F)AGAG(M)U(F)U(F)AAAAAC(F)C(F)C(F)

SEQ ID NO: 56(13):
(sequence wherein modification is introduced into 1 position of the common sequence of the clone shown by SEQ ID NO: 56) GGGU(F)U(F)AGAU(F)AG(F)AGU(F)U(F)AAAAAC(F)C(F)C(F)

SEQ ID NO: 56(14):
(sequence wherein modification is introduced into 1 position of the common sequence of the clone shown by SEQ ID NO: 56) GGGU(F)U(F)AGAU(F)AGA(F)GU(F)U(F)AAAAAC(F)C(F)C(F)

SEQ ID NO: 83:
(sequence wherein the 9th nucleotide U(F) of the clone shown by SEQ ID NO: 56 is substituted by U) GGGU(F)U(F)A-GAUAGAGU(F)U(F)AAAAAC(F)C(F)C(F)

SEQ ID NO: 84:
(sequence wherein the 15th nucleotide U(F) of the clone shown by SEQ ID NO: 56 is substituted by U) GGGU(F)U(F)AGAU(F)AGAGU(F)UAAAAAC(F)C(F)C(F)

SEQ ID NO: 85:
(sequence wherein the terminals of the clone shown by SEQ ID NO: 56 are modified with PEG and idT) PEG-GGGU(F)U(F)AGAU(F)AGAGU(F)U(F)AAAAAC(F)C(F)C(F)-idT
SEQ ID NO: 86:
(sequence wherein one phosphate group in the common sequence of the clone shown by SEQ ID NO: 56 is phosphorothioated) GGGU(F)U(F)sAGAU(F) AGAGU(F)U(F)AAAAAC(F)C(F)C(F)
SEQ ID NO: 87:
(sequence wherein one phosphate group in the common sequence of the clone shown by SEQ ID NO: 56 is phosphorothioated) GGGU(F)U(F)AsGAU(F)AGAGU(F)U(F)AAAAAC(F)C(F)C(F)

All nucleic acids of SEQ ID NOs: 73-79, 56(8), 80, 56(10), 81, 56(13)-56(14), 83-87 were prepared by chemical synthesis. Whether these nucleic acids are bound to chymase was assessed by surface plasmon resonance method in the same manner as in Example 4. The measurement results are shown in Table 6.

As a result, nucleic acids other than SEQ ID NO: 56(8), 56(10), 56(13), 56(14) showed a significant chymase-binding activity than SEQ ID NO: 58, which is a negative control.

The inhibitory activity on chymase was measured in the same manner as in Example 3. The $IC_{50}$ values are shown in Table 6. It was found that the nucleic acids other than SEQ ID NO: 56(8), 56(10), 56(13), 56(14) showed an inhibitory activity, though the level of inhibitory activity varied. By comparison of the $IC_{50}$ values, the inhibitory activity of SEQ ID NO: 73-79, 81, 82 was maintained almost at the same level as SEQ ID NO: 56. On the other hand, the inhibitory activity of SEQ ID NO: 80, 83, 84, 85 was decreased as compared to SEQ ID NO: 56, and the inhibitory activity of SEQ ID NO: 56(8), 56(10), 56(13), 56(14) was shown to have disappeared. Furthermore, the inhibitory activity of SEQ ID NO: 86, 87 was shown to have increased than SEQ ID NO: 56.

From the results of SEQ ID NO: 73, 85, it was found that an influence of the modification of the terminal on the activity was small. From the results of SEQ ID NO: 74, 75, it was shown that the modification of the stem sequence did not influence the activity. As to the nucleotides contained in the common sequence, the modification permitted maintenance of the inhibitory activity in 76-79, 81, 82, and decreased (or eliminated) the inhibitory activity in SEQ ID NO: 56(8), 80, 56(10), 56(13), 56(14).

From the above, it was found that at least one nucleotide of the aptamer shown by SEQ ID NO: 56 may be modified to increase the stability of the aptamer. As the modification of nucleotide, for example, 2'-amino modification and the like can be mentioned in addition to 2'-O-methyl modification.

On the other hand, from the results of SEQ ID NO: 83, 84, it was found that the inhibitory activity decreases by changing any (9th or 15th) of the nucleotide modified aptamers (U(F)) contained in the common sequence of the clone shown by SEQ ID NO: 56 to native ribonucleotide (U). In general, the modification of nucleotide increases nuclease resistance of aptamer. Therefore, at least one of the pyrimidine nucleotides (9th U and 15th U of the clone shown by SEQ ID NO: 56) contained in the common sequence is preferably a modified nucleotide.

Moreover, from the results of SEQ ID NO: 56(8), 80, 56(10), 56(13), 56(14), at least one of the 6th A, 11th G and 12th A of the native purine bases contained in the common sequence of the clone shown by SEQ ID NO: 56 is preferably a native ribonucleotide, since introduction of modification thereinto decreases the inhibitory activity.

Furthermore, from the results of SEQ ID NO: 86, 87, it was found that the inhibitory activity increases by introduction of phosphorothioate into at least one position as a modification of a phosphate group, in addition to the modification of a sugar residue.

TABLE 6 chymase-binding activity and chymase-inhibitory activity ($IC_{50}$).

| SEQ ID NO: | binding activity using Biacore | $IC_{50}$ [μM] |
| --- | --- | --- |
| 56 | ++ | 0.027 ± 0.002 |
| 56(1) | ++ | 0.026 ± 0.007 |
| 56(2) | ++ | 0.024 ± 0.003 |
| 56(3) | ++ | 0.025 ± 0.002 |
| 56(4) | ++ | 0.027 ± 0.005 |
| 56(5) | ++ | 0.029 ± 0.001 |
| 56(6) | ++ | 0.031 ± 0.001 |
| 56(7) | ++ | 0.038 ± 0.001 |
| 56(8) | + | >1 |
| 56(9) | ++ | 0.111 ± 0.003 |
| 56(10) | + | >1 |
| 56(11) | ++ | 0.028 ± 0.003 |
| 56(12) | ++ | 0.035 ± 0.003 |
| 56(13) | + | >1 |
| 56(14) | + | >1 |
| 56(15) | ++ | 0.061 ± 0.014 |
| 56(16) | ++ | 0.058 ± 0.002 |
| 56(17) | n.d. | 0.058 ± 0.000 |
| 56(18) | ++ | 0.012 ± 0.001 |
| 56(19) | ++ | 0.008 ± 0.001 |

In the binding activity, "++" shows significant binding to chymase than SEQ ID NO: 58 which is a negative control, and "+" shows similar binding level as SEQ ID NO: 58 which is a negative control. "n.d." shows not determined. ">1" shows no inhibitory activity in the concentration range up to 1 μM. $IC_{50}$ value is a mean value of two measurements.

SEQ ID NO: 58, which is a negative control, did not show an inhibitory activity in the concentration range up to 1 μM ($IC_{50}$>1 μM). In addition, the $IC_{50}$ value of chymostatin, which is a positive control, was 0.1 μM-0.2 μM.

From the above results, among the nucleic acids shown in Table 6, particularly one showing an $IC_{50}$ value of 0.1 μM or below had a strong chymase-inhibitory activity and was suggested to be usable as a chymase inhibitor.

Example 7

Alteration of Shortened Aptamer-2

The aptamer shown by SEQ ID NO: 56 was altered further based on the results of Example 6. Altered aptamers subjected to introduction of 2'-O-methyl group, various terminal modifications, introduction of phosphorothioate, substitution of ribonucleotide to DNA and the like, and a combination of such modifications were synthesized. The sequences are shown in SEQ ID NO: 88-115, 121, 69, 122, 123, 70-74, 74(1), 75-77, 77(1), 77(2), 78-82.

The respective nucleotide sequences are shown below. Unless otherwise specified, the respective sequences recited below are in the direction of from 5' to 3', upper case letters show RNA and lower case letters show DNA. The modification at the 2'-position of ribose is shown in parenthesis, F is a fluorine atom and M is an O-methyl group. In respective sequence terminals, idT shows modification with inverted-dT, PEG shows modification with 40 kDa branched polyethylene glycol, Cho shows modification with cholesterol and B shows modification with biotin. Peptide 1 shows conjugation of Phe-Cys at the C-terminal side, Peptide 2 shows conjugation of Cys-Phe at the N-terminal side, and each peptide is conjugated to the 5' end of the nucleic acid via a disulfide bond. In the sequences, s shows phosphorothioation of a phosphate group between the nucleotides.

SEQ ID NO: 88:
G(M)G(M)G(M)U(F)U(F)AG(M)A(M)U(F)A(M)GAGU(F)U(F)A(M)A(M)AA(M)A(M)C(F)C(F)C(F)

SEQ ID NO: 89:
G(M)G(M)G(M)U(F)U(F)AG(M)A(M)U(F)A(M)GAG(M)U(F)U(F)A(M)A(M)A(M)A(M)A(M)C(F)C(F)C(F)

SEQ ID NO: 90:
G(M)G(M)G(M)U(F)U(F)sAG(M)A(M)U(F)A(M)GAG(M)U(F)U(F)A(M)A(M)A(M)A(M)A(M)C(F)C(F)C(F)

SEQ ID NO: 91:
G(M)G(M)G(M)U(F)U(F)AsG(M)A(M)U(F)A(M)GAG(M)U(F)U(F)A(M)A(M)A(M)A(M)A(M)C(F)C(F)C(F)

SEQ ID NO: 92:
idT-G(M)G(M)G(M)U(F)U(F)AGAU(F)AGAGU(F)U(F)AAAA(M)A(M)C(F)C(F)C(F)-idT

SEQ ID NO: 93:
idT-GGGU(F)U(F)AG(M)A(M)U(F)A(M)GAGU(F)U(F)AAAAAC(F)C(F)C(F)-idT

SEQ ID NO: 94:
idT-G(M)G(M)G(M)U(F)U(F)AG(M)A(M)U(F)A(M)GAG(M)U(F)U(F)A(M)A(M)A(M)A(M)A(M)C(F)C(F)C(F)-idT

SEQ ID NO: 95:
PEG-G(M)G(M)G(M)U(F)U(F)AG(M)A(M)U(F)A(M)GAG(M)U(F)U(F)A(M)A(M)A(M)A(M)A(M)C(F)C(F)C(F)-idT

SEQ ID NO: 96:
idT-G(M)G(M)G(M)U(F)U(F)AsG(M)A(M)U(F)A(M)GAG(M)U(F)U(F)A(M)A(M)A(M)A(M)A(M)C(F)C(F)C(F)-idT

SEQ ID NO: 97:
idT-G(M)G(M)G(M)U(F)U(F)sAsG(M)A(M)U(F)A(M)GAG(M)U(F)U(F)A(M)A(M)A(M)A(M)A(M)C(F)C(F)C(F)-idT

SEQ ID NO: 98:
idT-G(M)G(M)G(M)U(F)U(F)AGA(M)U(F)A(M)GAG(M)U(F)U(F)A(M)A(M)A(M)A(M)A(M)C(F)C(F)C(F)-idT

SEQ ID NO: 99:
idT-G(M)G(M)G(M)U(F)U(F)AG(M)AU(F)A(M)GAG(M)U(F)U(F)A(M)A(M)A(M)A(M)A(M)C(F)C(F)C(F)-idT

SEQ ID NO: 100:
idT-G(M)G(M)G(M)U(F)U(F)AGAU(F)A(M)GAG(M)U(F)U(F)A(M)A(M)A(M)A(M)A(M)C(F)C(F)C(F)-idT

SEQ ID NO: 101:
idT-G(M)G(M)G(M)U(F)U(F)AsGA(M)U(F)A(M)GAG(M)U(F)U(F)A(M)A(M)A(M)A(M)A(M)C(F)C(F)C(F)-idT

SEQ ID NO: 102:
idT-G(M)G(M)G(M)U(F)U(F)AsG(M)AU(F)A(M)GAG(M)U(F)U(F)A(M)A(M)A(M)A(M)A(M)C(F)C(F)C(F)-idT

SEQ ID NO: 103:
idT-G(M)G(M)G(M)U(F)U(F)AsGAU(F)A(M)GAG(M)U(F)U(F)A(M)A(M)A(M)A(M)A(M)C(F)C(F)C(F)-idT

SEQ ID NO: 104:
idT-G(M)G(M)G(M)U(F)U(F)AGsAU(F)A(M)GAG(M)U(F)U(F)A(M)A(M)A(M)A(M)A(M)C(F)C(F)C(F)-idT

-continued

SEQ ID NO: 105:
idT-
G(M)G(M)G(M)U(F)U(F)AsGsAU(F)A(M)GAG(M)U(F)U(F)A(M)A(M)A(M)A(M)
A(M)C(F)C(F)C(F)-idT

SEQ ID NO: 106:
idT-
G(M)G(M)G(M)U(F)U(F)sAsGAU(F)A(M)GAG(M)U(F)U(F)A(M)A(M)A(M)A(M)
A(M)C(F)C(F)C(F)-idT

SEQ ID NO: 107:
PEG-
GG(M)G(M)U(F)U(F)AG(M)A(M)U(F)A(M)GAG(M)U(F)U(F)A(M)A(M)A(M)A
(M)A(M)C(F)C(F)C(F)-idT

SEQ ID NO: 108:
idT-
GG(M)G(M)U(F)U(F)AG(M)A(M)U(F)A(M)GAG(M)U(F)U(F)A(M)A(M)A(M)A
(M)A(M)C(F)C(F)C(F)-idT

SEQ ID NO: 109:
idT-
GG(M)G(M)U(F)U(F)AsG(M)A(M)U(F)A(M)GAG(M)U(F)U(F)A(M)A(M)A(M)A
(M)A(M)C(F)C(F)C(F)-idT

SEQ ID NO: 110:
Cho-
G(M)G(M)G(M)U(F)U(F)AG(M)A(M)U(F)A(M)GAG(M)U(F)U(F)A(M)A(M)A(M)
A(M)A(M)C(F)C(F)C(F)-idT

SEQ ID NO: 111:
Peptide 1-
G(M)G(M)G(M)U(F)U(F)AG(M)A(M)U(F)A(M)GAG(M)U(F)U(F)A(M)A(M)A(M)
A(M)A(M)C(F)C(F)C(F)-idT SEQ ID NO: 112:
Peptide 2-
G(M)G(M)G(M)U(F)U(F)AG(M)A(M)U(F)A(M)GAG(M)U(F)U(F)A(M)A(M)A(M)
A(M)A(M)C(F)C(F)C(F)-idT SEQ ID NO: 113:
idT-
G(M)G(M)G(M)U(F)U(F)AG(M)A(M)U(F)A(M)GAG(M)U(F)U(F)A(M)A(M)A(M)
A(M)A(M)C(F)C(F)C(F)-PEG SEQ ID NO: 114:
B-idT-
G(M)G(M)G(M)U(F)U(F)AG(M)A(M)U(F)A(M)GAG(M)U(F)U(F)A(M)A(M)A(M)
A(M)A(M)C(F)C(F)C(F)-idT SEQ ID NO: 115:
idT-
G(M)G(M)G(M)U(F)U(F)AG(M)A(M)U(F)A(M)GAG(M)U(F)U(F)A(M)A(M)A(M)
A(M)A(M)C(F)C(F)C(F)-idT-B SEQ ID NO: 116:
idT-
G(M)G(M)G(M)U(F)U(F)AG(M)A(M)U(F)A(M)GAG(M)U(F)U(F)A(M)A(M)A(M)
A(M)A(M)ccc-idT SEQ ID NO: 117:
idT-
G(M)G(M)G(M)U(F)U(F)aG(M)AU(F)A(M)GAG(M)U(F)U(F)A(M)A(M)A(M)A
(M)A(M)C(F)C(F)C(F)-idT SEQ ID NO: 118:
idT-
G(M)G(M)G(M)U(F)U(F)AG(M)aU(F)A(M)GAG(M)U(F)U(F)A(M)A(M)A(M)A
(M)A(M)C(F)C(F)C(F)-idT SEQ ID NO: 119:
B-idT-
G(M)G(M)G(M)U(F)U(F)AG(M)aU(F)A(M)GAG(M)U(F)U(F)A(M)A(M)A(M)A
(M)A(M)C(F)C(F)C(F)-idT SEQ ID NO: 120:
idT-
G(M)G(M)G(M)U(F)U(F)AgaU(F)A(M)GAG(M)U(F)U(F)A(M)A(M)A(M)A(M)A
(M)C(F)C(F)C(F)-idT SEQ ID NO: 121:
G(M)G(M)U(F)U(F)AG(M)A(M)U(F)A(M)GAU(F)U(F)A(M)A(M)
A(M)A(M)C(F)C(F)C(F)

SEQ ID NO: 69:
PEG-
A(M)A(M)G(M)G(M)G(M)U(F)U(F)AG(M)A(M)U(F)A(M)GAG(M)U(F)U(F)
A(M)A(M)A(M)A(M)A(M)C(F)C(F)C(F)-idT

SEQ ID NO: 122:
idT-
A(M)A(M)A(M)G(M)G(M)G(M)U(F)U(F)AsG(M)A(M)U(F)A(M)GAG(M)U(F)U
(F)A(M)A(M)A(M)A(M)A(M)C(F)C(F)C(F)-idT

SEQ ID NO: 123:
idT-
A(M)A(M)A(M)G(M)G(M)G(M)U(F)U(F)AG(M)A(M)U(F)A(M)GAG(M)U(F)U(F)
A(M)A(M)A(M)A(M)A(M)C(F)C(F)C(F)-idT

SEQ ID NO: 70:
idT-
G(M)G(M)G(M)ttAG(M)A(M)U(F)A(M)GAG(M)U(F)U(F)A(M)A(M)A(M)A(M)A
(M)C(F)C(F)C(F)-idT

SEQ ID NO: 71:
idT-
G(M)G(M)G(M)U(F)U(F)AG(M)A(M)U(F)A(M)GAG(M)tU(F)A(M)A(M)A(M)A
(M)A(M)C(F)C(F)C(F)-idT

SEQ ID NO: 72:
idT-
G(M)G(M)G(M)G(M)ttAG(M)A(M)U(F)A(M)GAG(M)tU(F)A(M)A(M)A(M)A(M)A(M)
ccc-idT SEQ ID NO: 124:
idT-
G(M)G(M)G(M)G(M)ttAG(M)aU(F)A(M)GAG(M)tU(F)A(M)A(M)A(M)A(M)A(M)ccc-
idT SEQ ID NO: 125:
idT-
G(M)G(M)G(M)G(M)ttAsG(M)aU(F)A(M)GAG(M)tU(F)A(M)A(M)A(M)A(M)A(M)cc
c-idT SEQ ID NO: 126:
idT-
G(M)G(M)G(M)G(M)ttAG(M)A(M)U(F)A(M)GAgtU(F)A(M)A(M)A(M)A(M)A(M)ccc-
idT SEQ ID NO: 127:
idT-
G(M)G(M)G(M)G(M)ttAG(M)A(M)U(F)A(M)GAG(M)tU(F)aA(M)A(M)A(M)A(M)ccc-
idT SEQ ID NO: 128:
idT-
G(M)G(M)G(M)G(M)ttAG(M)A(M)U(F)A(M)GAG(M)tU(F)A(M)aA(M)A(M)A(M)ccc-
idT SEQ ID NO: 129:
idT-
G(M)G(M)G(M)G(M)ttAG(M)A(M)U(F)A(M)GAG(M)tU(F)A(M)A(M)aA(M)A(M)ccc-
idT SEQ ID NO: 130:
idT-
G(M)G(M)G(M)G(M)ttAG(M)aU(F)A(M)GAG(M)tU(F)A(M)A(M)A(M)A(M)A(M)ccc-
PEG SEQ ID NO: 131:
B-idT-
G(M)G(M)G(M)G(M)ttAG(M)aU(F)A(M)GAG(M)tU(F)A(M)A(M)A(M)A(M)A(M)ccc-
idT All nucleic acids of SEQ ID NO: 88-120, 121, 69, 122, 123, 70-72, 124-131 were prepared by chemical synthesis. Whether these nucleic acids are bound to chymase was assessed by surface plasmon resonance method in the same manner as in Example 4. The results are shown in Table 7.

As a result, all nucleic acids (excluding undetermined nucleic acids) were significantly bound to chymase than the negative control.

The chymase inhibitory activity was measured in the same manner as in Example 3. The $IC_{50}$ values are shown in Table 7. As a result, all nucleic acids shown in Table 7 exhibited a strong inhibitory activity.

From the results of SEQ ID NO: 95 and 113, it was shown that a terminal modification such as PEG may be introduced at any of the 5' end and the 3' end.

From the results of SEQ ID NO: 111, 112, 114 and 115, moreover, it was found that the terminal modification may be peptide, amino acid or a compound such as biotin and the like, besides idT and PEG shown in Example 6.

From the results of SEQ ID NO: 94 and 123, 95 and 69, and 96 and 122, moreover, it was found that terminal modification such as idT and PEG via a polynucleotide chain does not influence the inhibitory activity. As such spacer, any polynucleotide chain and, for example, an alkyl type spacer may be used.

It was also found that the inhibitory activity increases by substituting a part of F-form to a DNA-form.

TABLE 7 chymase-binding activity and chymase-inhibitory activity ($IC_{50}$).

| SEQ ID NO: | binding activity using Biacore | $IC_{50}$ [μM] |
|---|---|---|
| 56(20) | ++ | 0.102 ± 0.009 |
| 56(21) | ++ | 0.045 ± 0.006 |
| 56(22) | ++ | 0.052 ± 0.002 |
| 56(23) | ++ | 0.032 ± 0.003 |
| 56(24) | ++ | 0.038 ± 0.003 |
| 56(25) | ++ | 0.070 ± 0.009 |
| 56(26) | ++ | 0.054 ± 0.002 |
| 56(27) | n.d. | 0.084 ± 0.006 |
| 56(28) | ++ | 0.044 ± 0.002 |
| 56(29) | ++ | 0.036 ± 0.003 |
| 56(30) | ++ | 0.034 ± 0.003 |
| 56(31) | ++ | 0.023 ± 0.001 |
| 56(32) | ++ | 0.017 ± 0.000 |
| 56(33) | ++ | 0.035 ± 0.002 |
| 56(34) | ++ | 0.031 ± 0.006 |
| 56(35) | ++ | 0.024 ± 0.005 |
| 56(36) | ++ | 0.097 ± 0.017 |
| 56(37) | ++ | 0.046 ± 0.007 |
| 56(38) | ++ | 0.019 ± 0.005 |
| 56(39) | n.d. | 0.086 ± 0.018 |
| 56(40) | ++ | 0.051 ± 0.001 |
| 56(41) | ++ | 0.053 ± 0.013 |
| 56(42) | ++ | 0.071 ± 0.001 |
| 56(43) | ++ | 0.035 ± 0.003 |
| 56(44) | ++ | 0.042 ± 0.007 |
| 56(45) | n.d. | 0.059 ± 0.006 |
| 56(46) | ++ | 0.049 ± 0.002 |
| 56(47) | ++ | 0.037 ± 0.006 |
| 56(48) | ++ | 0.036 ± 0.003 |
| 56(49) | ++ | 0.069 ± 0.000 |
| 56(50) | ++ | 0.027 ± 0.002 |
| 56(51) | ++ | 0.029 ± 0.003 |
| 56(52) | ++ | 0.052 ± 0.001 |
| 61(1) | ++ | 0.078 ± 0.004 |
| 69 | n.d. | 0.091 ± 0.019 |
| 69(1) | ++ | 0.044 ± 0.002 |
| 69(2) | ++ | 0.048 ± 0.002 |
| 70 | ++ | 0.027 ± 0.004 |
| 71 | ++ | 0.028 ± 0.005 |
| 72 | ++ | 0.020 ± 0.002 |
| 72(1) | ++ | 0.013 ± 0.003 |
| 72(2) | ++ | 0.014 ± 0.002 |
| 72(3) | ++ | 0.050 ± 0.004 |
| 72(4) | ++ | 0.065 ± 0.002 |
| 72(5) | ++ | 0.027 ± 0.002 |
| 72(6) | ++ | 0.041 ± 0.002 |
| 72(7) | n.d. | 0.055 ± 0.002 |
| 72(8) | n.d. | 0.018 ± 0.001 |

In the binding activity, "++" shows significant binding to chymase than SEQ ID NO: 58 which is a negative control. "n.d." shows not determined. $IC_{50}$ value is a mean value of two measurements.

SEQ ID NO: 58, which is a negative control, did not show an inhibitory activity in the concentration range up to 1 μM ($IC_{50}$>1 μM). In addition, the $IC_{50}$ value of chymostatin, which is a positive control, was 0.1 μM-0.2 μM.

From the above results, all nucleic acids shown in Table 7 had a strong chymase-inhibitory activity and are suggested to be usable as a chymase inhibitor.

Summarizing the results of Examples 1 to 7 above, an aptamer effective as a chymase inhibitor satisfies particularly at least one of the following conditions.

(1) It contains the common sequence ($X_1$GAUAGAN$_1$N$_2$UAAX$_2$) shown by SEQ ID NO: 21.

(2) While the pyrimidine nucleotide contained in the common sequence may be a native nucleotide, a part of the pyrimidine nucleotide is preferably a modified nucleotide or DNA.

(3) While $N_1N_2$ may be any nucleotide, it is preferably GU, GA, GC, UU, CU or GT.

(4) While $X_1$ and $X_2$ may be any nucleotides, they are preferably, whether identical or not, A or G, more preferably are both A or both G.

(5) While the base pairs sequence in the stem structure (e.g., SEQ ID NO: 56 in FIG. 6) may be any nucleotide as long as the stem structure is maintained, its length is preferably 3 base pairs or longer.

(6) Except for a part of nucleotides (6th A, 11th G and 12th A of SEQ ID NO: 56), each nucleotide is partially modified or partially substituted by DNA.

(7) A terminal modification is introduced.

(8) A part of a phosphate group between nucleotides may be phosphorothioated.

Example 8

Measurement of Chymase Inhibitory Activity Using Angiotensin I as Substrate

For further assessment of the inhibitory activity of the nucleic acid of the present invention, the enzyme activity of chymase was measured using angiotensin I, which is a native substrate for chymase, according to the following method. Angiotensin I is converted by chymase to angiotensin II, during which a peptide fragment His-Leu is released. Since the peptide His-Leu is fluorescently derivatized by o-phthalaldehyde, its fluorescence intensity can be quantitatively measured.

The total volume of solution for an enzyme reaction in the assay was set to 50 μL, and the reaction was performed in solution C buffer. First, 0.3-0.75 ng of chymase (recombinant, (manufactured by SIGMA) or native (manufactured by Calbiochem)) was diluted with solution C to give 5 μL thereof. Here, the recombinant is chymase expressed by yeast, and the native is chymase purified from human skin mast cell. The nucleic acid was serially diluted with solution C at a concentration of 0.0027-2 μM to give 25 μL thereof. The chymase solution (5 μL) and the nucleic acid solution (25 μL) were mixed, and the mixture was incubated at 37° C. for 5 min. On the other hand, 125 mM angiotensin I (manufactured by PEPTIDE INSTITUTE, INC.) was prepared in solution C to give 20 L thereof, which was incubated at 37° C. for 5 min. The angiotensin I solution was added to a mixture of chymase and nucleic acid to start an enzyme reaction. The final chymase concentration of the reaction solution was 0.2-0.5 nM, and the final substrate concentration was 50 μM. After reaction at 37° C. for 90 min, ice-cooled 30% trichloroacetic acid solution (25 μL) was added to quench the reaction. The whole mixture was centrifuged at 4° C., 14000 rpm for 10 min, and the supernatant (30 μL) was used for the next fluorescence induction reaction.

The above-mentioned supernatant (30 μL) was added to a 96 well plate (black, manufactured by Costar), a solution (15 μL) of 2% o-phthalaldehyde (manufactured by SIGMA) in methanol and 0.3M NaOH solution (170 μL) were added to each well, and the mixture was incubated at room temperature for 10 min. Then, 3M HCl solution (25 μL) was added to quench the reaction. The plate was set on a microplate reader SpectraMax190 (manufactured by Molecular device) and the fluorescence intensity was measured at an excitation wavelength of 355 nm and a fluorescence wavelength of 460 nm.

Using SEQ ID NO: 58 as a control (negative control) and chymostatin, which is a known chymotrypsin-like serine protease inhibitor (positive control), a similar treatment and measurement were performed. The fluorescence intensity at reaction time 0 min under each condition was used as a blank. The fluorescence intensity detected by the addition of the same amount of solution C instead of the nucleic acid in the chymase enzyme reaction was taken as 100%, and the inhibitory rate of each test substance was calculated by the following formula.

Inhibitory rate (%)=[1−{(fluorescence intensity with test substance−fluorescence intensity of blank with test substance)/(fluorescence intensity without test substance−fluorescence intensity of blank without test substance)}]×100

The concentration of the inhibitor necessary for 50% inhibition of the enzyme activity ($IC_{50}$) was determined. The results are shown in Table 8.

TABLE 8 chymase inhibitory activity ($IC_{50}$) using angiotensin I as substrate.

| SEQ ID NO: | $IC_{50}$ [μM] for native chymase | $IC_{50}$ [μM] for recombinant chymase |
| --- | --- | --- |
| 4 | 0.031 | 0.003 |
| 13 | 0.074 | 0.041 |
| 14 | 0.063 | 0.022 |
| 53 | 0.764 | 0.446 |
| 54 | 0.614 | 0.397 |
| 55 | 0.606 | 0.354 |
| 56 | 0.508 | 0.235 |
| 65 | 0.878 | 0.274 |
| 56(1) | 0.404 | 0.207 |
| 56(17) | 0.613 | 0.456 |
| 56(18) | 0.174 | 0.108 |
| 56(19) | 0.130 | 0.055 |
| 56(21) | 0.722 | 0.361 |
| 56(22) | 0.563 | 0.237 |
| 56(23) | 0.360 | 0.119 |
| 56(26) | 0.743 | 0.326 |
| 56(27) | >1 | 0.724 |
| 56(28) | 0.410 | 0.137 |
| 56(29) | 0.366 | 0.080 |
| 56(30) | 0.521 | 0.210 |
| 56(31) | 0.266 | 0.089 |
| 56(32) | 0.185 | 0.078 |
| 56(33) | 0.291 | 0.085 |
| 56(34) | 0.162 | 0.057 |
| 56(35) | 0.120 | 0.039 |
| 56(42) | 0.601 | 0.687 |
| 56(43) | 0.591 | 0.328 |
| 56(44) | 0.643 | 0.414 |
| 56(45) | 0.303 | 0.377 |
| 56(46) | 0.742 | 0.426 |
| 56(47) | 0.542 | 0.419 |
| 56(48) | 0.621 | 0.394 |
| 56(50) | 0.325 | 0.153 |
| 56(51) | 0.429 | 0.310 |
| 69 | >1 | 0.628 |
| 69(1) | 0.480 | 0.125 |
| 69(2) | 0.752 | 0.289 |
| 70 | 0.478 | 0.239 |
| 71 | 0.341 | 0.161 |
| 72 | 0.120 | 0.065 |
| 72(1) | 0.103 | 0.036 |
| 72(2) | 0.076 | 0.037 |
| 72(5) | 0.377 | 0.201 |
| 72(6) | 0.573 | 0.370 |
| 72(7) | 0.312 | 0.158 |
| 72(8) | 0.097 | 0.043 |

$IC_{50}$ is the value of one measurement.

SEQ ID NO: 58 used as a negative control did not show an inhibitory activity ($IC_{50}$>1 μM). The $IC_{50}$ values of chymostatin, a positive control, were 0.35-0.5 μM (Native), 0.45-0.6 μM (Recombinant). The activity of PEG-conjugated aptamer is relatively low as compared to aptamer not bound with PEG. This is a general phenomenon caused by the larger size of PEG (molecular weight about 40,000) than aptamer (molecular weight about 10,000). Since PEG-conjugation markedly improves in vivo pharmacokinetics, an in vivo effect is expected even if efficacy decreases somewhat in vitro.

From the above results, any nucleic acid contained in Table 8 is expected as a drug for the prophylaxis and/or treatment of various diseases involving angiotensin, since it shows a strong chymase inhibitory activity even when angiotensin I, a native substrate, is used.

Example 9

Measurement of LTBP-1 Degradation Inhibitory Activity Using Normal Human Lung Fibroblast (Normal Human Lung Fibroblast: NHLF)

Chymase is deeply involved in the activation of TGF-β, which is one of the important factors causing fibrosis. It is suggested that, in the process of TGF-β activation, chymase degrades LTBP-1 to liberate latent TGF-β, which is present as a latent form in an extracellular matrix, and is involved in the reaction converting latent TGF-β to active TGF-β. Whether the nucleic acid of the present invention has an inhibitory activity against LTBP-1 degradation by chymase was assessed by the method shown below.

Cryopreserved NHLF cells (manufactured by Cambrex Bio Science) were rapidly thawed in a water bath at 37° C. and suspended in a medium (10% FBS/F-12). After centrifugation (1200 rpm, 5 min), the supernatant was removed and the cells were re-suspended in the medium. The medium was added to a total amount of 10 mL, and the mixture was transferred to a petri dish for cell culture and the cells were cultured at 37° C., 5% $CO_2$. The cell form and growth state were observed with a microscope and, upon confluence, the medium was exchanged with a serum-free medium (0.2% BSA/F-12). Two days after medium exchange, the culture supernatant was collected, dispensed and cryopreserved at −30° C.

The NHLF culture supernatant (40 μL) thawed when in use was dispensed to a tube, a nucleic acid solution obtained by diluting with solution C to 50 μM was added by 5 μL. As a positive control, chymostatin was diluted with solution C and added in the same manner. As a negative control, only solution C was used and added in the same manner. Then, chymase diluted with solution E (solution C+0.1% BSA, 0.05% sodium azide) to 100 ng/mL was added by 5 μL. The final concentration of chymase in the reaction solution was 10 ng/mL (0.33 nM), and the final nucleic acid concentration was 5 μM. As a control, a tube free of chymase was prepared. After pipetting, samples were incubated at 37° C. for 1 hr, and mixed with an equivalent amount of electrophoresis Lysis buffer to terminate the reaction. Then, LTBP-1 in the sample was detected by Western blotting shown below.

A sample obtained by mixing with a lysis buffer was boiled for 3 min, 10 μL of the sample was electrophoresed by applying the sample to 5-20% acrylamide gel. After completion of the migration, the mixture was transferred onto a nitrocellulose filter, and the filter was blocked with 5% skim milk, 50 mM Tris-HCl (pH 8.0) and 0.05% sodium azide. The filter was reacted with an anti-LTBP-1 monoclonal antibody diluted with 2% BSA, PBS and 0.05% sodium azide to 2 μg/mL at room temperature overnight. The filter was washed 3 times, and incubated with a secondary antibody solution (HRP-labeled anti-mouse IgG antibody diluted 10000-fold with 0.1% BSA/PBS) at room temperature for 2 hr. The filter was washed 5 times, and detected with a chemical luminescence substrate.

The presence or absence of an inhibitory activity of each test substance was determined based on the density and position of LTBP-1 band (molecular weight). The analysis was demonstrated in three independent experiments. The band of a well without addition of chymase was taken as a positive control (+), the band of the well of the negative control was taken as negative (−), and the presence or absence of an inhibitory activity of each test substance was visually determined from the band of the well of each test substance. The analysis results by Western blotting are shown in FIG. 8, and the determination results of the inhibitory activity are shown in Table 9.

TABLE 9

The presence or absence of inhibitory activity on LTBP-1 degradation.

| SEQ ID NO: | lane No. in FIG. 8 | inhibitory activity |
|---|---|---|
| 56 | 4, 10, 16, 24 | + |
| 56(1) | 2 | + |
| 56(17) | 12 | + |
| 56(19) | 14 | + |
| 56(23) | 15 | + |
| 56(26) | 13, 25 | + |
| 56(27) | 11 | + |
| 56(28) | 17 | + |
| 56(29) | 19 | + |
| 58 | 3, 27 | − |
| 69(1) | 18 | + |
| 72(1) | 26 | + |
| Others | | |
| marker | 1, 8, 9, 23, 31 | |
| Chymostatin | 5, 20, 28 | + |
| negative control | 6, 21, 29 | − |
| control (without addition of chymase) | 7, 22, 30 | + |

"+" shows detection of a band with the same level of density as an LTBP-1 band in the control, and "−" shows absence of detection of LTBP-1 band as clear as that of the negative control.

SEQ ID NO: 58 did not show an inhibitory activity (−). Chymostatin, a positive control, showed an inhibitory activity (+). All aptamers other than SEQ ID NO: 58, which are contained in Table 9, showed an inhibitory activity against LTBP-1 degradation.

From the above results, it was found that the aptamer of the present invention inhibits LTBP-1 degradation by chymase. Therefore, it was shown that the aptamer can be used for the prophylaxis and/or treatment of various diseases involving activation of TGF-β, such as fibrosis.

INDUSTRIAL APPLICABILITY

The aptamer and the complex of the present invention can be useful as pharmaceuticals, diagnostic agents or reagents for diseases such as cardiovascular diseases, fibrosis and the like. The aptamer and the complex of the present invention can also be useful for the purification and concentration of chymase, as well as detection and quantification of chymase.

This application is based on Japanese patent application No. 2009-140585, and the contents of which are incorporated hereinto by reference.

The invention claimed is:

1. An aptamer that binds to chymase to inhibit a chymase activity, comprising a nucleotide sequence represented by $X_1GAUAGAN_1N_2UAAX_2$ (SEQ ID NO: 21) wherein each of $X_1$ and $X_2$, whether identical or not, is A or G, and each of $N_1$ and $N_2$, whether identical or not, is A, G, C, U or T, and wherein the fourth nucleotide from the 5' end is a 2'-fluoro-modified uracil.

2. The aptamer according to claim 1, wherein $N_1N_2$ is GA, GU, GC, UU, GT or CU.

3. The aptamer according to claim 1, wherein $X_1$ and $X_2$ are both A or both G.

4. The aptamer according to claim 2, wherein at least two of the pyrimidine nucleotides has been modified or altered.

5. An aptamer that binds to chymase to inhibit a chymase activity, comprising any one of the nucleotide sequences (a), (b) and (c) below:
  (a) an aptamer comprising a nucleotide sequence selected from among SEQ ID NO: 4-20, 22-34, 38-57, 59-65 and 69-72 with the provision that the uracil may be thymine;
  (b) an aptamer comprising a nucleotide sequence selected from among SEQ ID NO: 4-20, 22-34, 38-57, 59-65 and 69-72 with the provision that the uracil may be thymine, wherein 1 to 5 nucleotides are substituted, deleted, inserted or added; and
  (c) a nucleotide sequence having an identity of 70% or more to a nucleotide sequence selected from among SEQ ID NO: 4-20, 22-34, 38-57, 59-65 and 69-72 with the provision that the uracil may be thymine.

6. The aptamer according to claim 5, wherein at least one of the nucleotides contained in the aptamer has been modified or altered.

7. An aptamer that binds to chymase to inhibit a chymase activity, comprising any one of the nucleotide sequences (a'), (b') and (c') below:
  (a') a nucleotide sequence selected from among SEQ ID NOs: 73-131 with the provision that the uracil may be thymine;
  (b') a nucleotide sequence selected from among SEQ ID NOs: 73-131 with the provision that the uracil may be thymine, wherein 1 to 5 nucleotides are substituted, deleted, inserted or added; and
  (c') a nucleotide sequence having an identity of 70% or more to a nucleotide sequence selected from among SEQ ID NOs: 73-131 with the provision that the uracil may be thymine).

8. The aptamer according to claim 1, wherein each of the hydroxy groups at the 2'-positions of respective pyrimidine nucleotides contained in the aptamer, whether identical or not, may be substituted by an atom or a group selected from the group consisting of a hydrogen atom, a fluorine atom and a methoxy group.

9. The aptamer according to claim 1, wherein each of the hydroxy groups at the 2'-positions of respective purine nucleotides contained in the aptamer, whether identical or not, may be substituted by an atom or a group selected from the group consisting of a hydrogen atom, a fluorine atom and a methoxy group.

10. A complex comprising the aptamer according to claim 1 and a functional substance.

11. The complex according to claim 10, wherein the functional substance is an affinity substance, a substance for labeling, an enzyme, a drug delivery vehicle or a drug.

12. A pharmaceutical comprising the aptamer according to claim 1 or a complex comprising the aptamer according to claim 1 and a functional substance.

13. The pharmaceutical according to claim 12, which is used to prevent or treat a cardiovascular disease or fibrosis.

14. A diagnostic reagent comprising the aptamer according to claim 1 or a complex comprising the aptamer according to claim 1 and a functional substance.

15. A chymase detection probe comprising the aptamer according to claim 1 or a complex comprising the aptamer according to claim 1 and a functional substance.

16. A solid phase carrier for chymase purification comprising the aptamer according to claim 1 or a complex comprising the aptamer according to claim 1 and a functional substance.

17. A method of detecting chymase in a sample, comprising contacting the sample with the aptamer according to claim 1 or a complex comprising the aptamer according to claim 1 and a functional substance, and detecting chymase bound to the aptamer or the complex.

18. A method of purifying chymase from a sample, comprising contacting the sample with the aptamer according to claim 1 or a complex comprising the aptamer according to claim 1 and a functional substance, and separating chymase bound to the aptamer or the complex from the sample.

19. The aptamer according to claim 3, wherein at least two of the pyrimidine nucleotides has been modified or altered.

20. A method of preventing or treating a cardiovascular disease or fibrosis in a subject in need thereof, comprising administrating to the subject a prophylactically or therapeutically effective amount of the aptamer according to claim 1 or a complex comprising the aptamer according to claim 1 and a functional substance.

21. The aptamer according to claim 1, wherein the tenth nucleotide from the 5' end is a 2'-fluoro-modified uracil.

* * * * *

SEQUENCE LISTING

```
<160> NUMBER OF SEQ ID NOS: 131

<210> SEQ ID NO 1
<211> LENGTH: 70
<212> TYPE: DNA
<213> ORGANISM: Artificial sequence
<220> FEATURE:
<223> OTHER INFORMATION: Synthetic construct; DNA template for producing
      aptamer to chymase
<220> FEATURE:
<221> NAME/KEY: misc_feature
```

<222> LOCATION: (18)..(57)
<223> OTHER INFORMATION: n is a, c, g, or t

<400> SEQUENCE: 1
gcggccgctc ttctatgnnn nnnnnnnnn nnnnnnnnnn nnnnnnnnnn nnnnnnngaa    60
ttcctaccgt                                                          70

<210> SEQ ID NO 2
<211> LENGTH: 33
<212> TYPE: DNA
<213> ORGANISM: Artificial sequence
<220> FEATURE:
<223> OTHER INFORMATION: Synthetic construct; primer for producing
      aptamer to chymase

<400> SEQUENCE: 2
taatacgact cactataggg acggtaggaa ttc                                33

<210> SEQ ID NO 3
<211> LENGTH: 17
<212> TYPE: DNA
<213> ORGANISM: Artificial sequence
<220> FEATURE:
<223> OTHER INFORMATION: Synthetic construct; primer for producing
      aptamer to chymase

<400> SEQUENCE: 3
gcggccgctc ttctatg                                                  17

<210> SEQ ID NO 4
<211> LENGTH: 73
<212> TYPE: RNA
<213> ORGANISM: Artificial sequence
<220> FEATURE:
<223> OTHER INFORMATION: Synthetic construct; Aptamer to chymase

<400> SEQUENCE: 4
gggacgguag gaauucgucc auucuacaga uagagauaaa guagaauuua acaaaacaua    60
gaagagcggc cgc                                                      73

<210> SEQ ID NO 5
<211> LENGTH: 72
<212> TYPE: RNA
<213> ORGANISM: Artificial sequence
<220> FEATURE:
<223> OTHER INFORMATION: Synthetic construct; Aptamer to chymase

<400> SEQUENCE: 5
gggacgguag gaauucccac uugucuuuga ggcaagaaau uguauuccga agaagcauag    60
aagagcggcc gc                                                       72

<210> SEQ ID NO 6
<211> LENGTH: 73
<212> TYPE: RNA
<213> ORGANISM: Artificial sequence
<220> FEATURE:
<223> OTHER INFORMATION: Synthetic construct; Aptamer to chymase

<400> SEQUENCE: 6
gggacgguag gaauucuacg gucuguguga aauugaaaca cacaaagaac aauagacaua    60
gaagagcggc cgc                                                      73

<210> SEQ ID NO 7

```
<211> LENGTH: 73
<212> TYPE: RNA
<213> ORGANISM: Artificial sequence
<220> FEATURE:
<223> OTHER INFORMATION: Synthetic construct; Aptamer to chymase

<400> SEQUENCE: 7
gggacgguag gaauucaccu uuccaauugu gaaagaaaca caaaagaaa ugacaucaua      60 gaagagcggc cgc                                                        73

<210> SEQ ID NO 8
<211> LENGTH: 73
<212> TYPE: RNA
<213> ORGANISM: Artificial sequence
<220> FEATURE:
<223> OTHER INFORMATION: Synthetic construct; Aptamer to chymase

<400> SEQUENCE: 8
gggacgguag gaauucuacg gucuguguga aauugaaaca cacaaagaac aauaaacaua     60
gaagagcggc cgc                                                        73

<210> SEQ ID NO 9
<211> LENGTH: 74
<212> TYPE: RNA
<213> ORGANISM: Artificial sequence
<220> FEATURE:
<223> OTHER INFORMATION: Synthetic construct; Aptamer to chymase

<400> SEQUENCE: 9
gggacgguag gaauucccga aaagcaacaa gcuugcuaaa augauuccga aaaacacau      60 agaagagcgg ccgc                                                       74

<210> SEQ ID NO 10
<211> LENGTH: 73
<212> TYPE: RNA
<213> ORGANISM: Artificial sequence
<220> FEATURE:
<223> OTHER INFORMATION: Synthetic construct; Aptamer to chymase

<400> SEQUENCE: 10
gggacgguag gaauuccgcc gccuaaaaaa cgacgauauu acagaaacgu caaauacaua    60
gaagagcggc cgc                                                        73

<210> SEQ ID NO 11
<211> LENGTH: 73
<212> TYPE: RNA
<213> ORGANISM: Artificial sequence
<220> FEATURE:
<223> OTHER INFORMATION: Synthetic construct; Aptamer to chymase

<400> SEQUENCE: 11
gggacgguag gaauucccga cacgaaaugu gugauuaauu ccgaacaaca aaguaacaua    60
gaagagcggc cgc                                                        73

<210> SEQ ID NO 12
<211> LENGTH: 73
<212> TYPE: RNA
<213> ORGANISM: Artificial sequence
<220> FEATURE:
<223> OTHER INFORMATION: Synthetic construct; Aptamer to chymase

<400> SEQUENCE: 12
gggacgguag gaauucgccg ucaacguuac auaauguaua uaccagggua acuaaacaua    60
```

```
gaagagcggc cgc                                                          73

<210> SEQ ID NO 13
<211> LENGTH: 73
<212> TYPE: RNA
<213> ORGANISM: Artificial sequence
<220> FEATURE:
<223> OTHER INFORMATION: Synthetic construct; Aptamer to chymase

<400> SEQUENCE: 13
gggacgguag gaauuccgca accaucccgu aacuaugguu agauagaguu aaaaaccaua       60
gaagagcggc cgc                                                          73

<210> SEQ ID NO 14
<211> LENGTH: 73
<212> TYPE: RNA
<213> ORGANISM: Artificial sequence
<220> FEATURE:
<223> OTHER INFORMATION: Synthetic construct; Aptamer to chymase

<400> SEQUENCE: 14
gggacgguag gaauucucgu uccugacagc auuugagaua gauuuaaaca aacgcacaua       60
gaagagcggc cgc                                                          73

<210> SEQ ID NO 15
<211> LENGTH: 73
<212> TYPE: RNA
<213> ORGANISM: Artificial sequence
<220> FEATURE:
<223> OTHER INFORMATION: Synthetic construct; Aptamer to chymase

<400> SEQUENCE: 15
gggacgguag gaauucccag aaaauaaauu ccgaagaaaa caacaauuuu ugcaaacaua       60
gaagagcggc cgc                                                          73

<210> SEQ ID NO 16
<211> LENGTH: 72
<212> TYPE: RNA
<213> ORGANISM: Artificial sequence
<220> FEATURE:
<223> OTHER INFORMATION: Synthetic construct; Aptamer to chymase

<400> SEQUENCE: 16
gggacgguag gaauucccau gacugaaaaa cgucaguaaa auccgaaaau cauaucauag       60
aagagcggcc gc                                                           72

<210> SEQ ID NO 17
<211> LENGTH: 74
<212> TYPE: RNA
<213> ORGANISM: Artificial sequence
<220> FEATURE:
<223> OTHER INFORMATION: Synthetic construct; Aptamer to chymase

<400> SEQUENCE: 17
gggacgguag gaauuccguu cgcagaaacg aacuuuuaaa aaauguacgu gggagcacau       60
agaagagcgg ccgc                                                         74

<210> SEQ ID NO 18
<211> LENGTH: 73
<212> TYPE: RNA
<213> ORGANISM: Artificial sequence
<220> FEATURE:
```

<223> OTHER INFORMATION: Synthetic construct; Aptamer to chymase

<400> SEQUENCE: 18
gggacgguag gaauucgaac gacaaauuau agaacuucgu uugacauucc acaccacaua    60
gaagagcggc cgc    73

<210> SEQ ID NO 19
<211> LENGTH: 73
<212> TYPE: RNA
<213> ORGANISM: Artificial sequence
<220> FEATURE:
<223> OTHER INFORMATION: Synthetic construct; Aptamer to chymase

<400> SEQUENCE: 19
gggacgguag gaauucccac ugcaauucag cagaaaaaau uccgaaaaac acacaccaua    60
gaagagcggc cgc    73

<210> SEQ ID NO 20
<211> LENGTH: 73
<212> TYPE: RNA
<213> ORGANISM: Artificial sequence
<220> FEATURE:
<223> OTHER INFORMATION: Synthetic construct; Aptamer to chymase

<400> SEQUENCE: 20
gggacgguag gaauucaaaa ucagcugauu uguaauuuuu uuacacaggc aaaacacaua    60
gaagagcggc cgc    73

<210> SEQ ID NO 21
<211> LENGTH: 13
<212> TYPE: DNA
<213> ORGANISM: Artificial sequence
<220> FEATURE:
<223> OTHER INFORMATION: Synthetic construct; Consensus sequence of
      Aptamer to chymase
<220> FEATURE:
<221> NAME/KEY: misc_feature
<223> OTHER INFORMATION: Aptamer can be DNA or RNA
<220> FEATURE:
<221> NAME/KEY: misc_feature
<222> LOCATION: (1)..(1)
<223> OTHER INFORMATION: n is a or g
<220> FEATURE:
<221> NAME/KEY: misc_feature
<222> LOCATION: (8)..(9)
<223> OTHER INFORMATION: n is a, c, g, u, or t
<220> FEATURE:
<221> NAME/KEY: misc_feature
<222> LOCATION: (13)..(13)
<223> OTHER INFORMATION: n is a or g

<400> SEQUENCE: 21
ngauagannu aan    13

<210> SEQ ID NO 22
<211> LENGTH: 73
<212> TYPE: RNA
<213> ORGANISM: Artificial sequence
<220> FEATURE:
<223> OTHER INFORMATION: Synthetic construct; Aptamer to chymase

<400> SEQUENCE: 22
gggacgguag gaauucccga cacaaaaugu gugauuaauu ccgaacaaca aaguaacaua    60
gaagagcggc cgc    73

```
<210> SEQ ID NO 23
<211> LENGTH: 73
<212> TYPE: RNA
<213> ORGANISM: Artificial sequence
<220> FEATURE:
<223> OTHER INFORMATION: Synthetic construct; Aptamer to chymase

<400> SEQUENCE: 23
gggacgguag gaauucauau guacuccguc cugacaaaau gucaaugaca aacguucaua    60
gaagagcggc cgc                                                      73

<210> SEQ ID NO 24
<211> LENGTH: 72
<212> TYPE: RNA
<213> ORGANISM: Artificial sequence
<220> FEATURE:
<223> OTHER INFORMATION: Synthetic construct; Aptamer to chymase

<400> SEQUENCE: 24
gggacgguag gaauucccuu cauaguagaa uguuggurruc uacaaaagcg acaagcauag    60
aagagcggcc gc                                                        72

<210> SEQ ID NO 25
<211> LENGTH: 73
<212> TYPE: RNA
<213> ORGANISM: Artificial sequence
<220> FEATURE:
<223> OTHER INFORMATION: Synthetic construct; Aptamer to chymase

<400> SEQUENCE: 25
gggacgguag gaauucagcu gacuccaaug cacacguaga uagaguuaaa acguugcaua    60
gaagagcggc cgc                                                      73

<210> SEQ ID NO 26
<211> LENGTH: 73
<212> TYPE: RNA
<213> ORGANISM: Artificial sequence
<220> FEATURE:
<223> OTHER INFORMATION: Synthetic construct; Aptamer to chymase

<400> SEQUENCE: 26
gggacgguag gaauucgucg auucuacaga uagagauaaa guagaauuua acaaaacaua    60
gaagagcggc cgc                                                      73

<210> SEQ ID NO 27
<211> LENGTH: 73
<212> TYPE: RNA
<213> ORGANISM: Artificial sequence
<220> FEATURE:
<223> OTHER INFORMATION: Synthetic construct; Aptamer to chymase

<400> SEQUENCE: 27
gggacgguag gaauuccguc aucgguugca aauugaaaau acaaaacaag gacaaccaua    60
gaagagcggc cgc                                                      73

<210> SEQ ID NO 28
<211> LENGTH: 73
<212> TYPE: RNA
<213> ORGANISM: Artificial sequence
<220> FEATURE:
<223> OTHER INFORMATION: Synthetic construct; Aptamer to chymase

<400> SEQUENCE: 28
```
gggacgguag gaauucaauu ucuuucuauu cucaccugag uauaucaggc acaguacaua    60
gaagagcggc cgc    73

<210> SEQ ID NO 29
<211> LENGTH: 73
<212> TYPE: RNA
<213> ORGANISM: Artificial sequence
<220> FEATURE:
<223> OTHER INFORMATION: Synthetic construct; Aptamer to chymase

<400> SEQUENCE: 29
gggacgguag gaauucacga ccgcccaaaa aauggugaca uuuuagaaac accgaacaua    60
gaagagcggc cgc    73

<210> SEQ ID NO 30
<211> LENGTH: 71
<212> TYPE: RNA
<213> ORGANISM: Artificial sequence
<220> FEATURE:
<223> OTHER INFORMATION: Synthetic construct; Aptamer to chymase

<400> SEQUENCE: 30
gggacgguag gaauucgucc cucuugucua uuuugcagau agacuuaaag caaacauaga    60
agagcggccg c    71

<210> SEQ ID NO 31
<211> LENGTH: 71
<212> TYPE: RNA
<213> ORGANISM: Artificial sequence
<220> FEATURE:
<223> OTHER INFORMATION: Synthetic construct; Aptamer to chymase

<400> SEQUENCE: 31
gggacgguag gaauucgucc cucaugucua uuuugcagau agacuuaaag caaacauaga    60
agagcggccg c    71

<210> SEQ ID NO 32
<211> LENGTH: 70
<212> TYPE: RNA
<213> ORGANISM: Artificial sequence
<220> FEATURE:
<223> OTHER INFORMATION: Synthetic construct; Aptamer to chymase

<400> SEQUENCE: 32
gggacgguag gaauucgucc ucaugucuau uuugcagaua gacuuaaagc aaacauagaa    60
gagcggccgc    70

<210> SEQ ID NO 33
<211> LENGTH: 73
<212> TYPE: RNA
<213> ORGANISM: Artificial sequence
<220> FEATURE:
<223> OTHER INFORMATION: Synthetic construct; Aptamer to chymase

<400> SEQUENCE: 33
gggacgguag gaauuccugu cuuuucccac gcaacaaauu acagagcuuu gcaaaacaua    60
gaagagcggc cgc    73

<210> SEQ ID NO 34
<211> LENGTH: 73
<212> TYPE: RNA
<213> ORGANISM: Artificial sequence

```
<220> FEATURE:
<223> OTHER INFORMATION: Synthetic construct; Aptamer to chymase

<400> SEQUENCE: 34
gggacgguag gaauucugcc gcaacccaau gaaaacgaag auagagauaa aucgaacaua    60
gaagagcggc cgc                                                      73

<210> SEQ ID NO 35
<211> LENGTH: 72
<212> TYPE: DNA
<213> ORGANISM: Artificial sequence
<220> FEATURE:
<223> OTHER INFORMATION: Synthetic construct; DNA template for producing
      aptamer to chymase
<220> FEATURE:
<221> NAME/KEY: misc_feature
<222> LOCATION: (20)..(49)
<223> OTHER INFORMATION: n is a, c, g, or t

<400> SEQUENCE: 35
tcacactagc acgcataggn nnnnnnnnnn nnnnnnnnnn nnnnnnnnnc atctgacctc    60
tctcctgctc cc                                                       72

<210> SEQ ID NO 36
<211> LENGTH: 40
<212> TYPE: DNA
<213> ORGANISM: Artificial sequence
<220> FEATURE:
<223> OTHER INFORMATION: Synthetic construct; primer for producing
      aptamer to chymase

<400> SEQUENCE: 36
taatacgact cactataggg agcaggagag aggtcagatg                         40

<210> SEQ ID NO 37
<211> LENGTH: 19
<212> TYPE: DNA
<213> ORGANISM: Artificial sequence
<220> FEATURE:
<223> OTHER INFORMATION: Synthetic construct; primer for producing
      aptamer to chymase

<400> SEQUENCE: 37
tcacactagc acgcatagg                                                19

<210> SEQ ID NO 38
<211> LENGTH: 72
<212> TYPE: RNA
<213> ORGANISM: Artificial sequence
<220> FEATURE:
<223> OTHER INFORMATION: Synthetic construct; Aptamer to chymase

<400> SEQUENCE: 38
gggagcagga gagaggucag auggauagag uuaagaucug gcuggcgcau uagccuaugc    60
gugcuagugu ga                                                       72

<210> SEQ ID NO 39
<211> LENGTH: 72
<212> TYPE: RNA
<213> ORGANISM: Artificial sequence
<220> FEATURE:
<223> OTHER INFORMATION: Synthetic construct; Aptamer to chymase

<400> SEQUENCE: 39
gggagcagga gagaggucag augguuacgg auagaguuaa gguaacggua cggccuaugc    60
```

-continued

```
gugcuagugu ga                                                          72

<210> SEQ ID NO 40
<211> LENGTH: 73
<212> TYPE: RNA
<213> ORGANISM: Artificial sequence
<220> FEATURE:
<223> OTHER INFORMATION: Synthetic construct; Aptamer to chymase

<400> SEQUENCE: 40
gggagcagga gagaggucag augaacggau agagcuaaga guucgucaga ggggccuaug      60
cgugcuagug uga                                                         73

<210> SEQ ID NO 41
<211> LENGTH: 72
<212> TYPE: RNA
<213> ORGANISM: Artificial sequence
<220> FEATURE:
<223> OTHER INFORMATION: Synthetic construct; Aptamer to chymase

<400> SEQUENCE: 41
gggagcagga gagaggucag auggugagau agaguuaaac accacaauag uagccuaugc      60
gugcuagugu ga                                                          72

<210> SEQ ID NO 42
<211> LENGTH: 72
<212> TYPE: RNA
<213> ORGANISM: Artificial sequence
<220> FEATURE:
<223> OTHER INFORMATION: Synthetic construct; Aptamer to chymase

<400> SEQUENCE: 42
gggagcagga gagaggucag augcgugauc gugcaaggcg gauagaguua aggccuaugc      60
gugcuagugu ga                                                          72

<210> SEQ ID NO 43
<211> LENGTH: 72
<212> TYPE: RNA
<213> ORGANISM: Artificial sequence
<220> FEATURE:
<223> OTHER INFORMATION: Synthetic construct; Aptamer to chymase

<400> SEQUENCE: 43
gggagcagga gagaggucag augaugccaa gauagauuua aauggcguuu gggccuaugc      60
gugcuagugu ga                                                          72

<210> SEQ ID NO 44
<211> LENGTH: 72
<212> TYPE: RNA
<213> ORGANISM: Artificial sequence
<220> FEATURE:
<223> OTHER INFORMATION: Synthetic construct; Aptamer to chymase

<400> SEQUENCE: 44
gggagcagga gagaggucag auguuagacc aaagcauagg agauagaguu aaaccuaugc      60
gugcuagugu ga                                                          72

<210> SEQ ID NO 45
<211> LENGTH: 72
<212> TYPE: RNA
<213> ORGANISM: Artificial sequence
<220> FEATURE:
```

<223> OTHER INFORMATION: Synthetic construct; Aptamer to chymase

<400> SEQUENCE: 45
gggagcagga gagaggucag auggaccacc gaugggcaag auagaguuaa augccuaugc    60
gugcuagugu ga    72

<210> SEQ ID NO 46
<211> LENGTH: 72
<212> TYPE: RNA
<213> ORGANISM: Artificial sequence
<220> FEATURE:
<223> OTHER INFORMATION: Synthetic construct; Aptamer to chymase

<400> SEQUENCE: 46
gggagcagga gagaggucag augggacaga uagaguuaaa guccguuacg uggccuaugc    60
gugcuagugu ga    72

<210> SEQ ID NO 47
<211> LENGTH: 72
<212> TYPE: RNA
<213> ORGANISM: Artificial sequence
<220> FEATURE:
<223> OTHER INFORMATION: Synthetic construct; Aptamer to chymase

<400> SEQUENCE: 47
gggagcagga gagaggucag auggugauag auagaguuaa aaucgcugaa uggccuaugc    60
gugcuagugu ga    72

<210> SEQ ID NO 48
<211> LENGTH: 72
<212> TYPE: RNA
<213> ORGANISM: Artificial sequence
<220> FEATURE:
<223> OTHER INFORMATION: Synthetic construct; Aptamer to chymase

<400> SEQUENCE: 48
gggagcagga gagaggucag augugaagau agagauaaau cacauacagu cggccuaugc    60
gugcuagugu ga    72

<210> SEQ ID NO 49
<211> LENGTH: 29
<212> TYPE: RNA
<213> ORGANISM: Artificial sequence
<220> FEATURE:
<223> OTHER INFORMATION: Synthetic construct; Aptamer to chymase

<400> SEQUENCE: 49
gguucuacag auagagauaa aguagaacc    29

<210> SEQ ID NO 50
<211> LENGTH: 35
<212> TYPE: RNA
<213> ORGANISM: Artificial sequence
<220> FEATURE:
<223> OTHER INFORMATION: Synthetic construct; Aptamer to chymase

<400> SEQUENCE: 50
ggcauucuac agauagagau aaaguagaau uuaac    35

<210> SEQ ID NO 51
<211> LENGTH: 45
<212> TYPE: RNA
<213> ORGANISM: Artificial sequence

```
<220> FEATURE:
<223> OTHER INFORMATION: Synthetic construct; Aptamer to chymase

<400> SEQUENCE: 51
cguuacauaa uguauauacc aggguaacua aacauagaag agcgg              45

<210> SEQ ID NO 52
<211> LENGTH: 26
<212> TYPE: RNA
<213> ORGANISM: Artificial sequence
<220> FEATURE:
<223> OTHER INFORMATION: Synthetic construct; Aptamer to chymase

<400> SEQUENCE: 52
ccguauauac caggguaacu aaacgg                                    26

<210> SEQ ID NO 53
<211> LENGTH: 42
<212> TYPE: RNA
<213> ORGANISM: Artificial sequence
<220> FEATURE:
<223> OTHER INFORMATION: Synthetic construct; Aptamer to chymase

<400> SEQUENCE: 53
ggguaacuau gguuagauag aguuaaaaac cauagaagac cc                  42

<210> SEQ ID NO 54
<211> LENGTH: 36
<212> TYPE: RNA
<213> ORGANISM: Artificial sequence
<220> FEATURE:
<223> OTHER INFORMATION: Synthetic construct; Aptamer to chymase

<400> SEQUENCE: 54
uaacuauggu uagauagagu uaaaaaccau agaaga                         36

<210> SEQ ID NO 55
<211> LENGTH: 29
<212> TYPE: RNA
<213> ORGANISM: Artificial sequence
<220> FEATURE:
<223> OTHER INFORMATION: Synthetic construct; Aptamer to chymase

<400> SEQUENCE: 55
cuaugguuag auagaguuaa aaaccauag                                 29

<210> SEQ ID NO 56
<211> LENGTH: 23
<212> TYPE: RNA
<213> ORGANISM: Artificial sequence
<220> FEATURE:
<223> OTHER INFORMATION: Synthetic construct; Aptamer against chymase

<400> SEQUENCE: 56
ggguuagaua gaguuaaaaa ccc                                       23

<210> SEQ ID NO 57
<211> LENGTH: 27
<212> TYPE: RNA
<213> ORGANISM: Artificial sequence
<220> FEATURE:
<223> OTHER INFORMATION: Synthetic construct; Aptamer against chymase

<400> SEQUENCE: 57
gcauuugaga uagauuuaaa caaacgc                                   27
```

<210> SEQ ID NO 58
<211> LENGTH: 23
<212> TYPE: RNA
<213> ORGANISM: Artificial sequence
<220> FEATURE:
<223> OTHER INFORMATION: Synthetic construct; Aptamer against chymase

<400> SEQUENCE: 58
ggguugaaga uauuaagaa ccc                                             23

<210> SEQ ID NO 59
<211> LENGTH: 23
<212> TYPE: RNA
<213> ORGANISM: Artificial sequence
<220> FEATURE:
<223> OTHER INFORMATION: Synthetic construct; Aptamer against chymase

<400> SEQUENCE: 59
ggguuagaua gagauaaaaa ccc                                            23

<210> SEQ ID NO 60
<211> LENGTH: 23
<212> TYPE: RNA
<213> ORGANISM: Artificial sequence
<220> FEATURE:
<223> OTHER INFORMATION: Synthetic construct; Aptamer against chymase

<400> SEQUENCE: 60
ggguuagaua gagcuaaaaa ccc                                            23

<210> SEQ ID NO 61
<211> LENGTH: 23
<212> TYPE: RNA
<213> ORGANISM: Artificial sequence
<220> FEATURE:
<223> OTHER INFORMATION: Synthetic construct; Aptamer against chymase

<400> SEQUENCE: 61
ggguuagaua gauuuaaaaa ccc                                            23

<210> SEQ ID NO 62
<211> LENGTH: 23
<212> TYPE: RNA
<213> ORGANISM: Artificial sequence
<220> FEATURE:
<223> OTHER INFORMATION: Synthetic construct; Aptamer against chymase

<400> SEQUENCE: 62
ggguuggaua gaguuaagaa ccc                                            23

<210> SEQ ID NO 63
<211> LENGTH: 23
<212> TYPE: RNA
<213> ORGANISM: Artificial sequence
<220> FEATURE:
<223> OTHER INFORMATION: Synthetic construct; Aptamer against chymase

<400> SEQUENCE: 63
gcuacagaua gaguuaaagu agc                                            23

<210> SEQ ID NO 64
<211> LENGTH: 23
<212> TYPE: RNA
<213> ORGANISM: Artificial sequence
<220> FEATURE:
<223> OTHER INFORMATION: Synthetic construct; Aptamer against chymase

```
<400> SEQUENCE: 64
gucacagaua gaguuaaagu gac                                          23

<210> SEQ ID NO 65
<211> LENGTH: 19
<212> TYPE: RNA
<213> ORGANISM: Artificial sequence
<220> FEATURE:
<223> OTHER INFORMATION: Synthetic construct; Aptamer against chymase

<400> SEQUENCE: 65
ggcagauaga guuaaagcc                                               19

<210> SEQ ID NO 66
<211> LENGTH: 23
<212> TYPE: RNA
<213> ORGANISM: Artificial sequence
<220> FEATURE:
<223> OTHER INFORMATION: Synthetic construct; Aptamer against chymase

<400> SEQUENCE: 66
ggguuagauc gaguuaaaaa ccc                                          23

<210> SEQ ID NO 67
<211> LENGTH: 23
<212> TYPE: RNA
<213> ORGANISM: Artificial sequence
<220> FEATURE:
<223> OTHER INFORMATION: Synthetic construct; Aptamer against chymase

<400> SEQUENCE: 67
ggguuagaua caguuaaaaa ccc                                          23

<210> SEQ ID NO 68
<211> LENGTH: 23
<212> TYPE: RNA
<213> ORGANISM: Artificial sequence
<220> FEATURE:
<223> OTHER INFORMATION: Synthetic construct; Aptamer against chymase

<400> SEQUENCE: 68
ggguuagaua guguuaaaaa ccc                                          23

<210> SEQ ID NO 69
<211> LENGTH: 26
<212> TYPE: RNA
<213> ORGANISM: Artificial sequence
<220> FEATURE:
<223> OTHER INFORMATION: Synthetic construct; Aptamer against chymase

<400> SEQUENCE: 69
aaaggguuag auagaguuaa aaaccc                                       26

<210> SEQ ID NO 70
<211> LENGTH: 23
<212> TYPE: DNA
<213> ORGANISM: Artificial sequence
<220> FEATURE:
<223> OTHER INFORMATION: Synthetic construct; Aptamer against chymase

<400> SEQUENCE: 70
gggttagaua gaguuaaaaa ccc                                          23

<210> SEQ ID NO 71
```

```
<211> LENGTH: 23
<212> TYPE: DNA
<213> ORGANISM: Artificial sequence
<220> FEATURE:
<223> OTHER INFORMATION: Synthetic construct; Aptamer against chymase

<400> SEQUENCE: 71
ggguuagaua gagtuaaaaa ccc                                             23

<210> SEQ ID NO 72
<211> LENGTH: 23
<212> TYPE: DNA
<213> ORGANISM: Artificial sequence
<220> FEATURE:
<223> OTHER INFORMATION: Synthetic construct; Aptamer against chymase

<400> SEQUENCE: 72
gggttagaua gagtuaaaaa ccc                                             23

<210> SEQ ID NO 73
<211> LENGTH: 23
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: 5' idT
<220> FEATURE:
<221> NAME/KEY: misc_feature
<222> LOCATION: (4)..(5)
<223> OTHER INFORMATION: 2'-fluoro-modified residue
<220> FEATURE:
<221> NAME/KEY: misc_feature
<222> LOCATION: (9)..(9)
<223> OTHER INFORMATION: 2'-fluoro-modified residue
<220> FEATURE:
<221> NAME/KEY: misc_feature
<222> LOCATION: (14)..(15)
<223> OTHER INFORMATION: 2'-fluoro-modified residue
<220> FEATURE:
<221> NAME/KEY: misc_feature
<222> LOCATION: (21)..(23)
<223> OTHER INFORMATION: 2'-fluoro-modified residue
<220> FEATURE:
<221> NAME/KEY: misc_feature
<222> LOCATION: (23)..(23)
<223> OTHER INFORMATION: 3' idT

<400> SEQUENCE: 73
ggguuagaua gaguuaaaaa ccc                                             23

<210> SEQ ID NO 74
<211> LENGTH: 23
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(3)
<223> OTHER INFORMATION: 2' methoxy-modified residue
<220> FEATURE:
<221> NAME/KEY: misc_feature
<222> LOCATION: (4)..(5)
<223> OTHER INFORMATION: 2'-fluoro-modified residue
<220> FEATURE:
<221> NAME/KEY: misc_feature
<222> LOCATION: (9)..(9)
<223> OTHER INFORMATION: 2'-fluoro-modified residue
<220> FEATURE:
<221> NAME/KEY: misc_feature
```

<222> LOCATION: (14)..(15)
<223> OTHER INFORMATION: 2'-fluoro-modified residue
<220> FEATURE:
<221> NAME/KEY: misc_feature
<222> LOCATION: (21)..(23)
<223> OTHER INFORMATION: 2'-fluoro-modified residue

<400> SEQUENCE: 74
ggguuagaua gaguuaaaaa ccc         23

<210> SEQ ID NO 75
<211> LENGTH: 23
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (4)..(5)
<223> OTHER INFORMATION: 2'-fluoro-modified residue
<220> FEATURE:
<221> NAME/KEY: misc_feature
<222> LOCATION: (9)..(9)
<223> OTHER INFORMATION: 2'-fluoro-modified residue
<220> FEATURE:
<221> NAME/KEY: misc_feature
<222> LOCATION: (14)..(15)
<223> OTHER INFORMATION: 2'-fluoro-modified residue
<220> FEATURE:
<221> NAME/KEY: misc_feature
<222> LOCATION: (19)..(20)
<223> OTHER INFORMATION: 2' methoxy-modified residue
<220> FEATURE:
<221> NAME/KEY: misc_feature
<222> LOCATION: (21)..(23)
<223> OTHER INFORMATION: 2'-fluoro-modified residue

<400> SEQUENCE: 75
ggguuagaua gaguuaaaaa ccc         23

<210> SEQ ID NO 76
<211> LENGTH: 23
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (4)..(5)
<223> OTHER INFORMATION: 2'-fluoro-modified residue
<220> FEATURE:
<221> NAME/KEY: misc_feature
<222> LOCATION: (9)..(9)
<223> OTHER INFORMATION: 2'-fluoro-modified residue
<220> FEATURE:
<221> NAME/KEY: misc_feature
<222> LOCATION: (10)..(10)
<223> OTHER INFORMATION: 2' methoxy-modified residue
<220> FEATURE:
<221> NAME/KEY: misc_feature
<222> LOCATION: (14)..(15)
<223> OTHER INFORMATION: 2'-fluoro-modified residue
<220> FEATURE:
<221> NAME/KEY: misc_feature
<222> LOCATION: (21)..(23)
<223> OTHER INFORMATION: 2'-fluoro-modified residue

<400> SEQUENCE: 76
ggguuagaua gaguuaaaaa ccc         23

<210> SEQ ID NO 77
<211> LENGTH: 23
<212> TYPE: RNA

```
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (4)..(5)
<223> OTHER INFORMATION: 2'-fluoro-modified residue
<220> FEATURE:
<221> NAME/KEY: misc_feature
<222> LOCATION: (9)..(9)
<223> OTHER INFORMATION: 2'-fluoro-modified residue
<220> FEATURE:
<221> NAME/KEY: misc_feature
<222> LOCATION: (14)..(15)
<223> OTHER INFORMATION: 2'-fluoro-modified residue
<220> FEATURE:
<221> NAME/KEY: misc_feature
<222> LOCATION: (16)..(17)
<223> OTHER INFORMATION: 2' methoxy-modified residue
<220> FEATURE:
<221> NAME/KEY: misc_feature
<222> LOCATION: (21)..(23)
<223> OTHER INFORMATION: 2'-fluoro-modified residue

<400> SEQUENCE: 77
ggguuagaua gaguuaaaaa ccc                                            23

<210> SEQ ID NO 78
<211> LENGTH: 23
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (4)..(5)
<223> OTHER INFORMATION: 2'-fluoro-modified residue
<220> FEATURE:
<221> NAME/KEY: misc_feature
<222> LOCATION: (7)..(7)
<223> OTHER INFORMATION: 2' methoxy-modified residue
<220> FEATURE:
<221> NAME/KEY: misc_feature
<222> LOCATION: (9)..(9)
<223> OTHER INFORMATION: 2'-fluoro-modified residue
<220> FEATURE:
<221> NAME/KEY: misc_feature
<222> LOCATION: (14)..(15)
<223> OTHER INFORMATION: 2'-fluoro-modified residue
<220> FEATURE:
<221> NAME/KEY: misc_feature
<222> LOCATION: (21)..(23)
<223> OTHER INFORMATION: 2'-fluoro-modified residue

<400> SEQUENCE: 78
ggguuagaua gaguuaaaaa ccc                                            23

<210> SEQ ID NO 79
<211> LENGTH: 23
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (4)..(5)
<223> OTHER INFORMATION: 2'-fluoro-modified residue
<220> FEATURE:
<221> NAME/KEY: misc_feature
<222> LOCATION: (8)..(8)
<223> OTHER INFORMATION: 2' methoxy-modified residue
<220> FEATURE:
<221> NAME/KEY: misc_feature
<222> LOCATION: (9)..(9)
<223> OTHER INFORMATION: 2'-fluoro-modified residue
```

```
<220> FEATURE:
<221> NAME/KEY: misc_feature
<222> LOCATION: (14)..(15)
<223> OTHER INFORMATION: 2'-fluoro-modified residue
<220> FEATURE:
<221> NAME/KEY: misc_feature
<222> LOCATION: (21)..(23)
<223> OTHER INFORMATION: 2'-fluoro-modified residue

<400> SEQUENCE: 79
ggguuagaua gaguuaaaaa ccc                                                 23

<210> SEQ ID NO 80
<211> LENGTH: 23
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (4)..(5)
<223> OTHER INFORMATION: 2'-fluoro-modified residue
<220> FEATURE:
<221> NAME/KEY: misc_feature
<222> LOCATION: (9)..(9)
<223> OTHER INFORMATION: 2'-fluoro-modified residue
<220> FEATURE:
<221> NAME/KEY: misc_feature
<222> LOCATION: (12)..(12)
<223> OTHER INFORMATION: 2' methoxy-modified residue
<220> FEATURE:
<221> NAME/KEY: misc_feature
<222> LOCATION: (14)..(15)
<223> OTHER INFORMATION: 2'-fluoro-modified residue
<220> FEATURE:
<221> NAME/KEY: misc_feature
<222> LOCATION: (21)..(23)
<223> OTHER INFORMATION: 2'-fluoro-modified residue

<400> SEQUENCE: 80
ggguuagaua gaguuaaaaa ccc                                                 23

<210> SEQ ID NO 81
<211> LENGTH: 23
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (4)..(5)
<223> OTHER INFORMATION: 2'-fluoro-modified residue
<220> FEATURE:
<221> NAME/KEY: misc_feature
<222> LOCATION: (9)..(9)
<223> OTHER INFORMATION: 2'-fluoro-modified residue
<220> FEATURE:
<221> NAME/KEY: misc_feature
<222> LOCATION: (14)..(15)
<223> OTHER INFORMATION: 2'-fluoro-modified residue
<220> FEATURE:
<221> NAME/KEY: misc_feature
<222> LOCATION: (18)..(18)
<223> OTHER INFORMATION: 2' methoxy-modified residue
<220> FEATURE:
<221> NAME/KEY: misc_feature
<222> LOCATION: (21)..(23)
<223> OTHER INFORMATION: 2'-fluoro-modified residue

<400> SEQUENCE: 81
ggguuagaua gaguuaaaaa ccc                                                 23

<210> SEQ ID NO 82
```

```
<211> LENGTH: 23
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (4)..(5)
<223> OTHER INFORMATION: 2'-fluoro-modified residue
<220> FEATURE:
<221> NAME/KEY: misc_feature
<222> LOCATION: (9)..(9)
<223> OTHER INFORMATION: 2'-fluoro-modified residue
<220> FEATURE:
<221> NAME/KEY: misc_feature
<222> LOCATION: (13)..(13)
<223> OTHER INFORMATION: 2' methoxy-modified residue
<220> FEATURE:
<221> NAME/KEY: misc_feature
<222> LOCATION: (14)..(15)
<223> OTHER INFORMATION: 2'-fluoro-modified residue
<220> FEATURE:
<221> NAME/KEY: misc_feature
<222> LOCATION: (21)..(23)
<223> OTHER INFORMATION: 2'-fluoro-modified residue

<400> SEQUENCE: 82
ggguuagaua gaguuaaaaa ccc                                            23

<210> SEQ ID NO 83
<211> LENGTH: 23
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (4)..(5)
<223> OTHER INFORMATION: 2'-fluoro-modified residue
<220> FEATURE:
<221> NAME/KEY: misc_feature
<222> LOCATION: (14)..(15)
<223> OTHER INFORMATION: 2'-fluoro-modified residue
<220> FEATURE:
<221> NAME/KEY: misc_feature
<222> LOCATION: (21)..(23)
<223> OTHER INFORMATION: 2'-fluoro-modified residue

<400> SEQUENCE: 83
ggguuagaua gaguuaaaaa ccc                                            23

<210> SEQ ID NO 84
<211> LENGTH: 23
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (4)..(5)
<223> OTHER INFORMATION: 2'-fluoro-modified residue
<220> FEATURE:
<221> NAME/KEY: misc_feature
<222> LOCATION: (9)..(9)
<223> OTHER INFORMATION: 2'-fluoro-modified residue
<220> FEATURE:
<221> NAME/KEY: misc_feature
<222> LOCATION: (14)..(14)
<223> OTHER INFORMATION: 2'-fluoro-modified residue
<220> FEATURE:
<221> NAME/KEY: misc_feature
<222> LOCATION: (21)..(23)
<223> OTHER INFORMATION: 2'-fluoro-modified residue

<400> SEQUENCE: 84
```

```
ggguuagaua gaguuaaaaa ccc                                          23

<210> SEQ ID NO 85
<211> LENGTH: 23
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: 5' 40 kDa branched polyethylene glycol
<220> FEATURE:
<221> NAME/KEY: misc_feature
<222> LOCATION: (4)..(5)
<223> OTHER INFORMATION: 2'-fluoro-modified residue
<220> FEATURE:
<221> NAME/KEY: misc_feature
<222> LOCATION: (9)..(9)
<223> OTHER INFORMATION: 2'-fluoro-modified residue
<220> FEATURE:
<221> NAME/KEY: misc_feature
<222> LOCATION: (14)..(15)
<223> OTHER INFORMATION: 2'-fluoro-modified residue
<220> FEATURE:
<221> NAME/KEY: misc_feature
<222> LOCATION: (21)..(23)
<223> OTHER INFORMATION: 2'-fluoro-modified residue
<220> FEATURE:
<221> NAME/KEY: misc_feature
<222> LOCATION: (23)..(23)
<223> OTHER INFORMATION: 3' idT

<400> SEQUENCE: 85
ggguuagaua gaguuaaaaa ccc                                          23

<210> SEQ ID NO 86
<211> LENGTH: 23
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (4)..(5)
<223> OTHER INFORMATION: 2'-fluoro-modified residue
<220> FEATURE:
<221> NAME/KEY: misc_feature
<222> LOCATION: (5)..(6)
<223> OTHER INFORMATION: phosphorothiolation of a phosphate group
      between residues
<220> FEATURE:
<221> NAME/KEY: misc_feature
<222> LOCATION: (9)..(9)
<223> OTHER INFORMATION: 2'-fluoro-modified residue
<220> FEATURE:
<221> NAME/KEY: misc_feature
<222> LOCATION: (14)..(15)
<223> OTHER INFORMATION: 2'-fluoro-modified residue
<220> FEATURE:
<221> NAME/KEY: misc_feature
<222> LOCATION: (21)..(23)
<223> OTHER INFORMATION: 2'-fluoro-modified residue

<400> SEQUENCE: 86
ggguuagaua gaguuaaaaa ccc                                          23

<210> SEQ ID NO 87
<211> LENGTH: 23
<212> TYPE: RNA
<213> ORGANISM: Artificial Sequence
<220> FEATURE:
<223> OTHER INFORMATION: Synthetic Construct
```

<220> FEATURE:
<221> NAME/KEY: misc_feature
<222> LOCATION: (4)..(5)
<223> OTHER INFORMATION: 2'-fluoro-modified residue
<220> FEATURE:
<221> NAME/KEY: misc_feature
<222> LOCATION: (6)..(7)
<223> OTHER INFORMATION: phosphorothiolation of a phosphate group
      between residues
<220> FEATURE:
<221> NAME/KEY: misc_feature
<222> LOCATION: (9)..(9)
<223> OTHER INFORMATION: 2'-fluoro-modified residue
<220> FEATURE:
<221> NAME/KEY: misc_feature
<222> LOCATION: (14)..(15)
<223> OTHER INFORMATION: 2'-fluoro-modified residue
<220> FEATURE:
<221> NAME/KEY: misc_feature
<222> LOCATION: (21)..(23)
<223> OTHER INFORMATION: 2'-fluoro-modified residue

<400> SEQUENCE: 87
ggguuagaua gaguuaaaaa ccc        23

<210> SEQ ID NO 88
<211> LENGTH: 23
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(3)
<223> OTHER INFORMATION: 2' methoxy-modified residue
<220> FEATURE:
<221> NAME/KEY: misc_feature
<222> LOCATION: (4)..(5)
<223> OTHER INFORMATION: 2'-fluoro-modified residue
<220> FEATURE:
<221> NAME/KEY: misc_feature
<222> LOCATION: (7)..(8)
<223> OTHER INFORMATION: 2' methoxy-modified residue
<220> FEATURE:
<221> NAME/KEY: misc_feature
<222> LOCATION: (9)..(9)
<223> OTHER INFORMATION: 2'-fluoro-modified residue
<220> FEATURE:
<221> NAME/KEY: misc_feature
<222> LOCATION: (10)..(10)
<223> OTHER INFORMATION: 2' methoxy-modified residue
<220> FEATURE:
<221> NAME/KEY: misc_feature
<222> LOCATION: (14)..(15)
<223> OTHER INFORMATION: 2'-fluoro-modified residue
<220> FEATURE:
<221> NAME/KEY: misc_feature
<222> LOCATION: (16)..(17)
<223> OTHER INFORMATION: 2' methoxy-modified residue
<220> FEATURE:
<221> NAME/KEY: misc_feature
<222> LOCATION: (19)..(20)
<223> OTHER INFORMATION: 2' methoxy-modified residue
<220> FEATURE:
<221> NAME/KEY: misc_feature
<222> LOCATION: (21)..(23)
<223> OTHER INFORMATION: 2'-fluoro-modified residue

<400> SEQUENCE: 88
ggguuagaua gaguuaaaaa ccc        23

<210> SEQ ID NO 89
<211> LENGTH: 23
<212> TYPE: RNA
<213> ORGANISM: Artificial Sequence -continued
<220> FEATURE:
<223> OTHER INFORMATION: Synthetic Construct
<220> FEATURE:
<221> NAME/KEY: misc_feature
<222> LOCATION: (1)..(3)
<223> OTHER INFORMATION: 2' methoxy-modified residue
<220> FEATURE:
<221> NAME/KEY: misc_feature
<222> LOCATION: (4)..(5)
<223> OTHER INFORMATION: 2'-fluoro-modified residue
<220> FEATURE:
<221> NAME/KEY: misc_feature
<222> LOCATION: (7)..(8)
<223> OTHER INFORMATION: 2' methoxy-modified residue
<220> FEATURE:
<221> NAME/KEY: misc_feature
<222> LOCATION: (9)..(9)
<223> OTHER INFORMATION: 2'-fluoro-modified residue
<220> FEATURE:
<221> NAME/KEY: misc_feature
<222> LOCATION: (10)..(10)
<223> OTHER INFORMATION: 2' methoxy-modified residue
<220> FEATURE:
<221> NAME/KEY: misc_feature
<222> LOCATION: (13)..(13)
<223> OTHER INFORMATION: 2' methoxy-modified residue
<220> FEATURE:
<221> NAME/KEY: misc_feature
<222> LOCATION: (14)..(15)
<223> OTHER INFORMATION: 2'-fluoro-modified residue
<220> FEATURE:
<221> NAME/KEY: misc_feature
<222> LOCATION: (16)..(20)
<223> OTHER INFORMATION: 2' methoxy-modified residue
<220> FEATURE:
<221> NAME/KEY: misc_feature
<222> LOCATION: (21)..(23)
<223> OTHER INFORMATION: 2'-fluoro-modified residue

<400> SEQUENCE: 89
ggguuagaua gaguuaaaaa ccc                                          23

<210> SEQ ID NO 90
<211> LENGTH: 23
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(3)
<223> OTHER INFORMATION: 2' methoxy-modified residue
<220> FEATURE:
<221> NAME/KEY: misc_feature
<222> LOCATION: (4)..(5)
<223> OTHER INFORMATION: 2'-fluoro-modified residue
<220> FEATURE:
<221> NAME/KEY: misc_feature
<222> LOCATION: (5)..(6)
<223> OTHER INFORMATION: phosphorothiolation of a phosphate group
    between residues
<220> FEATURE:
<221> NAME/KEY: misc_feature
<222> LOCATION: (7)..(8)
<223> OTHER INFORMATION: 2' methoxy-modified residue
<220> FEATURE:
<221> NAME/KEY: misc_feature
<222> LOCATION: (9)..(9)
<223> OTHER INFORMATION: 2'-fluoro-modified residue
<220> FEATURE:
<221> NAME/KEY: misc_feature
<222> LOCATION: (10)..(10)
<223> OTHER INFORMATION: 2' methoxy-modified residue
<220> FEATURE:
<221> NAME/KEY: misc_feature
<222> LOCATION: (13)..(13)
<223> OTHER INFORMATION: 2' methoxy-modified residue
<220> FEATURE:
<221> NAME/KEY: misc_feature
<222> LOCATION: (14)..(15)
<223> OTHER INFORMATION: 2'-fluoro-modified residue
<220> FEATURE:
<221> NAME/KEY: misc_feature
<222> LOCATION: (16)..(20)
<223> OTHER INFORMATION: 2' methoxy-modified residue
<220> FEATURE:
<221> NAME/KEY: misc_feature
<222> LOCATION: (21)..(23)
<223> OTHER INFORMATION: 2'-fluoro-modified residue

<400> SEQUENCE: 90
ggguuagaua gaguuaaaaa ccc                                           23

<210> SEQ ID NO 91
<211> LENGTH: 23
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(3)
<223> OTHER INFORMATION: 2' methoxy-modified residue
<220> FEATURE:
<221> NAME/KEY: misc_feature
<222> LOCATION: (4)..(5)
<223> OTHER INFORMATION: 2'-fluoro-modified residue
<220> FEATURE:
<221> NAME/KEY: misc_feature
<222> LOCATION: (6)..(7)
<223> OTHER INFORMATION: phosphorothiolation of a phosphate group
      between residues
<220> FEATURE:
<221> NAME/KEY: misc_feature
<222> LOCATION: (7)..(8)
<223> OTHER INFORMATION: 2' methoxy-modified residue
<220> FEATURE:
<221> NAME/KEY: misc_feature
<222> LOCATION: (9)..(9)
<223> OTHER INFORMATION: 2'-fluoro-modified residue
<220> FEATURE:
<221> NAME/KEY: misc_feature
<222> LOCATION: (10)..(10)
<223> OTHER INFORMATION: 2' methoxy-modified residue
<220> FEATURE:
<221> NAME/KEY: misc_feature
<222> LOCATION: (13)..(13)
<223> OTHER INFORMATION: 2' methoxy-modified residue
<220> FEATURE:
<221> NAME/KEY: misc_feature
<222> LOCATION: (14)..(15)
<223> OTHER INFORMATION: 2'-fluoro-modified residue
<220> FEATURE:
<221> NAME/KEY: misc_feature
<222> LOCATION: (16)..(20)
<223> OTHER INFORMATION: 2' methoxy-modified residue
<220> FEATURE:
<221> NAME/KEY: misc_feature
<222> LOCATION: (21)..(23)
<223> OTHER INFORMATION: 2'-fluoro-modified residue

<400> SEQUENCE: 91
ggguuagaua gaguuaaaaa ccc                                           23

<210> SEQ ID NO 92
<211> LENGTH: 23
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature

```
<222> LOCATION: (1)..(1)
<223> OTHER INFORMATION: 5' idT
<220> FEATURE:
<221> NAME/KEY: misc_feature
<222> LOCATION: (1)..(3)
<223> OTHER INFORMATION: 2' methoxy-modified residue
<220> FEATURE:
<221> NAME/KEY: misc_feature
<222> LOCATION: (4)..(5)
<223> OTHER INFORMATION: 2'-fluoro-modified residue
<220> FEATURE:
<221> NAME/KEY: misc_feature
<222> LOCATION: (9)..(9)
<223> OTHER INFORMATION: 2'-fluoro-modified residue
<220> FEATURE:
<221> NAME/KEY: misc_feature
<222> LOCATION: (14)..(15)
<223> OTHER INFORMATION: 2'-fluoro-modified residue
<220> FEATURE:
<221> NAME/KEY: misc_feature
<222> LOCATION: (19)..(20)
<223> OTHER INFORMATION: 2' methoxy-modified residue
<220> FEATURE:
<221> NAME/KEY: misc_feature
<222> LOCATION: (21)..(23)
<223> OTHER INFORMATION: 2'-fluoro-modified residue
<220> FEATURE:
<221> NAME/KEY: misc_feature
<222> LOCATION: (23)..(23)
<223> OTHER INFORMATION: 3' idT

<400> SEQUENCE: 92
ggguuagaua gaguuaaaaa ccc                                              23

<210> SEQ ID NO 93
<211> LENGTH: 23
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: 5' idT
<220> FEATURE:
<221> NAME/KEY: misc_feature
<222> LOCATION: (4)..(5)
<223> OTHER INFORMATION: 2'-fluoro-modified residue
<220> FEATURE:
<221> NAME/KEY: misc_feature
<222> LOCATION: (7)..(8)
<223> OTHER INFORMATION: 2' methoxy-modified residue
<220> FEATURE:
<221> NAME/KEY: misc_feature
<222> LOCATION: (9)..(9)
<223> OTHER INFORMATION: 2'-fluoro-modified residue
<220> FEATURE:
<221> NAME/KEY: misc_feature
<222> LOCATION: (10)..(10)
<223> OTHER INFORMATION: 2' methoxy-modified residue
<220> FEATURE:
<221> NAME/KEY: misc_feature
<222> LOCATION: (14)..(15)
<223> OTHER INFORMATION: 2'-fluoro-modified residue
<220> FEATURE:
<221> NAME/KEY: misc_feature
<222> LOCATION: (21)..(23)
<223> OTHER INFORMATION: 2'-fluoro-modified residue
<220> FEATURE:
<221> NAME/KEY: misc_feature
<222> LOCATION: (23)..(23)
<223> OTHER INFORMATION: 3' idT

<400> SEQUENCE: 93
ggguuagaua gaguuaaaaa ccc                                              23
```

```
<210> SEQ ID NO 94
<211> LENGTH: 23
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: 5' idT
<220> FEATURE:
<221> NAME/KEY: misc_feature
<222> LOCATION: (1)..(3)
<223> OTHER INFORMATION: 2' methoxy-modified residue
<220> FEATURE:
<221> NAME/KEY: misc_feature
<222> LOCATION: (4)..(5)
<223> OTHER INFORMATION: 2'-fluoro-modified residue
<220> FEATURE:
<221> NAME/KEY: misc_feature
<222> LOCATION: (7)..(8)
<223> OTHER INFORMATION: 2' methoxy-modified residue
<220> FEATURE:
<221> NAME/KEY: misc_feature
<222> LOCATION: (9)..(9)
<223> OTHER INFORMATION: 2'-fluoro-modified residue
<220> FEATURE:
<221> NAME/KEY: misc_feature
<222> LOCATION: (10)..(10)
<223> OTHER INFORMATION: 2' methoxy-modified residue
<220> FEATURE:
<221> NAME/KEY: misc_feature
<222> LOCATION: (13)..(13)
<223> OTHER INFORMATION: 2' methoxy-modified residue
<220> FEATURE:
<221> NAME/KEY: misc_feature
<222> LOCATION: (14)..(15)
<223> OTHER INFORMATION: 2'-fluoro-modified residue
<220> FEATURE:
<221> NAME/KEY: misc_feature
<222> LOCATION: (16)..(20)
<223> OTHER INFORMATION: 2' methoxy-modified residue
<220> FEATURE:
<221> NAME/KEY: misc_feature
<222> LOCATION: (21)..(23)
<223> OTHER INFORMATION: 2'-fluoro-modified residue
<220> FEATURE:
<221> NAME/KEY: misc_feature
<222> LOCATION: (23)..(23)
<223> OTHER INFORMATION: 3' idT

<400> SEQUENCE: 94
ggguuagaua gaguuaaaaa ccc                                              23

<210> SEQ ID NO 95
<211> LENGTH: 23
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: 5' 40 kDa branched polyethylene glycol
<220> FEATURE:
<221> NAME/KEY: misc_feature
<222> LOCATION: (1)..(3)
<223> OTHER INFORMATION: 2' methoxy-modified residue
<220> FEATURE:
<221> NAME/KEY: misc_feature
<222> LOCATION: (4)..(5)
<223> OTHER INFORMATION: 2'-fluoro-modified residue
<220> FEATURE:
<221> NAME/KEY: misc_feature
<222> LOCATION: (7)..(8)
<223> OTHER INFORMATION: 2' methoxy-modified residue
```

-continued

```
<220> FEATURE:
<221> NAME/KEY: misc_feature
<222> LOCATION: (9)..(9)
<223> OTHER INFORMATION: 2'-fluoro-modified residue
<220> FEATURE:
<221> NAME/KEY: misc_feature
<222> LOCATION: (10)..(10)
<223> OTHER INFORMATION: 2' methoxy-modified residue
<220> FEATURE:
<221> NAME/KEY: misc_feature
<222> LOCATION: (13)..(13)
<223> OTHER INFORMATION: 2' methoxy-modified residue
<220> FEATURE:
<221> NAME/KEY: misc_feature
<222> LOCATION: (14)..(15)
<223> OTHER INFORMATION: 2'-fluoro-modified residue
<220> FEATURE:
<221> NAME/KEY: misc_feature
<222> LOCATION: (16)..(20)
<223> OTHER INFORMATION: 2' methoxy-modified residue
<220> FEATURE:
<221> NAME/KEY: misc_feature
<222> LOCATION: (21)..(23)
<223> OTHER INFORMATION: 2'-fluoro-modified residue
<220> FEATURE:
<221> NAME/KEY: misc_feature
<222> LOCATION: (23)..(23)
<223> OTHER INFORMATION: 3' idT

<400> SEQUENCE: 95
ggguuagaua gaguuaaaaa ccc                                              23

<210> SEQ ID NO 96
<211> LENGTH: 23
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (23)..(23)
<223> OTHER INFORMATION: 5' idT
<220> FEATURE:
<221> NAME/KEY: misc_feature
<222> LOCATION: (1)..(3)
<223> OTHER INFORMATION: 2' methoxy-modified residue
<220> FEATURE:
<221> NAME/KEY: misc_feature
<222> LOCATION: (4)..(5)
<223> OTHER INFORMATION: 2'-fluoro-modified residue
<220> FEATURE:
<221> NAME/KEY: misc_feature
<222> LOCATION: (6)..(7)
<223> OTHER INFORMATION: phosphorothiolation of a phosphate group
      between residues
<220> FEATURE:
<221> NAME/KEY: misc_feature
<222> LOCATION: (7)..(8)
<223> OTHER INFORMATION: 2' methoxy-modified residue
<220> FEATURE:
<221> NAME/KEY: misc_feature
<222> LOCATION: (9)..(9)
<223> OTHER INFORMATION: 2'-fluoro-modified residue
<220> FEATURE:
<221> NAME/KEY: misc_feature
<222> LOCATION: (10)..(10)
<223> OTHER INFORMATION: 2' methoxy-modified residue
<220> FEATURE:
<221> NAME/KEY: misc_feature
<222> LOCATION: (13)..(13)
<223> OTHER INFORMATION: 2' methoxy-modified residue
<220> FEATURE:
<221> NAME/KEY: misc_feature
<222> LOCATION: (14)..(15)
<223> OTHER INFORMATION: 2'-fluoro-modified residue
<220> FEATURE:
<221> NAME/KEY: misc_feature
```

```
<222> LOCATION: (16)..(20)
<223> OTHER INFORMATION: 2' methoxy-modified residue
<220> FEATURE:
<221> NAME/KEY: misc_feature
<222> LOCATION: (21)..(23)
<223> OTHER INFORMATION: 2'-fluoro-modified residue
<220> FEATURE:
<221> NAME/KEY: misc_feature
<222> LOCATION: (23)..(23)
<223> OTHER INFORMATION: 3' idT

<400> SEQUENCE: 96
ggguuagaua gaguuaaaaa ccc                                              23

<210> SEQ ID NO 97
<211> LENGTH: 23
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: 5' idT
<220> FEATURE:
<221> NAME/KEY: misc_feature
<222> LOCATION: (1)..(3)
<223> OTHER INFORMATION: 2' methoxy-modified residue
<220> FEATURE:
<221> NAME/KEY: misc_feature
<222> LOCATION: (4)..(5)
<223> OTHER INFORMATION: 2'-fluoro-modified residue
<220> FEATURE:
<221> NAME/KEY: misc_feature
<222> LOCATION: (5)..(6)
<223> OTHER INFORMATION: phosphorothiolation of a phosphate group
      between residues
<220> FEATURE:
<221> NAME/KEY: misc_feature
<222> LOCATION: (6)..(7)
<223> OTHER INFORMATION: phosphorothiolation of a phosphate group
      between residues
<220> FEATURE:
<221> NAME/KEY: misc_feature
<222> LOCATION: (7)..(8)
<223> OTHER INFORMATION: 2' methoxy-modified residue
<220> FEATURE:
<221> NAME/KEY: misc_feature
<222> LOCATION: (9)..(9)
<223> OTHER INFORMATION: 2'-fluoro-modified residue
<220> FEATURE:
<221> NAME/KEY: misc_feature
<222> LOCATION: (10)..(10)
<223> OTHER INFORMATION: 2' methoxy-modified residue
<220> FEATURE:
<221> NAME/KEY: misc_feature
<222> LOCATION: (13)..(13)
<223> OTHER INFORMATION: 2' methoxy-modified residue
<220> FEATURE:
<221> NAME/KEY: misc_feature
<222> LOCATION: (14)..(15)
<223> OTHER INFORMATION: 2'-fluoro-modified residue
<220> FEATURE:
<221> NAME/KEY: misc_feature
<222> LOCATION: (16)..(20)
<223> OTHER INFORMATION: 2' methoxy-modified residue
<220> FEATURE:
<221> NAME/KEY: misc_feature
<222> LOCATION: (21)..(23)
<223> OTHER INFORMATION: 2'-fluoro-modified residue
<220> FEATURE:
<221> NAME/KEY: misc_feature
<222> LOCATION: (23)..(23)
<223> OTHER INFORMATION: 3' idT

<400> SEQUENCE: 97
```
ggguuagaua gaguuaaaaa ccc                                          23

<210> SEQ ID NO 98
<211> LENGTH: 23
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: 5' idT
<220> FEATURE:
<221> NAME/KEY: misc_feature
<222> LOCATION: (1)..(3)
<223> OTHER INFORMATION: 2' methoxy-modified residue
<220> FEATURE:
<221> NAME/KEY: misc_feature
<222> LOCATION: (4)..(5)
<223> OTHER INFORMATION: 2'-fluoro-modified residue
<220> FEATURE:
<221> NAME/KEY: misc_feature
<222> LOCATION: (8)..(8)
<223> OTHER INFORMATION: 2' methoxy-modified residue
<220> FEATURE:
<221> NAME/KEY: misc_feature
<222> LOCATION: (9)..(9)
<223> OTHER INFORMATION: 2'-fluoro-modified residue
<220> FEATURE:
<221> NAME/KEY: misc_feature
<222> LOCATION: (10)..(10)
<223> OTHER INFORMATION: 2' methoxy-modified residue
<220> FEATURE:
<221> NAME/KEY: misc_feature
<222> LOCATION: (13)..(13)
<223> OTHER INFORMATION: 2' methoxy-modified residue
<220> FEATURE:
<221> NAME/KEY: misc_feature
<222> LOCATION: (14)..(15)
<223> OTHER INFORMATION: 2'-fluoro-modified residue
<220> FEATURE:
<221> NAME/KEY: misc_feature
<222> LOCATION: (16)..(20)
<223> OTHER INFORMATION: 2' methoxy-modified residue
<220> FEATURE:
<221> NAME/KEY: misc_feature
<222> LOCATION: (21)..(23)
<223> OTHER INFORMATION: 2'-fluoro-modified residue
<220> FEATURE:
<221> NAME/KEY: misc_feature
<222> LOCATION: (23)..(23)
<223> OTHER INFORMATION: 3' idT

<400> SEQUENCE: 98
ggguuagaua gaguuaaaaa ccc                                          23

<210> SEQ ID NO 99
<211> LENGTH: 23
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: 5' idT
<220> FEATURE:
<221> NAME/KEY: misc_feature
<222> LOCATION: (1)..(3)
<223> OTHER INFORMATION: 2' methoxy-modified residue
<220> FEATURE:
<221> NAME/KEY: misc_feature
<222> LOCATION: (4)..(5)
<223> OTHER INFORMATION: 2'-fluoro-modified residue
<220> FEATURE:
<221> NAME/KEY: misc_feature

```
<222> LOCATION: (7)..(7)
<223> OTHER INFORMATION: 2' methoxy-modified residue
<220> FEATURE:
<221> NAME/KEY: misc_feature
<222> LOCATION: (9)..(9)
<223> OTHER INFORMATION: 2'-fluoro-modified residue
<220> FEATURE:
<221> NAME/KEY: misc_feature
<222> LOCATION: (10)..(10)
<223> OTHER INFORMATION: 2' methoxy-modified residue
<220> FEATURE:
<221> NAME/KEY: misc_feature
<222> LOCATION: (13)..(13)
<223> OTHER INFORMATION: 2' methoxy-modified residue
<220> FEATURE:
<221> NAME/KEY: misc_feature
<222> LOCATION: (14)..(15)
<223> OTHER INFORMATION: 2'-fluoro-modified residue
<220> FEATURE:
<221> NAME/KEY: misc_feature
<222> LOCATION: (16)..(20)
<223> OTHER INFORMATION: 2' methoxy-modified residue
<220> FEATURE:
<221> NAME/KEY: misc_feature
<222> LOCATION: (21)..(23)
<223> OTHER INFORMATION: 2'-fluoro-modified residue
<220> FEATURE:
<221> NAME/KEY: misc_feature
<222> LOCATION: (23)..(23)
<223> OTHER INFORMATION: 3' idT

<400> SEQUENCE: 99
ggguuagaua gaguuaaaaa ccc                                            23

<210> SEQ ID NO 100
<211> LENGTH: 23
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: 5' idT
<220> FEATURE:
<221> NAME/KEY: misc_feature
<222> LOCATION: (1)..(3)
<223> OTHER INFORMATION: 2' methoxy-modified residue
<220> FEATURE:
<221> NAME/KEY: misc_feature
<222> LOCATION: (4)..(5)
<223> OTHER INFORMATION: 2'-fluoro-modified residue
<220> FEATURE:
<221> NAME/KEY: misc_feature
<222> LOCATION: (9)..(9)
<223> OTHER INFORMATION: 2'-fluoro-modified residue
<220> FEATURE:
<221> NAME/KEY: misc_feature
<222> LOCATION: (10)..(10)
<223> OTHER INFORMATION: 2' methoxy-modified residue
<220> FEATURE:
<221> NAME/KEY: misc_feature
<222> LOCATION: (13)..(13)
<223> OTHER INFORMATION: 2' methoxy-modified residue
<220> FEATURE:
<221> NAME/KEY: misc_feature
<222> LOCATION: (14)..(15)
<223> OTHER INFORMATION: 2'-fluoro-modified residue
<220> FEATURE:
<221> NAME/KEY: misc_feature
<222> LOCATION: (16)..(20)
<223> OTHER INFORMATION: 2' methoxy-modified residue
<220> FEATURE:
<221> NAME/KEY: misc_feature
<222> LOCATION: (21)..(23)
<223> OTHER INFORMATION: 2'-fluoro-modified residue
<220> FEATURE:
```

```
<221> NAME/KEY: misc_feature
<222> LOCATION: (23)..(23)
<223> OTHER INFORMATION: 3' idT

<400> SEQUENCE: 100
ggguuagaua gaguuaaaaa ccc                                              23

<210> SEQ ID NO 101
<211> LENGTH: 23
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: 5' idT
<220> FEATURE:
<221> NAME/KEY: misc_feature
<222> LOCATION: (1)..(3)
<223> OTHER INFORMATION: 2' methoxy-modified residue
<220> FEATURE:
<221> NAME/KEY: misc_feature
<222> LOCATION: (4)..(5)
<223> OTHER INFORMATION: 2'-fluoro-modified residue
<220> FEATURE:
<221> NAME/KEY: misc_feature
<222> LOCATION: (6)..(7)
<223> OTHER INFORMATION: phosphorothiolation of a phosphate group
     between residues
<220> FEATURE:
<221> NAME/KEY: misc_feature
<222> LOCATION: (8)..(8)
<223> OTHER INFORMATION: 2' methoxy-modified residue
<220> FEATURE:
<221> NAME/KEY: misc_feature
<222> LOCATION: (9)..(9)
<223> OTHER INFORMATION: 2'-fluoro-modified residue
<220> FEATURE:
<221> NAME/KEY: misc_feature
<222> LOCATION: (10)..(10)
<223> OTHER INFORMATION: 2' methoxy-modified residue
<220> FEATURE:
<221> NAME/KEY: misc_feature
<222> LOCATION: (13)..(13)
<223> OTHER INFORMATION: 2' methoxy-modified residue
<220> FEATURE:
<221> NAME/KEY: misc_feature
<222> LOCATION: (14)..(15)
<223> OTHER INFORMATION: 2'-fluoro-modified residue
<220> FEATURE:
<221> NAME/KEY: misc_feature
<222> LOCATION: (16)..(20)
<223> OTHER INFORMATION: 2' methoxy-modified residue
<220> FEATURE:
<221> NAME/KEY: misc_feature
<222> LOCATION: (21)..(23)
<223> OTHER INFORMATION: 2'-fluoro-modified residue
<220> FEATURE:
<221> NAME/KEY: misc_feature
<222> LOCATION: (23)..(23)
<223> OTHER INFORMATION: 3' idT

<400> SEQUENCE: 101
ggguuagaua gaguuaaaaa ccc                                              23

<210> SEQ ID NO 102
<211> LENGTH: 23
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
```

```
<223> OTHER INFORMATION: 5' idT
<220> FEATURE:
<221> NAME/KEY: misc_feature
<222> LOCATION: (1)..(3)
<223> OTHER INFORMATION: 2' methoxy-modified residue
<220> FEATURE:
<221> NAME/KEY: misc_feature
<222> LOCATION: (4)..(5)
<223> OTHER INFORMATION: 2'-fluoro-modified residue
<220> FEATURE:
<221> NAME/KEY: misc_feature
<222> LOCATION: (6)..(7)
<223> OTHER INFORMATION: phosphorothiolation of a phosphate group
      between residues
<220> FEATURE:
<221> NAME/KEY: misc_feature
<222> LOCATION: (7)..(7)
<223> OTHER INFORMATION: 2' methoxy-modified residue
<220> FEATURE:
<221> NAME/KEY: misc_feature
<222> LOCATION: (9)..(9)
<223> OTHER INFORMATION: 2'-fluoro-modified residue
<220> FEATURE:
<221> NAME/KEY: misc_feature
<222> LOCATION: (10)..(10)
<223> OTHER INFORMATION: 2' methoxy-modified residue
<220> FEATURE:
<221> NAME/KEY: misc_feature
<222> LOCATION: (13)..(13)
<223> OTHER INFORMATION: 2' methoxy-modified residue
<220> FEATURE:
<221> NAME/KEY: misc_feature
<222> LOCATION: (14)..(15)
<223> OTHER INFORMATION: 2'-fluoro-modified residue
<220> FEATURE:
<221> NAME/KEY: misc_feature
<222> LOCATION: (16)..(20)
<223> OTHER INFORMATION: 2' methoxy-modified residue
<220> FEATURE:
<221> NAME/KEY: misc_feature
<222> LOCATION: (21)..(23)
<223> OTHER INFORMATION: 2'-fluoro-modified residue
<220> FEATURE:
<221> NAME/KEY: misc_feature
<222> LOCATION: (23)..(23)
<223> OTHER INFORMATION: 3' idT

<400> SEQUENCE: 102
ggguuagaua gaguuaaaaa ccc                                           23

<210> SEQ ID NO 103
<211> LENGTH: 23
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: 5' idT
<220> FEATURE:
<221> NAME/KEY: misc_feature
<222> LOCATION: (1)..(3)
<223> OTHER INFORMATION: 2' methoxy-modified residue
<220> FEATURE:
<221> NAME/KEY: misc_feature
<222> LOCATION: (4)..(5)
<223> OTHER INFORMATION: 2'-fluoro-modified residue
<220> FEATURE:
<221> NAME/KEY: misc_feature
<222> LOCATION: (6)..(7)
<223> OTHER INFORMATION: phosphorothiolation of a phosphate group
      between residues
<220> FEATURE:
<221> NAME/KEY: misc_feature
<222> LOCATION: (9)..(9)
<223> OTHER INFORMATION: 2'-fluoro-modified residue
```

```
<220> FEATURE:
<221> NAME/KEY: misc_feature
<222> LOCATION: (10)..(10)
<223> OTHER INFORMATION: 2' methoxy-modified residue
<220> FEATURE:
<221> NAME/KEY: misc_feature
<222> LOCATION: (13)..(13)
<223> OTHER INFORMATION: 2' methoxy-modified residue
<220> FEATURE:
<221> NAME/KEY: misc_feature
<222> LOCATION: (14)..(15)
<223> OTHER INFORMATION: 2'-fluoro-modified residue
<220> FEATURE:
<221> NAME/KEY: misc_feature
<222> LOCATION: (16)..(20)
<223> OTHER INFORMATION: 2' methoxy-modified residue
<220> FEATURE:
<221> NAME/KEY: misc_feature
<222> LOCATION: (21)..(23)
<223> OTHER INFORMATION: 2'-fluoro-modified residue
<220> FEATURE:
<221> NAME/KEY: misc_feature
<222> LOCATION: (23)..(23)
<223> OTHER INFORMATION: 3' idT

<400> SEQUENCE: 103
ggguuagaua gaguuaaaaa ccc                                             23

<210> SEQ ID NO 104
<211> LENGTH: 23
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: 5' idT
<220> FEATURE:
<221> NAME/KEY: misc_feature
<222> LOCATION: (1)..(3)
<223> OTHER INFORMATION: 2' methoxy-modified residue
<220> FEATURE:
<221> NAME/KEY: misc_feature
<222> LOCATION: (4)..(5)
<223> OTHER INFORMATION: 2'-fluoro-modified residue
<220> FEATURE:
<221> NAME/KEY: misc_feature
<222> LOCATION: (7)..(8)
<223> OTHER INFORMATION: phosphorothiolation of a phosphate group
      between residues
<220> FEATURE:
<221> NAME/KEY: misc_feature
<222> LOCATION: (9)..(9)
<223> OTHER INFORMATION: 2'-fluoro-modified residue
<220> FEATURE:
<221> NAME/KEY: misc_feature
<222> LOCATION: (10)..(10)
<223> OTHER INFORMATION: 2' methoxy-modified residue
<220> FEATURE:
<221> NAME/KEY: misc_feature
<222> LOCATION: (13)..(13)
<223> OTHER INFORMATION: 2' methoxy-modified residue
<220> FEATURE:
<221> NAME/KEY: misc_feature
<222> LOCATION: (14)..(15)
<223> OTHER INFORMATION: 2'-fluoro-modified residue
<220> FEATURE:
<221> NAME/KEY: misc_feature
<222> LOCATION: (16)..(20)
<223> OTHER INFORMATION: 2' methoxy-modified residue
<220> FEATURE:
<221> NAME/KEY: misc_feature
<222> LOCATION: (21)..(23)
<223> OTHER INFORMATION: 2'-fluoro-modified residue
<220> FEATURE:
<221> NAME/KEY: misc_feature
```

```
<222> LOCATION: (23)..(23)
<223> OTHER INFORMATION: 3' idT

<400> SEQUENCE: 104
ggguuagaua gaguuaaaaa ccc                                                23

<210> SEQ ID NO 105
<211> LENGTH: 23
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: 5' idT
<220> FEATURE:
<221> NAME/KEY: misc_feature
<222> LOCATION: (1)..(3)
<223> OTHER INFORMATION: 2' methoxy-modified residue
<220> FEATURE:
<221> NAME/KEY: misc_feature
<222> LOCATION: (4)..(5)
<223> OTHER INFORMATION: 2'-fluoro-modified residue
<220> FEATURE:
<221> NAME/KEY: misc_feature
<222> LOCATION: (6)..(7)
<223> OTHER INFORMATION: phosphorothiolation of a phosphate group
      between residues
<220> FEATURE:
<221> NAME/KEY: misc_feature
<222> LOCATION: (7)..(8)
<223> OTHER INFORMATION: phosphorothiolation of a phosphate group
      between residues
<220> FEATURE:
<221> NAME/KEY: misc_feature
<222> LOCATION: (9)..(9)
<223> OTHER INFORMATION: 2'-fluoro-modified residue
<220> FEATURE:
<221> NAME/KEY: misc_feature
<222> LOCATION: (10)..(10)
<223> OTHER INFORMATION: 2' methoxy-modified residue
<220> FEATURE:
<221> NAME/KEY: misc_feature
<222> LOCATION: (13)..(13)
<223> OTHER INFORMATION: 2' methoxy-modified residue
<220> FEATURE:
<221> NAME/KEY: misc_feature
<222> LOCATION: (14)..(15)
<223> OTHER INFORMATION: 2'-fluoro-modified residue
<220> FEATURE:
<221> NAME/KEY: misc_feature
<222> LOCATION: (16)..(20)
<223> OTHER INFORMATION: 2' methoxy-modified residue
<220> FEATURE:
<221> NAME/KEY: misc_feature
<222> LOCATION: (21)..(23)
<223> OTHER INFORMATION: 2'-fluoro-modified residue
<220> FEATURE:
<221> NAME/KEY: misc_feature
<222> LOCATION: (23)..(23)
<223> OTHER INFORMATION: 3' idT

<400> SEQUENCE: 105
ggguuagaua gaguuaaaaa ccc                                                23

<210> SEQ ID NO 106
<211> LENGTH: 23
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
```

```
<223> OTHER INFORMATION: 5' idT
<220> FEATURE:
<221> NAME/KEY: misc_feature
<222> LOCATION: (1)..(3)
<223> OTHER INFORMATION: 2' methoxy-modified residue
<220> FEATURE:
<221> NAME/KEY: misc_feature
<222> LOCATION: (4)..(5)
<223> OTHER INFORMATION: 2'-fluoro-modified residue
<220> FEATURE:
<221> NAME/KEY: misc_feature
<222> LOCATION: (5)..(6)
<223> OTHER INFORMATION: phosphorothiolation of a phosphate group
      between residues
<220> FEATURE:
<221> NAME/KEY: misc_feature
<222> LOCATION: (6)..(7)
<223> OTHER INFORMATION: phosphorothiolation of a phosphate group
      between residues
<220> FEATURE:
<221> NAME/KEY: misc_feature
<222> LOCATION: (9)..(9)
<223> OTHER INFORMATION: 2'-fluoro-modified residue
<220> FEATURE:
<221> NAME/KEY: misc_feature
<222> LOCATION: (10)..(10)
<223> OTHER INFORMATION: 2' methoxy-modified residue
<220> FEATURE:
<221> NAME/KEY: misc_feature
<222> LOCATION: (13)..(13)
<223> OTHER INFORMATION: 2' methoxy-modified residue
<220> FEATURE:
<221> NAME/KEY: misc_feature
<222> LOCATION: (14)..(15)
<223> OTHER INFORMATION: 2'-fluoro-modified residue
<220> FEATURE:
<221> NAME/KEY: misc_feature
<222> LOCATION: (16)..(20)
<223> OTHER INFORMATION: 2' methoxy-modified residue
<220> FEATURE:
<221> NAME/KEY: misc_feature
<222> LOCATION: (21)..(23)
<223> OTHER INFORMATION: 2'-fluoro-modified residue
<220> FEATURE:
<221> NAME/KEY: misc_feature
<222> LOCATION: (23)..(23)
<223> OTHER INFORMATION: 3' idT

<400> SEQUENCE: 106
ggguuagaua gaguuaaaaa ccc                                              23

<210> SEQ ID NO 107
<211> LENGTH: 23
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: 5' 40 kDa branched polyethylene glycol
<220> FEATURE:
<221> NAME/KEY: misc_feature
<222> LOCATION: (2)..(3)
<223> OTHER INFORMATION: 2' methoxy-modified residue
<220> FEATURE:
<221> NAME/KEY: misc_feature
<222> LOCATION: (4)..(5)
<223> OTHER INFORMATION: 2'-fluoro-modified residue
<220> FEATURE:
<221> NAME/KEY: misc_feature
<222> LOCATION: (7)..(8)
<223> OTHER INFORMATION: 2' methoxy-modified residue
<220> FEATURE:
<221> NAME/KEY: misc_feature
<222> LOCATION: (9)..(9)
<223> OTHER INFORMATION: 2'-fluoro-modified residue
```

```
<220> FEATURE:
<221> NAME/KEY: misc_feature
<222> LOCATION: (10)..(10)
<223> OTHER INFORMATION: 2' methoxy-modified residue
<220> FEATURE:
<221> NAME/KEY: misc_feature
<222> LOCATION: (13)..(13)
<223> OTHER INFORMATION: 2' methoxy-modified residue
<220> FEATURE:
<221> NAME/KEY: misc_feature
<222> LOCATION: (14)..(15)
<223> OTHER INFORMATION: 2'-fluoro-modified residue
<220> FEATURE:
<221> NAME/KEY: misc_feature
<222> LOCATION: (16)..(20)
<223> OTHER INFORMATION: 2' methoxy-modified residue
<220> FEATURE:
<221> NAME/KEY: misc_feature
<222> LOCATION: (21)..(23)
<223> OTHER INFORMATION: 2'-fluoro-modified residue
<220> FEATURE:
<221> NAME/KEY: misc_feature
<222> LOCATION: (23)..(23)
<223> OTHER INFORMATION: 3' idT

<400> SEQUENCE: 107
ggguuagaua gaguuaaaaa ccc                                              23

<210> SEQ ID NO 108
<211> LENGTH: 23
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: 5' idT
<220> FEATURE:
<221> NAME/KEY: misc_feature
<222> LOCATION: (2)..(3)
<223> OTHER INFORMATION: 2' methoxy-modified residue
<220> FEATURE:
<221> NAME/KEY: misc_feature
<222> LOCATION: (4)..(5)
<223> OTHER INFORMATION: 2'-fluoro-modified residue
<220> FEATURE:
<221> NAME/KEY: misc_feature
<222> LOCATION: (7)..(8)
<223> OTHER INFORMATION: 2'-methoxy-modified residue
<220> FEATURE:
<221> NAME/KEY: misc_feature
<222> LOCATION: (9)..(9)
<223> OTHER INFORMATION: 2'-fluoro-modified residue
<220> FEATURE:
<221> NAME/KEY: misc_feature
<222> LOCATION: (10)..(10)
<223> OTHER INFORMATION: 2' methoxy-modified residue
<220> FEATURE:
<221> NAME/KEY: misc_feature
<222> LOCATION: (13)..(13)
<223> OTHER INFORMATION: 2' methoxy-modified residue
<220> FEATURE:
<221> NAME/KEY: misc_feature
<222> LOCATION: (14)..(15)
<223> OTHER INFORMATION: 2'-fluoro-modified residue
<220> FEATURE:
<221> NAME/KEY: misc_feature
<222> LOCATION: (16)..(20)
<223> OTHER INFORMATION: 2' methoxy-modified residue
<220> FEATURE:
<221> NAME/KEY: misc_feature
<222> LOCATION: (21)..(23)
<223> OTHER INFORMATION: 2'-fluoro-modified residue
<220> FEATURE:
<221> NAME/KEY: misc_feature
<222> LOCATION: (23)..(23)
```

-continued

```
<223> OTHER INFORMATION: 3' idT

<400> SEQUENCE: 108
ggguuagaua gaguuaaaaa ccc                                              23

<210> SEQ ID NO 109
<211> LENGTH: 23
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: 5' idT
<220> FEATURE:
<221> NAME/KEY: misc_feature
<222> LOCATION: (2)..(3)
<223> OTHER INFORMATION: 2' methoxy-modified residue
<220> FEATURE:
<221> NAME/KEY: misc_feature
<222> LOCATION: (4)..(5)
<223> OTHER INFORMATION: 2'-fluoro-modified residue
<220> FEATURE:
<221> NAME/KEY: misc_feature
<222> LOCATION: (6)..(7)
<223> OTHER INFORMATION: phosphorothiolation of a phosphate group
      between residues
<220> FEATURE:
<221> NAME/KEY: misc_feature
<222> LOCATION: (7)..(8)
<223> OTHER INFORMATION: 2'-methoxy-modified residue
<220> FEATURE:
<221> NAME/KEY: misc_feature
<222> LOCATION: (9)..(9)
<223> OTHER INFORMATION: 2'-fluoro-modified residue
<220> FEATURE:
<221> NAME/KEY: misc_feature
<222> LOCATION: (10)..(10)
<223> OTHER INFORMATION: 2' methoxy-modified residue
<220> FEATURE:
<221> NAME/KEY: misc_feature
<222> LOCATION: (13)..(13)
<223> OTHER INFORMATION: 2' methoxy-modified residue
<220> FEATURE:
<221> NAME/KEY: misc_feature
<222> LOCATION: (14)..(15)
<223> OTHER INFORMATION: 2'-fluoro-modified residue
<220> FEATURE:
<221> NAME/KEY: misc_feature
<222> LOCATION: (16)..(20)
<223> OTHER INFORMATION: 2' methoxy-modified residue
<220> FEATURE:
<221> NAME/KEY: misc_feature
<222> LOCATION: (21)..(23)
<223> OTHER INFORMATION: 2'-fluoro-modified residue
<220> FEATURE:
<221> NAME/KEY: misc_feature
<222> LOCATION: (23)..(23)
<223> OTHER INFORMATION: 3' idT

<400> SEQUENCE: 109
ggguuagaua gaguuaaaaa ccc                                              23

<210> SEQ ID NO 110
<211> LENGTH: 23
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: 5' Cholesterol
<220> FEATURE:
```

```
<221> NAME/KEY: misc_feature
<222> LOCATION: (1)..(3)
<223> OTHER INFORMATION: 2' methoxy-modified residue
<220> FEATURE:
<221> NAME/KEY: misc_feature
<222> LOCATION: (4)..(5)
<223> OTHER INFORMATION: 2'-fluoro-modified residue
<220> FEATURE:
<221> NAME/KEY: misc_feature
<222> LOCATION: (7)..(8)
<223> OTHER INFORMATION: 2'-methoxy-modified residue
<220> FEATURE:
<221> NAME/KEY: misc_feature
<222> LOCATION: (9)..(9)
<223> OTHER INFORMATION: 2'-fluoro-modified residue
<220> FEATURE:
<221> NAME/KEY: misc_feature
<222> LOCATION: (10)..(10)
<223> OTHER INFORMATION: 2' methoxy-modified residue
<220> FEATURE:
<221> NAME/KEY: misc_feature
<222> LOCATION: (13)..(13)
<223> OTHER INFORMATION: 2' methoxy-modified residue
<220> FEATURE:
<221> NAME/KEY: misc_feature
<222> LOCATION: (14)..(15)
<223> OTHER INFORMATION: 2'-fluoro-modified residue
<220> FEATURE:
<221> NAME/KEY: misc_feature
<222> LOCATION: (16)..(20)
<223> OTHER INFORMATION: 2' methoxy-modified residue
<220> FEATURE:
<221> NAME/KEY: misc_feature
<222> LOCATION: (21)..(23)
<223> OTHER INFORMATION: 2'-fluoro-modified residue
<220> FEATURE:
<221> NAME/KEY: misc_feature
<222> LOCATION: (23)..(23)
<223> OTHER INFORMATION: 3' idT

<400> SEQUENCE: 110
ggguuagaua gaguuaaaaa ccc                                        23

<210> SEQ ID NO 111
<211> LENGTH: 23
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: 5' disulfide conjugated Phe-Cys
<220> FEATURE:
<221> NAME/KEY: misc_feature
<222> LOCATION: (1)..(3)
<223> OTHER INFORMATION: 2' methoxy-modified residue
<220> FEATURE:
<221> NAME/KEY: misc_feature
<222> LOCATION: (4)..(5)
<223> OTHER INFORMATION: 2'-fluoro-modified residue
<220> FEATURE:
<221> NAME/KEY: misc_feature
<222> LOCATION: (7)..(8)
<223> OTHER INFORMATION: 2'-methoxy-modified residue
<220> FEATURE:
<221> NAME/KEY: misc_feature
<222> LOCATION: (9)..(9)
<223> OTHER INFORMATION: 2'-fluoro-modified residue
<220> FEATURE:
<221> NAME/KEY: misc_feature
<222> LOCATION: (10)..(10)
<223> OTHER INFORMATION: 2' methoxy-modified residue
<220> FEATURE:
<221> NAME/KEY: misc_feature
<222> LOCATION: (13)..(13)
<223> OTHER INFORMATION: 2' methoxy-modified residue
```

```
<220> FEATURE:
<221> NAME/KEY: misc_feature
<222> LOCATION: (14)..(15)
<223> OTHER INFORMATION: 2'-fluoro-modified residue
<220> FEATURE:
<221> NAME/KEY: misc_feature
<222> LOCATION: (16)..(20)
<223> OTHER INFORMATION: 2' methoxy-modified residue
<220> FEATURE:
<221> NAME/KEY: misc_feature
<222> LOCATION: (21)..(23)
<223> OTHER INFORMATION: 2'-fluoro-modified residue
<220> FEATURE:
<221> NAME/KEY: misc_feature
<222> LOCATION: (23)..(23)
<223> OTHER INFORMATION: 3' idT

<400> SEQUENCE: 111
ggguuagaua gaguuaaaaa ccc                                              23

<210> SEQ ID NO 112
<211> LENGTH: 23
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: 5' disulfide conjugated Cys-Phe
<220> FEATURE:
<221> NAME/KEY: misc_feature
<222> LOCATION: (1)..(3)
<223> OTHER INFORMATION: 2' methoxy-modified residue
<220> FEATURE:
<221> NAME/KEY: misc_feature
<222> LOCATION: (4)..(5)
<223> OTHER INFORMATION: 2'-fluoro-modified residue
<220> FEATURE:
<221> NAME/KEY: misc_feature
<222> LOCATION: (7)..(8)
<223> OTHER INFORMATION: 2'-methoxy-modified residue
<220> FEATURE:
<221> NAME/KEY: misc_feature
<222> LOCATION: (9)..(9)
<223> OTHER INFORMATION: 2'-fluoro-modified residue
<220> FEATURE:
<221> NAME/KEY: misc_feature
<222> LOCATION: (10)..(10)
<223> OTHER INFORMATION: 2' methoxy-modified residue
<220> FEATURE:
<221> NAME/KEY: misc_feature
<222> LOCATION: (13)..(13)
<223> OTHER INFORMATION: 2' methoxy-modified residue
<220> FEATURE:
<221> NAME/KEY: misc_feature
<222> LOCATION: (14)..(15)
<223> OTHER INFORMATION: 2'-fluoro-modified residue
<220> FEATURE:
<221> NAME/KEY: misc_feature
<222> LOCATION: (16)..(20)
<223> OTHER INFORMATION: 2' methoxy-modified residue
<220> FEATURE:
<221> NAME/KEY: misc_feature
<222> LOCATION: (21)..(23)
<223> OTHER INFORMATION: 2'-fluoro-modified residue
<220> FEATURE:
<221> NAME/KEY: misc_feature
<222> LOCATION: (23)..(23)
<223> OTHER INFORMATION: 3' idT

<400> SEQUENCE: 112
ggguuagaua gaguuaaaaa ccc                                              23

<210> SEQ ID NO 113
```

```
<211> LENGTH: 23
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: 5' idT
<220> FEATURE:
<221> NAME/KEY: misc_feature
<222> LOCATION: (1)..(3)
<223> OTHER INFORMATION: 2' methoxy-modified residue
<220> FEATURE:
<221> NAME/KEY: misc_feature
<222> LOCATION: (4)..(5)
<223> OTHER INFORMATION: 2'-fluoro-modified residue
<220> FEATURE:
<221> NAME/KEY: misc_feature
<222> LOCATION: (7)..(8)
<223> OTHER INFORMATION: 2'-methoxy-modified residue
<220> FEATURE:
<221> NAME/KEY: misc_feature
<222> LOCATION: (9)..(9)
<223> OTHER INFORMATION: 2'-fluoro-modified residue
<220> FEATURE:
<221> NAME/KEY: misc_feature
<222> LOCATION: (10)..(10)
<223> OTHER INFORMATION: 2' methoxy-modified residue
<220> FEATURE:
<221> NAME/KEY: misc_feature
<222> LOCATION: (13)..(13)
<223> OTHER INFORMATION: 2' methoxy-modified residue
<220> FEATURE:
<221> NAME/KEY: misc_feature
<222> LOCATION: (14)..(15)
<223> OTHER INFORMATION: 2'-fluoro-modified residue
<220> FEATURE:
<221> NAME/KEY: misc_feature
<222> LOCATION: (16)..(20)
<223> OTHER INFORMATION: 2' methoxy-modified residue
<220> FEATURE:
<221> NAME/KEY: misc_feature
<222> LOCATION: (21)..(23)
<223> OTHER INFORMATION: 2'-fluoro-modified residue
<220> FEATURE:
<221> NAME/KEY: misc_feature
<222> LOCATION: (23)..(23)
<223> OTHER INFORMATION: 3' 40 kDa branched polyethylene glycol

<400> SEQUENCE: 113
ggguuagaua gaguuaaaaa ccc                                          23

<210> SEQ ID NO 114
<211> LENGTH: 23
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: 5' B-idT
<220> FEATURE:
<221> NAME/KEY: misc_feature
<222> LOCATION: (1)..(3)
<223> OTHER INFORMATION: 2' methoxy-modified residue
<220> FEATURE:
<221> NAME/KEY: misc_feature
<222> LOCATION: (4)..(5)
<223> OTHER INFORMATION: 2'-fluoro-modified residue
<220> FEATURE:
<221> NAME/KEY: misc_feature
<222> LOCATION: (7)..(8)
<223> OTHER INFORMATION: 2'-methoxy-modified residue
<220> FEATURE:
<221> NAME/KEY: misc_feature
```

<222> LOCATION: (9)..(9)
<223> OTHER INFORMATION: 2'-fluoro-modified residue
<220> FEATURE:
<221> NAME/KEY: misc_feature
<222> LOCATION: (10)..(10)
<223> OTHER INFORMATION: 2' methoxy-modified residue
<220> FEATURE:
<221> NAME/KEY: misc_feature
<222> LOCATION: (13)..(13)
<223> OTHER INFORMATION: 2' methoxy-modified residue
<220> FEATURE:
<221> NAME/KEY: misc_feature
<222> LOCATION: (14)..(15)
<223> OTHER INFORMATION: 2'-fluoro-modified residue
<220> FEATURE:
<221> NAME/KEY: misc_feature
<222> LOCATION: (16)..(20)
<223> OTHER INFORMATION: 2' methoxy-modified residue
<220> FEATURE:
<221> NAME/KEY: misc_feature
<222> LOCATION: (21)..(23)
<223> OTHER INFORMATION: 2'-fluoro-modified residue
<220> FEATURE:
<221> NAME/KEY: misc_feature
<222> LOCATION: (23)..(23)
<223> OTHER INFORMATION: 3' idT

<400> SEQUENCE: 114
ggguuagaua gaguuaaaaa ccc                                              23

<210> SEQ ID NO 115
<211> LENGTH: 23
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: 5' idT
<220> FEATURE:
<221> NAME/KEY: misc_feature
<222> LOCATION: (1)..(3)
<223> OTHER INFORMATION: 2' methoxy-modified residue
<220> FEATURE:
<221> NAME/KEY: misc_feature
<222> LOCATION: (4)..(5)
<223> OTHER INFORMATION: 2'-fluoro-modified residue
<220> FEATURE:
<221> NAME/KEY: misc_feature
<222> LOCATION: (7)..(8)
<223> OTHER INFORMATION: 2' methoxy-modified residue
<220> FEATURE:
<221> NAME/KEY: misc_feature
<222> LOCATION: (9)..(9)
<223> OTHER INFORMATION: 2'-fluoro-modified residue
<220> FEATURE:
<221> NAME/KEY: misc_feature
<222> LOCATION: (10)..(10)
<223> OTHER INFORMATION: 2' methoxy-modified residue
<220> FEATURE:
<221> NAME/KEY: misc_feature
<222> LOCATION: (13)..(13)
<223> OTHER INFORMATION: 2' methoxy-modified residue
<220> FEATURE:
<221> NAME/KEY: misc_feature
<222> LOCATION: (14)..(15)
<223> OTHER INFORMATION: 2'-fluoro-modified residue
<220> FEATURE:
<221> NAME/KEY: misc_feature
<222> LOCATION: (16)..(20)
<223> OTHER INFORMATION: 2' methoxy-modified residue
<220> FEATURE:
<221> NAME/KEY: misc_feature
<222> LOCATION: (21)..(23)
<223> OTHER INFORMATION: 2'-fluoro-modified residue
<220> FEATURE:

<221> NAME/KEY: misc_feature
<222> LOCATION: (23)..(23)
<223> OTHER INFORMATION: 3' idT-B

<400> SEQUENCE: 115
ggguuagaua gaguuaaaaa ccc                                           23

<210> SEQ ID NO 116
<211> LENGTH: 23
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(23)
<223> OTHER INFORMATION: mixed DNA/RNA, positions 21-23 DNA,
      all other nucleotides are RNA
<220> FEATURE:
<221> NAME/KEY: misc_feature
<222> LOCATION: (1)..(1)
<223> OTHER INFORMATION: 5' idT
<220> FEATURE:
<221> NAME/KEY: misc_feature
<222> LOCATION: (1)..(3)
<223> OTHER INFORMATION: 2' methoxy-modified residue
<220> FEATURE:
<221> NAME/KEY: misc_feature
<222> LOCATION: (4)..(5)
<223> OTHER INFORMATION: 2'-fluoro-modified residue
<220> FEATURE:
<221> NAME/KEY: misc_feature
<222> LOCATION: (7)..(8)
<223> OTHER INFORMATION: 2' methoxy-modified residue
<220> FEATURE:
<221> NAME/KEY: misc_feature
<222> LOCATION: (9)..(9)
<223> OTHER INFORMATION: 2'-fluoro-modified residue
<220> FEATURE:
<221> NAME/KEY: misc_feature
<222> LOCATION: (10)..(10)
<223> OTHER INFORMATION: 2' methoxy-modified residue
<220> FEATURE:
<221> NAME/KEY: misc_feature
<222> LOCATION: (13)..(13)
<223> OTHER INFORMATION: 2' methoxy-modified residue
<220> FEATURE:
<221> NAME/KEY: misc_feature
<222> LOCATION: (14)..(15)
<223> OTHER INFORMATION: 2'-fluoro-modified residue
<220> FEATURE:
<221> NAME/KEY: misc_feature
<222> LOCATION: (16)..(20)
<223> OTHER INFORMATION: 2' methoxy-modified residue
<220> FEATURE:
<221> NAME/KEY: misc_feature
<222> LOCATION: (23)..(23)
<223> OTHER INFORMATION: 3' idT

<400> SEQUENCE: 116
ggguuagaua gaguuaaaaa ccc                                           23

<210> SEQ ID NO 117
<211> LENGTH: 23
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(23)
<223> OTHER INFORMATION: mixed DNA/RNA, position 6 DNA,
      all other nucleotides are RNA
<220> FEATURE:
<221> NAME/KEY: misc_feature

```
<222> LOCATION: (1)..(1)
<223> OTHER INFORMATION: 5' idT
<220> FEATURE:
<221> NAME/KEY: misc_feature
<222> LOCATION: (1)..(3)
<223> OTHER INFORMATION: 2' methoxy-modified residue
<220> FEATURE:
<221> NAME/KEY: misc_feature
<222> LOCATION: (4)..(5)
<223> OTHER INFORMATION: 2'-fluoro-modified residue
<220> FEATURE:
<221> NAME/KEY: misc_feature
<222> LOCATION: (7)..(7)
<223> OTHER INFORMATION: 2' methoxy-modified residue
<220> FEATURE:
<221> NAME/KEY: misc_feature
<222> LOCATION: (9)..(9)
<223> OTHER INFORMATION: 2'-fluoro-modified residue
<220> FEATURE:
<221> NAME/KEY: misc_feature
<222> LOCATION: (10)..(10)
<223> OTHER INFORMATION: 2' methoxy-modified residue
<220> FEATURE:
<221> NAME/KEY: misc_feature
<222> LOCATION: (13)..(13)
<223> OTHER INFORMATION: 2' methoxy-modified residue
<220> FEATURE:
<221> NAME/KEY: misc_feature
<222> LOCATION: (14)..(15)
<223> OTHER INFORMATION: 2'-fluoro-modified residue
<220> FEATURE:
<221> NAME/KEY: misc_feature
<222> LOCATION: (16)..(20)
<223> OTHER INFORMATION: 2' methoxy-modified residue
<220> FEATURE:
<221> NAME/KEY: misc_feature
<222> LOCATION: (21)..(23)
<223> OTHER INFORMATION: 2'-fluoro-modified residue
<220> FEATURE:
<221> NAME/KEY: misc_feature
<222> LOCATION: (23)..(23)
<223> OTHER INFORMATION: 3' idT

<400> SEQUENCE: 117
ggguuagaua gaguuaaaaa ccc                                           23

<210> SEQ ID NO 118
<211> LENGTH: 23
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(23)
<223> OTHER INFORMATION: mixed DNA/RNA, position 8 is DNA,
      all other nucleotides are RNA
<220> FEATURE:
<221> NAME/KEY: misc_feature
<222> LOCATION: (1)..(1)
<223> OTHER INFORMATION: 5' idT
<220> FEATURE:
<221> NAME/KEY: misc_feature
<222> LOCATION: (1)..(3)
<223> OTHER INFORMATION: 2' methoxy-modified residue
<220> FEATURE:
<221> NAME/KEY: misc_feature
<222> LOCATION: (4)..(5)
<223> OTHER INFORMATION: 2'-fluoro-modified residue
<220> FEATURE:
<221> NAME/KEY: misc_feature
<222> LOCATION: (7)..(7)
<223> OTHER INFORMATION: 2' methoxy-modified residue
<220> FEATURE:
<221> NAME/KEY: misc_feature
<222> LOCATION: (9)..(9)
<223> OTHER INFORMATION: 2'-fluoro-modified residue
```

```
<220> FEATURE:
<221> NAME/KEY: misc_feature
<222> LOCATION: (10)..(10)
<223> OTHER INFORMATION: 2' methoxy-modified residue
<220> FEATURE:
<221> NAME/KEY: misc_feature
<222> LOCATION: (13)..(13)
<223> OTHER INFORMATION: 2' methoxy-modified residue
<220> FEATURE:
<221> NAME/KEY: misc_feature
<222> LOCATION: (14)..(15)
<223> OTHER INFORMATION: 2'-fluoro-modified residue
<220> FEATURE:
<221> NAME/KEY: misc_feature
<222> LOCATION: (16)..(20)
<223> OTHER INFORMATION: 2' methoxy-modified residue
<220> FEATURE:
<221> NAME/KEY: misc_feature
<222> LOCATION: (21)..(23)
<223> OTHER INFORMATION: 2'-fluoro-modified residue
<220> FEATURE:
<221> NAME/KEY: misc_feature
<222> LOCATION: (23)..(23)
<223> OTHER INFORMATION: 3' idT

<400> SEQUENCE: 118
ggguuagaua gaguuaaaaa ccc                                              23

<210> SEQ ID NO 119
<211> LENGTH: 23
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(23)
<223> OTHER INFORMATION: mixed DNA/RNA, position 8 is DNA,
      all other nucleotides are RNA
<220> FEATURE:
<221> NAME/KEY: misc_feature
<222> LOCATION: (1)..(1)
<223> OTHER INFORMATION: 5' B-idT
<220> FEATURE:
<221> NAME/KEY: misc_feature
<222> LOCATION: (1)..(3)
<223> OTHER INFORMATION: 2' methoxy-modified residue
<220> FEATURE:
<221> NAME/KEY: misc_feature
<222> LOCATION: (4)..(5)
<223> OTHER INFORMATION: 2'-fluoro-modified residue
<220> FEATURE:
<221> NAME/KEY: misc_feature
<222> LOCATION: (7)..(7)
<223> OTHER INFORMATION: 2' methoxy-modified residue
<220> FEATURE:
<221> NAME/KEY: misc_feature
<222> LOCATION: (9)..(9)
<223> OTHER INFORMATION: 2'-fluoro-modified residue
<220> FEATURE:
<221> NAME/KEY: misc_feature
<222> LOCATION: (10)..(10)
<223> OTHER INFORMATION: 2' methoxy-modified residue
<220> FEATURE:
<221> NAME/KEY: misc_feature
<222> LOCATION: (13)..(13)
<223> OTHER INFORMATION: 2' methoxy-modified residue
<220> FEATURE:
<221> NAME/KEY: misc_feature
<222> LOCATION: (14)..(15)
<223> OTHER INFORMATION: 2'-fluoro-modified residue
<220> FEATURE:
<221> NAME/KEY: misc_feature
<222> LOCATION: (16)..(20)
<223> OTHER INFORMATION: 2' methoxy-modified residue
<220> FEATURE:
<221> NAME/KEY: misc_feature
```

```
<222> LOCATION: (21)..(23)
<223> OTHER INFORMATION: 2'-fluoro-modified residue
<220> FEATURE:
<221> NAME/KEY: misc_feature
<222> LOCATION: (23)..(23)
<223> OTHER INFORMATION: 3' idT

<400> SEQUENCE: 119
ggguuagaua gaguuaaaaa ccc                                              23

<210> SEQ ID NO 120
<211> LENGTH: 23
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(23)
<223> OTHER INFORMATION: mixed DNA/RNA, positions 7 and 8 is DNA,
      all other nucleotides are RNA
<220> FEATURE:
<221> NAME/KEY: misc_feature
<222> LOCATION: (1)..(1)
<223> OTHER INFORMATION: 5' idT
<220> FEATURE:
<221> NAME/KEY: misc_feature
<222> LOCATION: (1)..(3)
<223> OTHER INFORMATION: 2' methoxy-modified residue
<220> FEATURE:
<221> NAME/KEY: misc_feature
<222> LOCATION: (4)..(5)
<223> OTHER INFORMATION: 2'-fluoro-modified residue
<220> FEATURE:
<221> NAME/KEY: misc_feature
<222> LOCATION: (9)..(9)
<223> OTHER INFORMATION: 2'-fluoro-modified residue
<220> FEATURE:
<221> NAME/KEY: misc_feature
<222> LOCATION: (10)..(10)
<223> OTHER INFORMATION: 2' methoxy-modified residue
<220> FEATURE:
<221> NAME/KEY: misc_feature
<222> LOCATION: (13)..(13)
<223> OTHER INFORMATION: 2' methoxy-modified residue
<220> FEATURE:
<221> NAME/KEY: misc_feature
<222> LOCATION: (14)..(15)
<223> OTHER INFORMATION: 2'-fluoro-modified residue
<220> FEATURE:
<221> NAME/KEY: misc_feature
<222> LOCATION: (16)..(20)
<223> OTHER INFORMATION: 2' methoxy-modified residue
<220> FEATURE:
<221> NAME/KEY: misc_feature
<222> LOCATION: (21)..(23)
<223> OTHER INFORMATION: 2'-fluoro-modified residue
<220> FEATURE:
<221> NAME/KEY: misc_feature
<222> LOCATION: (23)..(23)
<223> OTHER INFORMATION: 3' idT

<400> SEQUENCE: 120
ggguuagaua gaguuaaaaa ccc                                              23

<210> SEQ ID NO 121
<211> LENGTH: 23
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(3)
<223> OTHER INFORMATION: 2' methoxy-modified residue
```

```
<220> FEATURE:
<221> NAME/KEY: misc_feature
<222> LOCATION: (4)..(5)
<223> OTHER INFORMATION: 2'-fluoro-modified residue
<220> FEATURE:
<221> NAME/KEY: misc_feature
<222> LOCATION: (7)..(8)
<223> OTHER INFORMATION: 2' methoxy-modified residue
<220> FEATURE:
<221> NAME/KEY: misc_feature
<222> LOCATION: (9)..(9)
<223> OTHER INFORMATION: 2'-fluoro-modified residue
<220> FEATURE:
<221> NAME/KEY: misc_feature
<222> LOCATION: (10)..(10)
<223> OTHER INFORMATION: 2' methoxy-modified residue
<220> FEATURE:
<221> NAME/KEY: misc_feature
<222> LOCATION: (13)..(15)
<223> OTHER INFORMATION: 2'-fluoro-modified residue
<220> FEATURE:
<221> NAME/KEY: misc_feature
<222> LOCATION: (16)..(20)
<223> OTHER INFORMATION: 2' methoxy-modified residue
<220> FEATURE:
<221> NAME/KEY: misc_feature
<222> LOCATION: (21)..(23)
<223> OTHER INFORMATION: 2'-fluoro-modified residue

<400> SEQUENCE: 121
ggguuagaua gauuuaaaaa ccc                                            23

<210> SEQ ID NO 122
<211> LENGTH: 26
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: 5' idT
<220> FEATURE:
<221> NAME/KEY: misc_feature
<222> LOCATION: (1)..(6)
<223> OTHER INFORMATION: 2' methoxy-modified residue
<220> FEATURE:
<221> NAME/KEY: misc_feature
<222> LOCATION: (7)..(8)
<223> OTHER INFORMATION: 2'-fluoro-modified residue
<220> FEATURE:
<221> NAME/KEY: misc_feature
<222> LOCATION: (9)..(10)
<223> OTHER INFORMATION: phosphorothiolation of a phosphate group
      between residues
<220> FEATURE:
<221> NAME/KEY: misc_feature
<222> LOCATION: (10)..(11)
<223> OTHER INFORMATION: 2' methoxy-modified residue
<220> FEATURE:
<221> NAME/KEY: misc_feature
<222> LOCATION: (12)..(12)
<223> OTHER INFORMATION: 2'-fluoro-modified residue
<220> FEATURE:
<221> NAME/KEY: misc_feature
<222> LOCATION: (13)..(13)
<223> OTHER INFORMATION: 2' methoxy-modified residue
<220> FEATURE:
<221> NAME/KEY: misc_feature
<222> LOCATION: (16)..(16)
<223> OTHER INFORMATION: 2' methoxy-modified residue
<220> FEATURE:
<221> NAME/KEY: misc_feature
<222> LOCATION: (17)..(18)
<223> OTHER INFORMATION: 2'-fluoro-modified residue
<220> FEATURE:
<221> NAME/KEY: misc_feature
```

```
<222> LOCATION: (19)..(23)
<223> OTHER INFORMATION: 2' methoxy-modified residue
<220> FEATURE:
<221> NAME/KEY: misc_feature
<222> LOCATION: (24)..(26)
<223> OTHER INFORMATION: 2'-fluoro-modified residue
<220> FEATURE:
<221> NAME/KEY: misc_feature
<222> LOCATION: (26)..(26)
<223> OTHER INFORMATION: 3' idT

<400> SEQUENCE: 122
aaaggguuag auagaguuaa aaaccc                                              26

<210> SEQ ID NO 123
<211> LENGTH: 26
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: 5' idT
<220> FEATURE:
<221> NAME/KEY: misc_feature
<222> LOCATION: (1)..(6)
<223> OTHER INFORMATION: 2' methoxy-modified residue
<220> FEATURE:
<221> NAME/KEY: misc_feature
<222> LOCATION: (7)..(8)
<223> OTHER INFORMATION: 2'-fluoro-modified residue
<220> FEATURE:
<221> NAME/KEY: misc_feature
<222> LOCATION: (10)..(11)
<223> OTHER INFORMATION: 2' methoxy-modified residue
<220> FEATURE:
<221> NAME/KEY: misc_feature
<222> LOCATION: (12)..(12)
<223> OTHER INFORMATION: 2'-fluoro-modified residue
<220> FEATURE:
<221> NAME/KEY: misc_feature
<222> LOCATION: (13)..(13)
<223> OTHER INFORMATION: 2' methoxy-modified residue
<220> FEATURE:
<221> NAME/KEY: misc_feature
<222> LOCATION: (16)..(16)
<223> OTHER INFORMATION: 2' methoxy-modified residue
<220> FEATURE:
<221> NAME/KEY: misc_feature
<222> LOCATION: (17)..(18)
<223> OTHER INFORMATION: 2'-fluoro-modified residue
<220> FEATURE:
<221> NAME/KEY: misc_feature
<222> LOCATION: (19)..(23)
<223> OTHER INFORMATION: 2' methoxy-modified residue
<220> FEATURE:
<221> NAME/KEY: misc_feature
<222> LOCATION: (24)..(26)
<223> OTHER INFORMATION: 2'-fluoro-modified residue
<220> FEATURE:
<221> NAME/KEY: misc_feature
<222> LOCATION: (26)..(26)
<223> OTHER INFORMATION: 3' idT

<400> SEQUENCE: 123 aaagggguuag auagaguuaa aaaccc                                             26

<210> SEQ ID NO 124
<211> LENGTH: 23
<212> TYPE: DNA
<213> ORGANISM: Artificial Sequence
<220> FEATURE:
<223> OTHER INFORMATION: Synthetic Construct
<220> FEATURE:
```

```
<221> NAME/KEY: misc_feature
<222> LOCATION: (1)..(23)
<223> OTHER INFORMATION: mixed DNA/RNA, positions 4, 5, 8, 14 and 21-23
      are DNA, the remaining nucleotides are RNA
<220> FEATURE:
<221> NAME/KEY: misc_feature
<222> LOCATION: (1)..(1)
<223> OTHER INFORMATION: 5' idT
<220> FEATURE:
<221> NAME/KEY: misc_feature
<222> LOCATION: (1)..(3)
<223> OTHER INFORMATION: 2' methoxy-modified residue
<220> FEATURE:
<221> NAME/KEY: misc_feature
<222> LOCATION: (7)..(7)
<223> OTHER INFORMATION: 2' methoxy-modified residue
<220> FEATURE:
<221> NAME/KEY: misc_feature
<222> LOCATION: (9)..(9)
<223> OTHER INFORMATION: 2'-fluoro-modified residue
<220> FEATURE:
<221> NAME/KEY: misc_feature
<222> LOCATION: (10)..(10)
<223> OTHER INFORMATION: 2' methoxy-modified residue
<220> FEATURE:
<221> NAME/KEY: misc_feature
<222> LOCATION: (13)..(13)
<223> OTHER INFORMATION: 2' methoxy-modified residue
<220> FEATURE:
<221> NAME/KEY: misc_feature
<222> LOCATION: (15)..(15)
<223> OTHER INFORMATION: 2'-fluoro-modified residue
<220> FEATURE:
<221> NAME/KEY: misc_feature
<222> LOCATION: (16)..(20)
<223> OTHER INFORMATION: 2' methoxy-modified residue
<220> FEATURE:
<221> NAME/KEY: misc_feature
<222> LOCATION: (23)..(23)
<223> OTHER INFORMATION: 3' idT

<400> SEQUENCE: 124
gggttagaua gagtuaaaaa ccc                                             23

<210> SEQ ID NO 125
<211> LENGTH: 23
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(23)
<223> OTHER INFORMATION: mixed DNA/RNA, positions 4, 5, 8, 14 and 21-23
      are DNA, the remaining nucleotides are RNA
<220> FEATURE:
<221> NAME/KEY: misc_feature
<222> LOCATION: (1)..(1)
<223> OTHER INFORMATION: 5' idT
<220> FEATURE:
<221> NAME/KEY: misc_feature
<222> LOCATION: (1)..(3)
<223> OTHER INFORMATION: 2' methoxy-modified residue
<220> FEATURE:
<221> NAME/KEY: misc_feature
<222> LOCATION: (6)..(7)
<223> OTHER INFORMATION: phosphorothiolation of a phosphate group
      between residues
<220> FEATURE:
<221> NAME/KEY: misc_feature
<222> LOCATION: (7)..(7)
<223> OTHER INFORMATION: 2' methoxy-modified residue
<220> FEATURE:
<221> NAME/KEY: misc_feature
<222> LOCATION: (9)..(9)
<223> OTHER INFORMATION: 2'-fluoro-modified residue
<220> FEATURE:
```

<221> NAME/KEY: misc_feature
<222> LOCATION: (10)..(10)
<223> OTHER INFORMATION: 2' methoxy-modified residue
<220> FEATURE:
<221> NAME/KEY: misc_feature
<222> LOCATION: (13)..(13)
<223> OTHER INFORMATION: 2' methoxy-modified residue
<220> FEATURE:
<221> NAME/KEY: misc_feature
<222> LOCATION: (15)..(15)
<223> OTHER INFORMATION: 2'-fluoro-modified residue
<220> FEATURE:
<221> NAME/KEY: misc_feature
<222> LOCATION: (16)..(20)
<223> OTHER INFORMATION: 2' methoxy-modified residue
<220> FEATURE:
<221> NAME/KEY: misc_feature
<222> LOCATION: (23)..(23)
<223> OTHER INFORMATION: 3' idT

<400> SEQUENCE: 125
gggttagaua gagtuaaaaa ccc                                           23

<210> SEQ ID NO 126
<211> LENGTH: 23
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(23)
<223> OTHER INFORMATION: mixed DNA/RNA, positions 4, 5, 13, 14 and 21-23
      are DNA, the remaining nucleotides are RNA
<220> FEATURE:
<221> NAME/KEY: misc_feature
<222> LOCATION: (1)..(1)
<223> OTHER INFORMATION: 5' idT
<220> FEATURE:
<221> NAME/KEY: misc_feature
<222> LOCATION: (1)..(3)
<223> OTHER INFORMATION: 2' methoxy-modified residue
<220> FEATURE:
<221> NAME/KEY: misc_feature
<222> LOCATION: (7)..(8)
<223> OTHER INFORMATION: 2' methoxy-modified residue
<220> FEATURE:
<221> NAME/KEY: misc_feature
<222> LOCATION: (9)..(9)
<223> OTHER INFORMATION: 2'-fluoro-modified residue
<220> FEATURE:
<221> NAME/KEY: misc_feature
<222> LOCATION: (10)..(10)
<223> OTHER INFORMATION: 2' methoxy-modified residue
<220> FEATURE:
<221> NAME/KEY: misc_feature
<222> LOCATION: (15)..(15)
<223> OTHER INFORMATION: 2'-fluoro-modified residue
<220> FEATURE:
<221> NAME/KEY: misc_feature
<222> LOCATION: (16)..(20)
<223> OTHER INFORMATION: 2' methoxy-modified residue
<220> FEATURE:
<221> NAME/KEY: misc_feature
<222> LOCATION: (23)..(23)
<223> OTHER INFORMATION: 3' idT

<400> SEQUENCE: 126
gggttagaua gagtuaaaaa ccc                                           23

<210> SEQ ID NO 127
<211> LENGTH: 23
<212> TYPE: DNA
<213> ORGANISM: Artificial Sequence
<220> FEATURE:

<223> OTHER INFORMATION: Synthetic Construct
<220> FEATURE:
<221> NAME/KEY: misc_feature
<222> LOCATION: (1)..(23)
<223> OTHER INFORMATION: mixed DNA/RNA, positions 4, 5, 14, 16 and 21-23
      are DNA, the remaining nucleotides are RNA
<220> FEATURE:
<221> NAME/KEY: misc_feature
<222> LOCATION: (1)..(1)
<223> OTHER INFORMATION: 5' idT
<220> FEATURE:
<221> NAME/KEY: misc_feature
<222> LOCATION: (1)..(3)
<223> OTHER INFORMATION: 2' methoxy-modified residue
<220> FEATURE:
<221> NAME/KEY: misc_feature
<222> LOCATION: (7)..(8)
<223> OTHER INFORMATION: 2' methoxy-modified residue
<220> FEATURE:
<221> NAME/KEY: misc_feature
<222> LOCATION: (9)..(9)
<223> OTHER INFORMATION: 2'-fluoro-modified residue
<220> FEATURE:
<221> NAME/KEY: misc_feature
<222> LOCATION: (10)..(10)
<223> OTHER INFORMATION: 2' methoxy-modified residue
<220> FEATURE:
<221> NAME/KEY: misc_feature
<222> LOCATION: (13)..(13)
<223> OTHER INFORMATION: 2' methoxy-modified residue
<220> FEATURE:
<221> NAME/KEY: misc_feature
<222> LOCATION: (15)..(15)
<223> OTHER INFORMATION: 2'-fluoro-modified residue
<220> FEATURE:
<221> NAME/KEY: misc_feature
<222> LOCATION: (17)..(20)
<223> OTHER INFORMATION: 2' methoxy-modified residue
<220> FEATURE:
<221> NAME/KEY: misc_feature
<222> LOCATION: (23)..(23)
<223> OTHER INFORMATION: 3' idT

<400> SEQUENCE: 127
gggttagaua gagtuaaaaa ccc                                          23

<210> SEQ ID NO 128
<211> LENGTH: 23
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(23)
<223> OTHER INFORMATION: mixed DNA/RNA, positions 4, 5, 14, 17 and 21-23
      are DNA, the remaining nucleotides are RNA
<220> FEATURE:
<221> NAME/KEY: misc_feature
<222> LOCATION: (1)..(1)
<223> OTHER INFORMATION: 5' idT
<220> FEATURE:
<221> NAME/KEY: misc_feature
<222> LOCATION: (1)..(3)
<223> OTHER INFORMATION: 2' methoxy-modified residue
<220> FEATURE:
<221> NAME/KEY: misc_feature
<222> LOCATION: (7)..(8)
<223> OTHER INFORMATION: 2' methoxy-modified residue
<220> FEATURE:
<221> NAME/KEY: misc_feature
<222> LOCATION: (9)..(9)
<223> OTHER INFORMATION: 2'-fluoro-modified residue
<220> FEATURE:
<221> NAME/KEY: misc_feature
<222> LOCATION: (10)..(10)
<223> OTHER INFORMATION: 2' methoxy-modified residue

```
<220> FEATURE:
<221> NAME/KEY: misc_feature
<222> LOCATION: (13)..(13)
<223> OTHER INFORMATION: 2' methoxy-modified residue
<220> FEATURE:
<221> NAME/KEY: misc_feature
<222> LOCATION: (15)..(15)
<223> OTHER INFORMATION: 2'-fluoro-modified residue
<220> FEATURE:
<221> NAME/KEY: misc_feature
<222> LOCATION: (16)..(16)
<223> OTHER INFORMATION: 2' methoxy-modified residue
<220> FEATURE:
<221> NAME/KEY: misc_feature
<222> LOCATION: (18)..(20)
<223> OTHER INFORMATION: 2' methoxy-modified residue
<220> FEATURE:
<221> NAME/KEY: misc_feature
<222> LOCATION: (23)..(23)
<223> OTHER INFORMATION: 3' idT

<400> SEQUENCE: 128
gggttagaua gagtuaaaaa ccc                                              23

<210> SEQ ID NO 129
<211> LENGTH: 23
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(23)
<223> OTHER INFORMATION: mixed DNA/RNA, positions 4, 5, 14, 18 and 21-23
      are DNA, the remaining nucleotides are RNA
<220> FEATURE:
<221> NAME/KEY: misc_feature
<222> LOCATION: (1)..(1)
<223> OTHER INFORMATION: 5' idT
<220> FEATURE:
<221> NAME/KEY: misc_feature
<222> LOCATION: (1)..(3)
<223> OTHER INFORMATION: 2' methoxy-modified residue
<220> FEATURE:
<221> NAME/KEY: misc_feature
<222> LOCATION: (7)..(8)
<223> OTHER INFORMATION: 2' methoxy-modified residue
<220> FEATURE:
<221> NAME/KEY: misc_feature
<222> LOCATION: (9)..(9)
<223> OTHER INFORMATION: 2'-fluoro-modified residue
<220> FEATURE:
<221> NAME/KEY: misc_feature
<222> LOCATION: (10)..(10)
<223> OTHER INFORMATION: 2' methoxy-modified residue
<220> FEATURE:
<221> NAME/KEY: misc_feature
<222> LOCATION: (13)..(13)
<223> OTHER INFORMATION: 2' methoxy-modified residue
<220> FEATURE:
<221> NAME/KEY: misc_feature
<222> LOCATION: (15)..(15)
<223> OTHER INFORMATION: 2'-fluoro-modified residue
<220> FEATURE:
<221> NAME/KEY: misc_feature
<222> LOCATION: (16)..(17)
<223> OTHER INFORMATION: 2' methoxy-modified residue
<220> FEATURE:
<221> NAME/KEY: misc_feature
<222> LOCATION: (19)..(20)
<223> OTHER INFORMATION: 2' methoxy-modified residue
<220> FEATURE:
<221> NAME/KEY: misc_feature
<222> LOCATION: (23)..(23)
<223> OTHER INFORMATION: 3' idT

<400> SEQUENCE: 129
```
gggttagaua gagtuaaaaa ccc                                               23

<210> SEQ ID NO 130
<211> LENGTH: 23
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(23)
<223> OTHER INFORMATION: mixed DNA/RNA, positions 4, 5, 8, 14 and 21-23
      are DNA, the remaining nucleotides are RNA
<220> FEATURE:
<221> NAME/KEY: misc_feature
<222> LOCATION: (1)..(1)
<223> OTHER INFORMATION: 5' idT
<220> FEATURE:
<221> NAME/KEY: misc_feature
<222> LOCATION: (1)..(3)
<223> OTHER INFORMATION: 2' methoxy-modified residue
<220> FEATURE:
<221> NAME/KEY: misc_feature
<222> LOCATION: (7)..(7)
<223> OTHER INFORMATION: 2' methoxy-modified residue
<220> FEATURE:
<221> NAME/KEY: misc_feature
<222> LOCATION: (9)..(9)
<223> OTHER INFORMATION: 2'-fluoro-modified residue
<220> FEATURE:
<221> NAME/KEY: misc_feature
<222> LOCATION: (10)..(10)
<223> OTHER INFORMATION: 2' methoxy-modified residue
<220> FEATURE:
<221> NAME/KEY: misc_feature
<222> LOCATION: (13)..(13)
<223> OTHER INFORMATION: 2' methoxy-modified residue
<220> FEATURE:
<221> NAME/KEY: misc_feature
<222> LOCATION: (15)..(15)
<223> OTHER INFORMATION: 2'-fluoro-modified residue
<220> FEATURE:
<221> NAME/KEY: misc_feature
<222> LOCATION: (16)..(20)
<223> OTHER INFORMATION: 2' methoxy-modified residue
<220> FEATURE:
<221> NAME/KEY: misc_feature
<222> LOCATION: (23)..(23)
<223> OTHER INFORMATION: 3' 40 kDa branched polyethylene glycol

<400> SEQUENCE: 130
gggttagaua gagtuaaaaa ccc                                               23

<210> SEQ ID NO 131
<211> LENGTH: 23
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(23)
<223> OTHER INFORMATION: mixed DNA/RNA, positions 4, 5, 8, 14 and 21-23
      are DNA, the remaining nucleotides are RNA
<220> FEATURE:
<221> NAME/KEY: misc_feature
<222> LOCATION: (1)..(1)
<223> OTHER INFORMATION: 5' B-idT
<220> FEATURE:
<221> NAME/KEY: misc_feature
<222> LOCATION: (1)..(3)
<223> OTHER INFORMATION: 2' methoxy-modified residue
<220> FEATURE:
<221> NAME/KEY: misc_feature
<222> LOCATION: (7)..(7)

```
<223> OTHER INFORMATION: 2' methoxy-modified residue
<220> FEATURE:
<221> NAME/KEY: misc_feature
<222> LOCATION: (9)..(9)
<223> OTHER INFORMATION: 2'-fluoro-modified residue
<220> FEATURE:
<221> NAME/KEY: misc_feature
<222> LOCATION: (10)..(10)
<223> OTHER INFORMATION: 2' methoxy-modified residue
<220> FEATURE:
<221> NAME/KEY: misc_feature
<222> LOCATION: (13)..(13)
<223> OTHER INFORMATION: 2' methoxy-modified residue
<220> FEATURE:
<221> NAME/KEY: misc_feature
<222> LOCATION: (15)..(15)
<223> OTHER INFORMATION: 2'-fluoro-modified residue
<220> FEATURE:
<221> NAME/KEY: misc_feature
<222> LOCATION: (16)..(20)
<223> OTHER INFORMATION: 2' methoxy-modified residue
<220> FEATURE:
<221> NAME/KEY: misc_feature
<222> LOCATION: (23)..(23)
<223> OTHER INFORMATION: 3' idT

<400> SEQUENCE: 131
gggttagaua gagtuaaaaa ccc                                            23
```